US012152259B2

(12) United States Patent
Nureki et al.

(10) Patent No.: US 12,152,259 B2
(45) Date of Patent: Nov. 26, 2024

(54) MODIFIED CAS9 PROTEIN, AND USE THEREOF

(71) Applicants: THE UNIVERSITY OF TOKYO, Tokyo (JP); MODALIS THERAPEUTICS CORPORATION, Tokyo (JP)

(72) Inventors: Osamu Nureki, Bunkyo-ku (JP); Hiroshi Nishimasu, Bunkyo-ku (JP); Hisato Hirano, Bunkyo-ku (JP); Shohei Kajimoto, Bunkyo-ku (JP); Tetsuya Yamagata, Cambridge, MA (US); Yuanbo Qin, Cambridge, MA (US); Keith M. Connolly, Cambridge, MA (US); Iain Thompson, Cambridge, MA (US)

(73) Assignees: THE UNIVERSITY OF TOKYO, Tokyo (JP); MODALIS THERAPEUTICS CORPORATION, Tokyo (JP)

( * ) Notice: Subject to any disclaimer, the term of this patent is extended or adjusted under 35 U.S.C. 154(b) by 179 days.

(21) Appl. No.: 18/058,823

(22) Filed: Nov. 25, 2022

(65) Prior Publication Data
US 2023/0279374 A1 Sep. 7, 2023

Related U.S. Application Data

(62) Division of application No. 16/644,378, filed as application No. PCT/JP2018/032948 on Sep. 5, 2018, now Pat. No. 11,530,396.

(60) Provisional application No. 62/724,981, filed on Aug. 30, 2018, provisional application No. 62/668,968, filed on May 9, 2018, provisional application No. 62/554,227, filed on Sep. 5, 2017.

(51) Int. Cl.
| | | |
|---|---|---|
| *C12N 9/22* | (2006.01) | |
| *A61K 47/54* | (2017.01) | |
| *C12N 15/11* | (2006.01) | |
| *C12N 15/113* | (2010.01) | |
| *C12N 15/90* | (2006.01) | |

(52) U.S. Cl.
CPC .............. *C12N 9/22* (2013.01); *A61K 47/549* (2017.08); *C12N 15/11* (2013.01); *C12N 15/902* (2013.01); *C12N 15/907* (2013.01); C12N 2310/20 (2017.05); C12N 2310/3513 (2013.01); C12N 2800/80 (2013.01)

(58) Field of Classification Search
None
See application file for complete search history.

(56) References Cited

U.S. PATENT DOCUMENTS

| | | |
|---|---|---|
| 9,512,446 B1 | 12/2016 | Joung et al. |
| 9,637,739 B2 | 5/2017 | Šikšnys et al. |
| 10,844,378 B2 | 11/2020 | Šikšnys et al. |
| 2015/0045546 A1 | 2/2015 | Šikšnys et al. |
| 2015/0050699 A1 | 2/2015 | Šikšnys et al. |
| 2015/0240261 A1 | 8/2015 | Šikšnys et al. |
| 2015/0291961 A1 | 10/2015 | Šikšnys et al. |
| 2016/0312198 A1 | 10/2016 | Joung et al. |
| 2017/0121693 A1 | 5/2017 | Liu et al. |
| 2018/0187195 A1 | 7/2018 | Šikšnys et al. |
| 2018/0312824 A1 | 11/2018 | Zhang et al. |
| 2019/0085329 A1 | 3/2019 | Šikšnys et al. |

FOREIGN PATENT DOCUMENTS

| | | |
|---|---|---|
| JP | 2015-510778 A | 4/2015 |
| WO | WO 2014/093661 A1 | 6/2014 |
| WO | WO 2016/141224 A1 | 9/2016 |
| WO | WO 2016/205759 A1 | 12/2016 |
| WO | WO 2017/010543 A1 | 1/2017 |
| WO | WO 2017/040348 A1 | 3/2017 |
| WO | WO 2017/070633 A2 | 4/2017 |

OTHER PUBLICATIONS

International Search Report and Written Opinion issued Dec. 4, 2018 in PCT/JP2018/032948, 9 pages.
Extended European Search Report issued May 12, 2021 in corresponding European Patent Application No. 18853529.8, 9 pages.
Nishimasu, Hiroshi et al., "Crystal Structure of *Staphylococcus aureus* Cas9", Cell, vol. 162, No. 5, XP055304450, Aug. 27, 2015, pp. 1113-1126.
Kleinstiver. Benjamin et al., "Engineered CRISPR-Cas 9 nucleases with altered PAM specificities", Nature, vol. 523, No. 7561, 2015, pp. 481-485.
Nureki, Osamu et al., "Structure-based development of CRISPR genome-editing tool", Experimental medicine, 2016, vol. 34, No. 20, pp. 3276-3286.
Nureki, Osamu, "Structure-based development of a CRISPR-Cas9 genome editing tool", Bioscience & industry, vol. 75, No. 2, Mar. 2017, pp. 104-113.

(Continued)

*Primary Examiner* — Suzanne M Noakes
*Assistant Examiner* — Jae W Lee
(74) *Attorney, Agent, or Firm* — Oblon, McClelland, Maier & Neustadt, L.L.P.

(57) ABSTRACT

A mutant SaCas9 protein such as a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), arginine at the 991-position to alanine (R991A), alanine at the 1021-position to serine (A1021S), threonine at the 927-position to lysine (T927K), lysine at the 929-position to asparagine (K929N), and isoleucine at the 1017-position to phenylalanine (I1017F) in SEQ ID NO: 2 has relaxed restriction on target sequence while maintaining binding ability to guide RNA, and is useful as a tool for gene editing.

15 Claims, 17 Drawing Sheets

Specification includes a Sequence Listing.

(56) References Cited

OTHER PUBLICATIONS

Ran, F.A et al., "Double Nicking by RNA-Guided CRISPR Cas9 for Enhanced Genome Editing Specificity", Cell, vol. 154, No. 6, 2013, pp. 1380-1389.

Ran, F.A., et al., "In vivo genome editing using *Staphylococcus aureus* Cas9", Nature, vol. 520, No. 7546, 2015, pp. 186-191.

HPRT-AAA

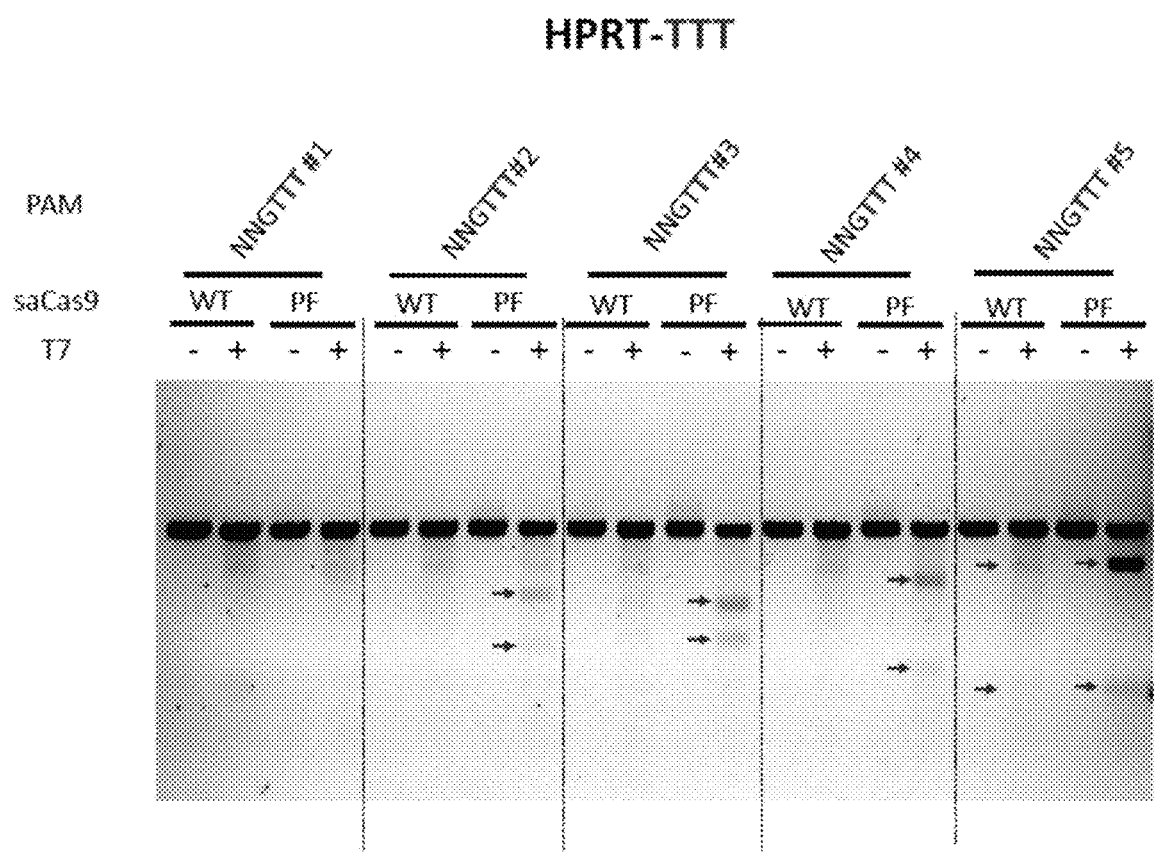
Fig. 5-B

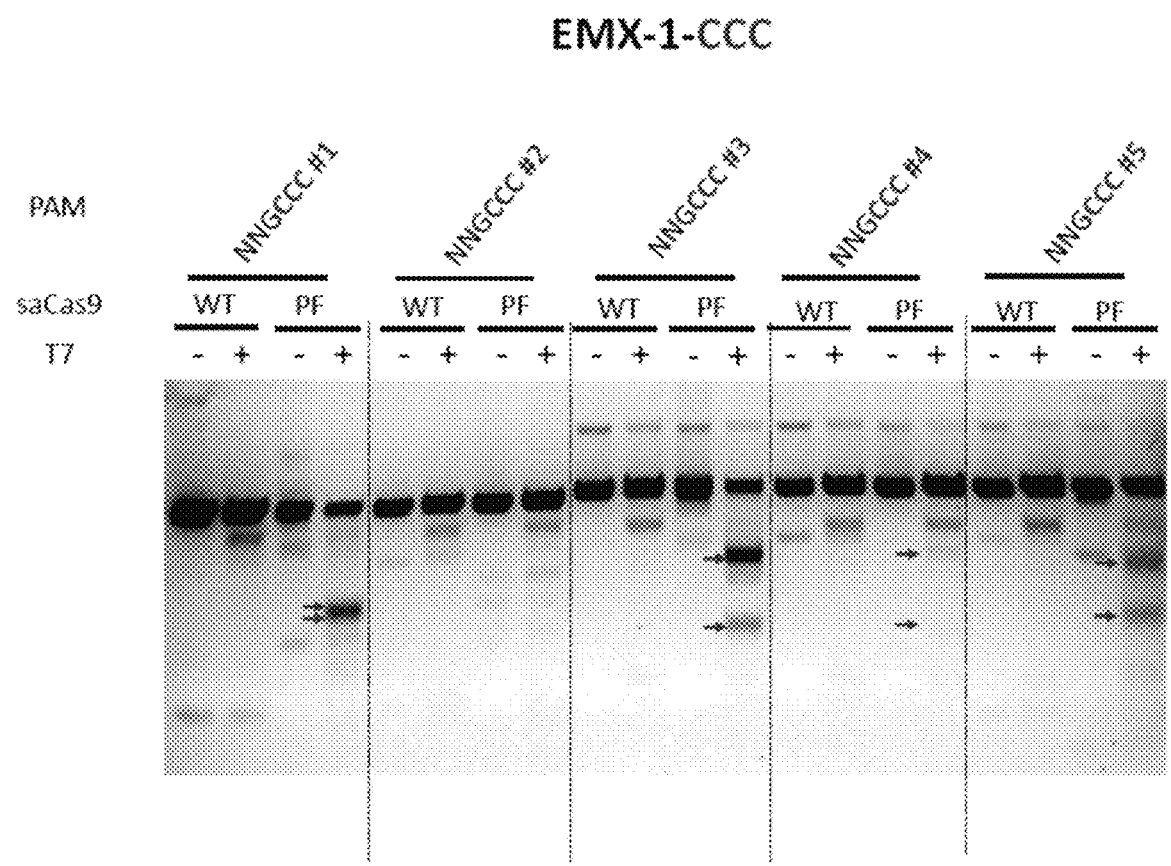

Fig. 6A

WT-dSaCas9-KRAB
NLS-WT-dSaCas9(D10A, N580A)-NLS-KRAB-P2A-Puro fusion protein sequence:

NLS        dsaCas9 (original)           KRAB-P2A-Puro
MAPKKKRKVGIHGVPAAKRNYILGLAIGITSVGYGIIDYETRDVIDAGVRLFKEANVENNEGRRSKR
GARRLKRRRRHRIQRVKKLLFDYNLLTDHSELSGINPYEARVKGLSQKLSEEEFSAALLHLAKRRGVH
NVNEVEEDTGNELSTKEQISRNSKALEEKYVAELQLERLKKDGEVRGSINRFKTSDYVKEAKQLLKV
QKAYHQLDQSFIDTYIDLLETRRTYYEGPGEGSPFGWKDIKEWYEMLMGHCTYFPEELRSVKYAYN
ADLYNALNDLNNLVITRDENEKLEYYEKFQIIENVFKQKKKPTLKQIAKEILVNEEDIKGYRVTSTGKP
EFTNLKVYHDIKDITARKEIIENAELLDQIAKILTIYQSSEDIQEELTNLNSELTQEEIEQISNLKGYTGTH
NLSLKAINLILDELWHTNDNQIAIFNRLKLVPKKVDLSQQKEIPTTLVDDFILSPVVKRSFIQSIKVINAI
IKKYGLPNDIIIELAREKNSKDAQKMINEMQKRNRQTNERIEEIIRTTGKENAKYLIEKIKLHDMQEG
KCLYSLEAIPLEDLLNNPFNYEVDHIIPRSVSFDNSFNNKVLVKQEEASKKGNRTPFQYLSSSDSKISY
ETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFE
EKQAESMPEIETEQEYKEIFITPHQIKHIKDFKDYKYSHRVDKKPNRELINDTLYSTRKDDKGNTLIVN
NLNGLYDKDNDKLKKLINKSPEKLLMYHHDPQTYQKLKLIMEQYGDEKNPLYKYYEETGNYLTKYS
KKDNGPVIKKIKYYGNKLNAHLDITDDYPNSRNKVVKLSLKPYRFDVYLDNGVYKFVTVKNLDVIKK
ENYYEVNSKCYEEAKKLKKISNQAEFIASFYNNDLIKINGELYRVIGVNNDLLNRIEVNMIDITYREYL
ENMNDKRPPRIIKTIASKTQSIKKYSTDILGNLYEVKSKKHPQIIKKGKRPAATKKAGQAKKKKGSM
DAKSLTAWSRTLVTFKDVFVDFTREEWKLLDTAQQIVYRNVMLENYKNLVSLGYQLTKPDVILRLE
KGEEPGSGATNFSLLKQAGDVEENPGPTEYKPTVRLATRDDVPRAVRTLAAAFADYPATRHTVDP
DRHIERVTELQELFLTRVGLDIGKVWVADDGAAVAVWTTPESVEAGAVFAEIGPRMAELSGSRLA
AQQQMEGLLAPHRPKEPAWFLATVGVSPDHQGKGLGSAVVLPGVEAAERAGVPAFLETSAPRN
LPFYERLGFTVTADVEVPEGPRTWCMTRKPGA

Fig. 6B

WT-dSaCas9-KRAB
NLS-WT-dSaCas9(D10A, N580A)-NLS-KRAB-P2A-Puro DNA sequence:

NLS | dsaCas9 (original) | KRAB-P2A-Puro

```
ATGGCCCCAAAGAAGAAGCGGAAGGTCGGTATCCACGGAGTCCCAGCAGCCAAGCGGAACTACATCCTGGGCCTGGCCATCG
GCATCACCAGCGTGGGCTACGGCATCATCGACTACGAGACACGGGACGTGATCGATGCCGGCGTGCGGCTGTTCAAAGAGGCC
AACGTGGAAAACAACGAGGGCAGGCGGAGCAAGAGAGGCGCCAGAAGGCTGAAGCGGCGGAGGCGGCATAGAATCCAGAG
AGTGAAGAAGCTGCTGTTCGACTACAACCTGCTGACCGACCACAGCGAGCTGAGCGGCATCAACCCCTACGAGGCCAGAGTGA
AGGGCCTGAGCCAGAAGCTGAGCGAGGAAGAGTTCTCTGCCGCCCTGCTGCACCTGGCCAAGAGAAGAGGCGTGCACAACGT
GAACGAGGTGGAAGAGGACACCGGCAACGAGCTGTCCACCAAAGAGCAGATCAGCCGGAACAGCAAGGCCCTGGAAGAGAA
ATACGTGGCCGAACTGCAGCTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCTTCATCGACACCTACATCGA
CCTGCTGGAAACCCGGCGGACCTACTATGAGGGACCTGGCGAGGGCAGCCCCTTCGGCTGGAAGGACATCAAAGAATGGTAC
GAGATGCTGATGGGCCACTGCACCTACTTCCCCGAGGAACTGCGGAGCGTGAAGTACGCCTACAACGCCGACCTGTACAACGC
CCTGAACGACCTGAACAATCTCGTGATCACCAGGGACGAGAACGAGAAGCTGGAATATTACGAGAAGTTCCAGATCATCGAGA
ACGTGTTCAAGCAGAAGAAGAAGCCCACCCTGAAGCAGATCGCCAAAGAAATCCTCGTGAACGAAGAGGATATTAAGGGCTAC
AGAGTGACCAGCACCGGCAAGCCCGAGTTCACCAACCTGAAGGTGTACCACGACATCAAGGACATTACCGCCCGGAAAGAGAT
TATTGAGAACGCCGAGCTGCTGGATCAGATTGCCAAGATCCTGACCATCTACCAGAGCAGCGAGGACATCCAGGAAGAACTGA
CCAATCTGAACTCCGAGCTGACCCAGGAAGAGATCGAGCAGATCTCTAATCTGAAGGGCTATACCGGCACCCACAACCTGAGCC
TGAAGGCCATCAACCTGATCCTGGACGAGCTGTGGCACACCAACGACAACCAGATCGCTATCTTCAACCGGCTGAAGCTGGTGC
CCAAGAAGGTGGACCTGTCCCAGCAGAAAGAGATCCCCACCACCCTGGTGGACGACTTCATCCTGAGCCCCGTCGTGAAGAGA
AGCTTCATCCAGAGCATCAAAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACCAACGAGCGGATCGAGGAA
ATCATCCGGACCACCGGCAAAGAGAACGCCAAGTACCTGATCGAGAAGATCAAGCTGCACGACATGCAGGAAGGCAAGTGCCT
GTACAGCCTGGAAGCCATCCCTCTGGAAGATCTGCTGAACAACCCCTTCAACTATGAGGTGGACCACATCATCCCCAGAAGCGT
GTCCTTCGACAACAGCTTCAACAACAAGGTGCTCGTGAAGCAGGAAGAAGCCAGCAAGAAGGGCAACCGGACCCCATTCCAGT
ACCTGAGCAGCAGCGACAGCAAGATCAGCTACGAAACCTTCAAGAAGCACATCCTGAATCTGGCCAAGGGCAAGGGCAGAATC
AGCAAGACCAAGAAAGAGTATCTGCTGGAAGAACGGGACATCAACAGGTTCTCCGTGCAGAAAGACTTCATCAACCGGAACCT
GGTGGATACCAGATACGCCACCAGAGGCCTGATGAACCTGCTGCGGAGCTACTTCAGAGTGAACAACCTGGACGTGAAAGTGA
AGTCCATCAATGGCGGCTTCACCAGCTTTCTGCGGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTGGAAGAAACTGGACAAGGCCAAAAAAGTGATGGA
AAACCAGATGTTCGAGGAAAAGCAGGCCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGTGGACAAGAAGCCTAATAGAGAGCTGAT
TAACGACACCCTGTACTCCACCCGGAAGGACGACAAGGGCAACACCCTGATCGTGAACAATCTGAACGGCCTGTACGACAAGG
ACAATGACAAGCTGAAAAAGCTGATCAACAAGAGCCCCGAAAAGCTGCTGATGTACCACCACGACCCCCAGACCTACCAGAAA
CTGAAGCTGATTATGGAACAGTACGGCGACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACAAACTGAACGCCCATCTGGACATCACCG
ACGACTACCCCAACAGCAGAAACAAGGTCGTGAAGCTGTCCCTGAAGCCCTACAGATTCGACGTGTACCTGGACAATGGCGTGT
ACAAGTTCGTGACCGTGAAGAATCTGGATGTGATCAAAAAAGAAAACTACTACGAAGTGAATAGCAAGTGCTATGAGGAAGCT
AAGAAGCTGAAGAAGATCAGCAACCAGGCCGAGTTTATCGCCTCCTTCTACAACAACGATCTGATCAAGATCAACGGCGAGCTG
TATAGAGTGATCGGCGTGAACAACGACCTGCTGAACCGGATCGAAGTGAACATGATCGACATCACCTACCGCGAGTACCTGGA
AAACATGAACGACAAGAGGCCCCCAGGATCATTAAGACAATCGCCTCCAAGACCCAGAGCATTAAGAAGTACAGCACAGACA
TTCTGGGCAACCTGTATGAAGTGAAATCTAAGAAGCACCCTCAGATCATCAAAAAGGGCAAAAGGCCGGCGGCCACGAAAAA
GGCCGGCCAGGCAAAAAAGAAAAAGGGATCCATGGATGCTAAGTCACTAACTGCCTGGTCCCGGACACTGGTGACCTTCAAG
GATGTATTTGTGGACTTCACCAGGGAGGAGTGGAAGCTGCTGGACACTGCTCAGCAGATCGTGTACAGAAATGTGATGCTGGA
GAACTATAAGAACCTGGTTTCCTTGGGTTATCAGCTTACTAAGCCAGATGTGATCCTCCGGTTGGAGAAGGGAGAAGAGCCCG
GAAGCGGTGCTACTAACTTCAGCCTGCTGAAGCAGGCTGGAGACGTGGAGGAGAACCCTGGACCTACCGAGTACAAGCCACG
GTGCGCCTCGCCACCCGCGACGACGTCCCCAGGGCCGTACGCACCCTCGCCGCCGCGTTCGCCGACTACCCCGCCACGCGCCAC
ACCGTCGATCCGGACCGCCACATCGAGCGGGTCACCGAGCTGCAAGAACTCTTCCTCACGCGCGTCGGGCTCGACATCGGCAA
GGTGTGGGTCGCGGACGACGGCGCCGCGGTGGCGGTCTGGACCACGCCGGAGAGCGTCGAAGCGGGGGCGGTGTTCGCCGA
GATCGGCCCGCGCATGGCCGAGTTGAGCGGTTCCGGCTGGCCGCGCAGCAACAGATGGAAGGCCTCCTGGCGCCGCACCGG
CCCAAGGAGCCCGCGTGGTTCCTGGCCACCGTCGGAGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAAACCTCCGCGCCCGCAACCTCCCCTTCTACGAGC
GGCTCGGCTTCACCGTCACCGCCGACGTCGAGGTGCCCGAAGGACCGCGCACCTGGTGCATGACCCGCAAGCCCGGTGCCTGA
```

Fig. 7A

PF(v15)-dSaCas9-KRAB
NLS-PF(v15)-dSaCas9(D10A, N580A)-NLS-KRAB-P2A-Puro fusion protein sequence:

NLS        dsaCas9 (v15)              KRAB-P2A-Puro
MAPKKKRKVGIHGVPAAKRNYILGLAIGITSVGYGIIDYETRDVIDAGVRLFKEANVENNEGRRSKR
GARRLKRRRRHRIQRVKKLLFDYNLLTDHSELSGINPYEARVKGLSQKLSEEEFSAALLHLAKRRGVH
NVNEVEEDTGNELSTKEQISRNSKALEEKYVAELQLERLKKDGEVRGSINRFKTSDYVKEAKQLLKV
QKAYHQLDQSFIDTYIDLLETRRTYYEGPGEGSPFGWKDIKEWYEMLGHCTYFPEELRSVKYAYN
ADLYNALNDLNNLVITRDENEKLEYYEKFQIENVFKQKKKPTLKQIAKEILVNEEDIKGYRVTSTGKP
EFTNLKVYHDIKDITARKEIIENAELLDQIAKILTIYQSSEDIQEELTNLNSELTQEEIEQISNLKGYTGTH
NLSLKAINLILDELWHTNDNQIAIFNRLKLVPKKVDLSQQKEIPTTLVDDFILSPVVKRSFIQSIKVINAI
IKKYGLPNDIIIELAREKNSKDAQKMINEMQKRNRQTNERIEEIRTTGKENAKYLIEKIKLHDMQEG
KCLYSLEAIPLEDLLNNPFNYEVDHIIPRSVSFDNSFNNKVLVKQEEASKKGNRTPFQYLSSSDSKISY
ETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFE
EKQAESMPEIETEQEYKEIFITPHQIKHIKDFKDYKYSHRVDKKPNRKLINDTLYSTRKDDKGNTRIV
NNLNGLYDKDNDKLKKLINKSPEKLLMYHHDPQTYQKLKLIMEQYGDEKNPLYKYYEETGNYLTKY
SKKDNGPVIKKIKYYGNKLNRHLDITDDYPNSRNKVVKLSLKPYRFDVYLDNGVYKFVTVKNLDVIK
KENYYEVNSKCYEEAKKLKKISNQAEFIASFYRNDLIKINGELYRVIGVAADHLNAIEVNMIDITYREY
LENMNDKRPPRIIKTISSKTQSIKKYSTDILGNLYEVKSKKHPQIIKKGKRPAATKKAGQAKKKKGSM
DAKSLTAWSRTLVTFKDVFVDFTREEWKLLDTAQQIVYRNVMLENYKNLVSLGYQLTKPDVILRLE
KGEEPGSGATNFSLLKQAGDVEENPGPTEYKPTVRLATRDDVPRAVRTLAAAFADYPATRHTVDP
DRHIERVTELQELFLTRVGLDIGKVWVADDGAAVAVWTTPESVEAGAVFAEIGPRMAELSGSRLA
AQQQMEGLLAPHRPKEPAWFLATVGVSPDHQGKGLGSAVVLPGVEAAERAGVPAFLETSAPRN
LPFYERLGFTVADVEVPEGPRTWCMTRKPGA

Fig. 7B

PF(v15)-dSaCas9-KRAB
NLS-PF(v15)-dSaCas9(D10A, N580A)-NLS-KRAB-P2A-Puro DNA sequence:

```
NLS        dsaCas9 (v15)           KRAB-P2A-Puro
ATGGCCCCAAAGAAGAAGCGGAAGGTCGGTATCCACGGAGTCCCAGCAGCCAAGCGGAACTACATCCTGGGCCTGGCCATCG
GCATCACCAGCGTGGGCTACGGCATCATCGACTACGAGACACGGGACGTGATCGATGCCGGCGTGCGGCTGTTCAAAGAGGCC
AACGTGGAAAACAACGAGGGCAGGCGGAGCAAGAGAGGCGCCAGAAGGCTGAAGCGGCGGAGGCGGCATAGAATCCAGAG
AGTGAAGAAGCTGCTGTTCGACTACAACCTGCTGACCGACCACAGCGAGCTGAGCGGCATCAACCCCTACGAGGCCAGAGTGA
AGGGCCTGAGCCAGAAGCTGAGCGAGGAAGAGTTCTCTGCCGCCCTGCTGCACCTGGCCAAGAGAAGAGGCGTGCACAACGT
GAACGAGGTGGAAGAGGACACCGGCAACGAGCTGTCCACCAAAGAGCAGATCAGCCGGAACAGCAAGGCCCTGGAAGAGAA
ATACGTGGCCGAACTGCAGCTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCTTCATCGACACCTACATCGA
CCTGCTGGAAACCCGGCGGACCTACTATGAGGGACCTGGCGAGGGCAGCCCCTTCGGCTGGAAGGACATCAAAGAATGGTAC
GAGATGCTGATGGGCCACTGCACCTACTTCCCCGAGGAACTGCGGAGCGTGAAGTACGCCTACAACGCCGACCTGTACAACGC
CCTGAACGACCTGAACAATCTCGTGATCACCAGGGACGAGAACGAGAAGCTGGAATATTACGAGAAGTTCCAGATCATCGAGA
ACGTGTTCAAGCAGAAGAAGAAGCCCACCCTGAAGCAGATCGCCAAAGAAATCCTCGTGAACGAAGAGGATATTAAGGGCTAC
AGAGTGACCAGCACCGGCAAGCCCGAGTTCACCAACCTGAAGGTGTACCACGACATCAAGGACATTACCGCCCGGAAAGAGAT
TATTGAGAACGCCGAGCTGCTGGATCAGATTGCCAAGATCCTGACCATCTACCAGAGCAGCGAGGACATCCAGGAAGAACTGA
CCAATCTGAACTCCGAGCTGACCCAGGAAGAGATCGAGCAGATCTCTAATCTGAAGGGCTATACCGGCACCCACAACCTGAGCC
TGAAGGCCATCAACCTGATCCTGGACGAGCTGTGGCACACCAACGACAACCAGATCGCTATCTTCAACCGGCTGAAGCTGGTGC
CAAGAAGGTGGACCTGTCCCAGCAGAAAGAGATCCCCACCACCCTGGTGGACGACTTCATCCTGAGCCCCGTCGTGAAGAGA
AGCTTCATCCAGAGCATCAAAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACCAACGAGCGGATCGAGGAA
ATCATCCGGACCACCGGCAAAGAGAACGCCAAGTACCTGATCGAGAAGATCAAGCTGCACGACATGCAGGAAGGCAAGTGCCT
GTACAGCCTGGAAGCCATCCCTCTGGAAGATCTGCTGAACAACCCCTTCAACTATGAGGTGGACCACATCATCCCCAGAAGCGT
GTCCTTCGACAACAGCTTCAACAACAAGGTGCTCGTGAAGCAGGAAGAAGCCAGCAAGAAGGGCAACCGGACCCCATTCCAGT
ACCTGAGCAGCAGCGACAGCAAGATCAGCTACGAAACCTTCAAGAAGCACATCCTGAATCTGGCCAAGGGCAAGGGCAGAATC
AGCAAGACCAAGAAAGAGTATCTGCTGGAAGAACGGGACATCAACAGGTTCTCCGTGCAGAAAGACTTCATCAACCGGAACCT
GGTGGATACCAGATACGCCACCAGAGGCCTGATGAACCTGCTGCGGAGCTACTTCAGAGTGAACAACCTGGACGTGAAAGTGA
AGTCCATCAATGGCGGCTTCACCAGCTTTCTGCGGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTGGAAGAAACTGGACAAGGCCAAAAAAGTGATGGA
AAACCAGATGTTCGAGGAAAAGCAGGCCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGTGGACAAGAAGCCTAATAGAAAGCTGAT
TAACGACACCCTGTACTCCACCCGGAAGGACGACAAGGGCAACACCCGGATCGTGAACAATCTGAACGGCCTGTACGACAAGG
ACAATGACAAGCTGAAAAAGCTGATCAACAAGAGCCCCGAAAAGCTGCTGATGTACCACCACGACCCCCAGACCTACCAGAAA
CTGAAGCTGATTATGGAACAGTACGGCGACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACAAACTGAACAGACATCTGGACATCACCG
ACGACTACCCCAACAGCAGAAACAAGGTCGTGAAGCTGTCCCTGAAGCCCTACAGATTCGACGTGTACCTGGACAATGGCGTGT
ACAAGTTCGTGACCGTGAAGAATCTGGATGTGATCAAAAAAGAAAACTACTACGAAGTGAATAGCAAGTGCTATGAGGAAGCT
AAGAAGCTGAAGAAGATCAGCAACCAGGCCGAGTTTATCGCCTCCTTCTACAGAAACGATCTGATCAAGATCAACGGCGAGCT
GTATAGAGTGATCGGCGTGGCGGCCGACCACCTGAACGCCATCGAAGTGAACATGATCGACATCACCTACCGCGAGTACCTGG
AAAACATGAACGACAAGAGGCCCCCCAGGATCATTAAGACAATCAGCTCCAAGACCCAGAGCATTAAGAAGTACAGCACAGAC
ATTCTGGGCAACCTGTATGAAGTGAAATCTAAGAAGCACCCTCAGATCATCAAAAAGGGCAAAAGGCCGGCGGCCACGAAAAA
GGCCGGCCAGGCAAAAAAGAAAAAGGGATCCATGGATGCTAAGTCACTAACTGCCTGGTCCCGGACACTGGTGACCTTCAAG
GATGTATTTGTGGACTTCACCAGGGAGGAGTGGAAGCTGCTGGACACTGCTCAGCAGATCGTGTACAGAAATGTGATGCTGGA
GAACTATAAGAACCTGGTTTCCTTGGGTTATCAGCTTACTAAGCCAGATGTGATCCTCCGGTTGGAGAAGGGAGAAGAGCCCG
GAAGCGGTGCTACTAACTTCAGCCTGCTGAAGCAGGCTGGAGACGTGGAGGAGAACCCTGGACCCGAGTACAAGCCCACG
GTGCGCCTCGCCACCCGCGACGTCCCCAGGGCCGTACGCACCCTCGCCGCCGCGTTCGCCGACTACCCCGCCACGCGCCAC
ACCGTCGATCCGGACCGCCACATCGAGCGGGTCACCGAGCTGCAAGAACTCTTCCTCACGCGCGTCGGGCTCGACATCGGCAA
GGTGTGGGTCGCGGACGACGGCGCCGCGGTGGCGGTCTGGACCACGCCGGAGAGCGTCGAAGCGGGGGCGGTGTTCGCCGA
GATCGGCCCGCGCATGGCCGAGTTGAGCGGTTCCCGGCTGGCCGCGCAGCAACAGATGGAAGGCCTCCTGGCGCCGCACCGG
CCCAAGGAGCCCGCGTGGTTCCTGGCCACCGTCGGAGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAAACCTCCGCGCCCCGCAACCTCCCCTTCTACGAGC
GGCTCGGCTTCACCGTCACCGCCGACGTCGAGGTGCCCGAAGGACCGCGCACCCTGGTGCATGACCCGCAAGCCCGGTGCCTGA
```

Fig. 8A

PF(v51)-dSaCas9-KRAB
NLS-PF(v51)-dSaCas9(D10A, N580A)-NLS-KRAB-P2A-Puro fusion protein sequence:

NLS        dsaCas9 (v51)               KRAB-P2A-Puro
MAPKKKRKVGIHGVPAAKRNYILGLAIGITSVGYGIIDYETRDVIDAGVRLFKEANVENNEGRRSKR
GARRLKRRRRHRIQRVKKLLFDYNLLTDHSELSGINPYEARVKGLSQKLSEEEFSAALLHLAKRRGVH
NVNEVEEDTGNELSTKEQISRNSKALEEKYVAELQLERLKKDGEVRGSINRFKTSDYVKEAKQLLKV
QKAYHQLDQSFIDTYIDLLETRRTYYEGPGEGSPFGWKDIKEWYEMLMGHCTYFPEELRSVKYAYN
ADLYNALNDLNNLVITRDENEKLEYYEKFQIIENVFKQKKKPTLKQIAKEILVNEEDIKGYRVTSTGKP
EFTNLKVYHDIKDITARKEIIENAELLDQIAKILTIYQSSEDIQEELTNLNSELTQEEIEQISNLKGYTGTH
NLSLKAINLILDELWHTNDNQIAIFNRLKLVPKKVDLSQQKEIPTTLVDDFILSPVVKRSFIQSIKVINAI
IKKYGLPNDIIIELAREKNSKDAQKMINEMQKRNRQTNERIEEIIRTTGKENAKYLIEKIKLHDMQEG
KCLYSLEAIPLEDLLNNPFNYEVDHIIPRSVSFDNSFNNKVLVKQEEASKKGNRTPFQYLSSSDSKISY
ETFKKHILNLAKGKGRISKTKKEYLLEERDINRFSVQKDFINRNLVDTRYATRGLMNLLRSYFRVNNL
DVKVKSINGGFTSFLRRKWKFKKERNKGYKHHAEDALIIANADFIFKEWKKLDKAKKVMENQMFE
EKQAESMPEIETEQEYKEIFITPHQIKHIKDFKDYKYSHRVDKKPNRKLINDTLYSTRKDDKGNTRIV
NNLNGLYDKDNDKLKKLINKSPEKLLMYHHDPQTYQKLKLIMEQYGDEKNPLYKYYEETGNYLTKY
SKKDNGPVIKKIKYYGNKLNAHLDITDDYPNSRNKVVKLSLKPYRFDVYLDNGVYKFVKVNNLDVIK
KENYYEVNSKCYEEAKKLKKISNQAEFIASFYRNDLIKINGELYRVIGVANDLLNAIEVNMIDITYREYL
ENMNDKRPPRIFKTISSKTQSIKKYSTDILGNLYEVKSKKHPQIIKKGKRPAATKKAGQAKKKKGSM
DAKSLTAWSRTLVTFKDVFVDFTREEWKLLDTAQQIVYRNVMLENYKNLVSLGYQLTKPDVILRLE
KGEEPGSGATNFSLLKQAGDVEENPGPTEYKPTVRLATRDDVPRAVRTLAAAFADYPATRHTVDP
DRHIERVTELQELFLTRVGLDIGKVWVADDGAAVAVWTTPESVEAGAVFAEIGPRMAELSGSRLA
AQQQMEGLLAPHRPKEPAWFLATVGVSPDHQGKGLGSAVVLPGVEAAERAGVPAFLETSAPRN
LPFYERLGFTVTADVEVPEGPRTWCMTRKPGA

Fig. 8B

PF(v51)-dSaCas9-KRAB

NLS-PF(v51)-dSaCas9(D10A, N580A)-NLS-KRAB-P2A-Puro DNA sequence:

NLS    dsaCas9 (v51)    KRAB-P2A-Puro

```
ATGGCCCCAAAGAAGAAGCGGAAGGTCGGTATCCACGGAGTCCCAGCAGCCAAGCGGAACTACATCCTGGGCCTGGCCATCG
GCATCACCAGCGTGGGCTACGGCATCATCGACTACGAGACACGGGACGTGATCGATGCCGGCGTGCGGCTGTTCAAAGAGGCC
AACGTGGAAAACAACGAGGGCAGGCGGAGCAAGAGAGGCGCCAGAAGGCTGAAGCGGCGGAGGCGGCATAGAATCCAGAG
AGTGAAGAAGCTGCTGTTCGACTACAACCTGCTGACCGACCACAGCGAGCTGAGCGGCATCAACCCCTACGAGGCCAGAGTGA
AGGGCCTGAGCCAGAAGCTGAGCGAGGAAGAGTTCTCTGCCGCCCTGCTGCACCTGGCCAAGAGAAGAGGCGTGCACAACGT
GAACGAGGTGGAAGAGGACACCGGCAACGAGCTGTCCACCAAAGAGCAGATCAGCCGGAACAGCAAGGCCCTGGAAGAGAA
ATACGTGGCCGAACTGCAGCTGGAACGGCTGAAGAAAGACGGCGAAGTGCGGGGCAGCATCAACAGATTCAAGACCAGCGAC
TACGTGAAAGAAGCCAAACAGCTGCTGAAGGTGCAGAAGGCCTACCACCAGCTGGACCAGAGCTTCATCGACACCTACATCGA
CCTGCTGGAAACCCGGCGGACCTACTATGAGGGACCTGGCGAGGGCAGCCCCTTCGGCTGGAAGGACATCAAAGAATGGTAC
GAGATGCTGATGGGCCACTGCACCTACTTCCCCGAGGAACTGCGGAGCGTGAAGTACGCCTACAACGCCGACCTGTACAACGC
CCTGAACGACCTGAACAATCTCGTGATCACCAGGGACGAGAACGAGAAGCTGGAATATTACGAGAAGTTCCAGATCATCGAGA
ACGTGTTCAAGCAGAAGAAGAAGCCCACCCTGAAGCAGATCGCCAAAGAAATCCTCGTGAACGAAGAGGATATTAAGGGCTAC
AGAGTGACCAGCACCGGCAAGCCCGAGTTCACCAACCTGAAGGTGTACCACGACATCAAGGACATTACCGCCCGGAAAGAGAT
TATTGAGAACGCCGAGCTGCTGGATCAGATTGCCAAGATCCTGACCATCTACCAGAGCAGCGAGGACATCCAGGAAGAACTGA
CCAATCTGAACTCCGAGCTGACCCAGGAAGAGATCGAGCAGATCTCTAATCTGAAGGGCTATACCGGCACCCACAACCTGAGCC
TGAAGGCCATCAACCTGATCCTGGACGAGCTGTGGCACACCAACGACAACCAGATCGCTATCTTCAACCGGCTGAAGCTGGTGC
CCAAGAAGGTGGACCTGTCCCAGCAGAAAGAGATCCCCACCACCCTGGTGGACGACTTCATCCTGAGCCCCGTCGTGAAGAGA
AGCTTCATCCAGAGCATCAAAGTGATCAACGCCATCATCAAGAAGTACGGCCTGCCCAACGACATCATTATCGAGCTGGCCCGC
GAGAAGAACTCCAAGGACGCCCAGAAAATGATCAACGAGATGCAGAAGCGGAACCGGCAGACCAACGAGCGGATCGAGGAA
ATCATCCGGACCACCGGCAAAGAGAACGCCAAGTACCTGATCGAGAAGATCAAGCTGCACGACATGCAGGAAGGCAAGTGCCT
GTACAGCCTGGAAGCCATCCCTCTGGAAGATCTGCTGAACAACCCCTTCAACTATGAGGTGGACCACATCATCCCCAGAAGCGT
GTCCTTCGACAACAGCTTCAACAACAAGGTGCTCGTGAAGCAGGAAGAAGCCAGCAAGAAGGGCAACCGGACCCCATTCCAGT
ACCTGAGCAGCAGCGACAGCAAGATCAGCTACGAAACCTTCAAGAAGCACATCCTGAATCTGGCCAAGGGCAAGGGCAGAATC
AGCAAGACCAAGAAAGAGTATCTGCTGGAAGAACGGGACATCAACAGGTTCTCCGTGCAGAAAGACTTCATCAACCGGAACCT
GGTGGATACCAGATACGCCACCAGAGGCCTGATGAACCTGCTGCGGAGCTACTTCAGAGTGAACAACCTGGACGTGAAAGTGA
AGTCCATCAATGGCGGCTTCACCAGCTTTCTGCGGCGGAAGTGGAAGTTTAAGAAAGAGCGGAACAAGGGGTACAAGCACCAC
GCCGAGGACGCCCTGATCATTGCCAACGCCGATTTCATCTTCAAAGAGTGGAAGAAACTGGACAAGGCCAAAAAAGTGATGGA
AAACCAGATGTTCGAGGAAAAGCAGGCCGAGAGCATGCCCGAGATCGAAACCGAGCAGGAGTACAAAGAGATCTTCATCACC
CCCCACCAGATCAAGCACATTAAGGACTTCAAGGACTACAAGTACAGCCACCGGGTGGACAAGAAGCCTAATAGAAAACTGAT
TAACGACACCCTGTACTCCACCCGGAAGGACGACAAGGGCAACACCCGGATCGTGAACAATCTGAACGGCCTGTACGACAAGG
ACAATGACAAGCTGAAAAAGCTGATCAACAAGAGCCCCGAAAAGCTGCTGATGTACCACCACGACCCCCAGACCTACCAGAAA
CTGAAGCTGATTATGGAACAGTACGGCGACGAGAAGAATCCCCTGTACAAGTACTACGAGGAAACCGGGAACTACCTGACCAA
GTACTCCAAAAAGGACAACGGCCCCGTGATCAAGAAGATTAAGTATTACGGCAACAAACTGAACGCCCATCTGGACATCACCG
ACGACTACCCCAACAGCAGAAACAAGGTCGTGAAGCTGTCCCTGAAGCCCTACAGATTCGACGTGTACCTGGACAATGGCGTGT
ACAAGTTCGTGAAGGTGAATAATCTGGATGTGATCAAAAAAGAAAACTACTACGAAGTGAATAGCAAGTGCTATGAGGAAGCT
AAGAAGCTGAAGAAGATCAGCAACCAGGCCGAGTTTATCGCCTCCTTCTACAGAAACGATCTGATCAAGATCAACGGCGAGCT
GTATAGAGTGATCGGCGTGGCCAACGACCTGCTGAACGCCATCGAAGTGAACATGATCGACATCACCTACCGCGAGTACCTGG
AAAACATGAACGACAAGAGGCCCCCCAGGATCTTCAAGACAATCTCCTCCAAGACCCAGAGCATTAAGAAGTACAGCACAGAC
ATTCTGGGCAACCTGTATGAAGTGAAATCTAAGAAGCACCCTCAGATCATCAAAAAGGGCAAAAGGCCGGCGGCCACGAAAAA
GGCCGGCCAGGCAAAAAAGAAAAAGGGATCCATGGATGCTAAGTCACTAACTGCCTGGTCCCGGACACTGGTGACCTTCAAG
GATGTATTTGTGGACTTCACCAGGGAGGAGTGGAAGCTGCTGGACACTGCTCAGCAGATCGTGTACAGAAATGTGATGCTGGA
GAACTATAAGAACCTGGTTTCCTTGGGTTATCAGCTTACTAAGCCAGATGTGATCCTCCGGTTGGAGAAGGGAGAAGAGCCCG
GAAGCGGTGCTACTAACTTCAGCCTGCTGAAGCAGGCTGGAGACGTGGAGGAGAACCCTGGACCTACCGAGTACAAGCCACG
GTGCGCCTCGCCACCCGCGACGACGTCCCCAGGGCCGTACGCACCCTCGCCGCCGCGTTCGCCGACTACCCCGCCACGCGCCAC
ACCGTCGATCCGGACCGCCACATCGAGCGGGTCACCGAGCTGCAAGAACTCTTCCTCACGCGCGTCGGGCTCGACATCGGCAA
GGTGTGGGTCGCGGACGACGGCGCCGCGGTGGCGGTCTGGACCACGCCGGAGAGCGTCGAAGCGGGGGCGGTGTTCGCCGA
GATCGGCCCGCGCATGGCCGAGTTGAGCGGTTCCCGGCTGGCCGCGCAGCAACAGATGGAAGGCCTCCTGGCGCCGCACCGG
CCCAAGGAGCCCGCGTGGTTCCTGGCCACCGTCGGAGTCTCGCCCGACCACCAGGGCAAGGGTCTGGGCAGCGCCGTCGTGCT
CCCCGGAGTGGAGGCGGCCGAGCGCGCCGGGGTGCCCGCCTTCCTGGAAACCTCCGCGCCCCGCAACCTCCCCTTCTACGAGC
GGCTCGGCTTCACCGTCACCGCCGACGTCGAGGTGCCCGAAGGACCGCGCACCTGGTGCATGACCCGCAAGCCCGGTGCCTGA
```

Fig. 9
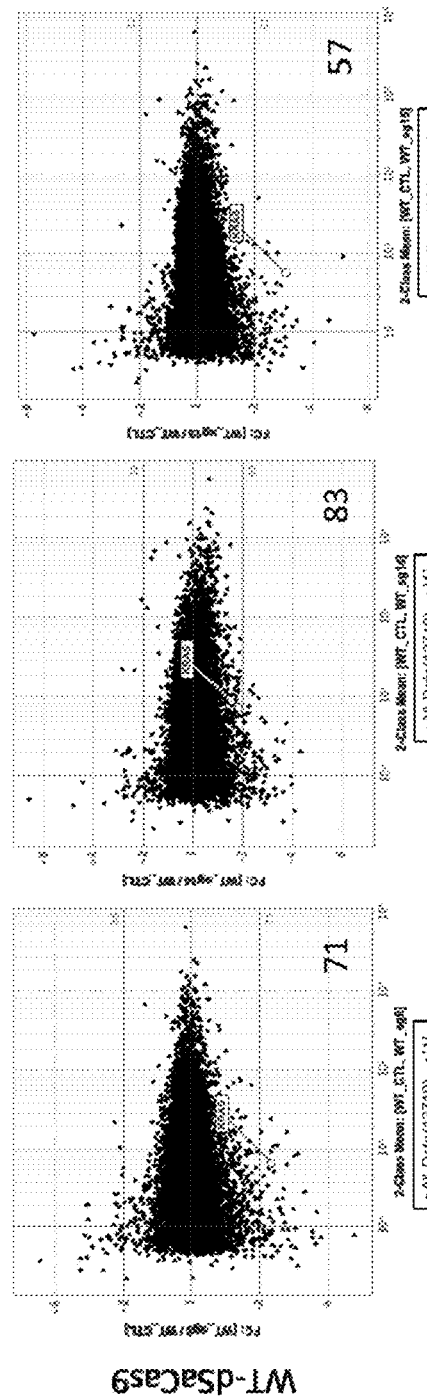
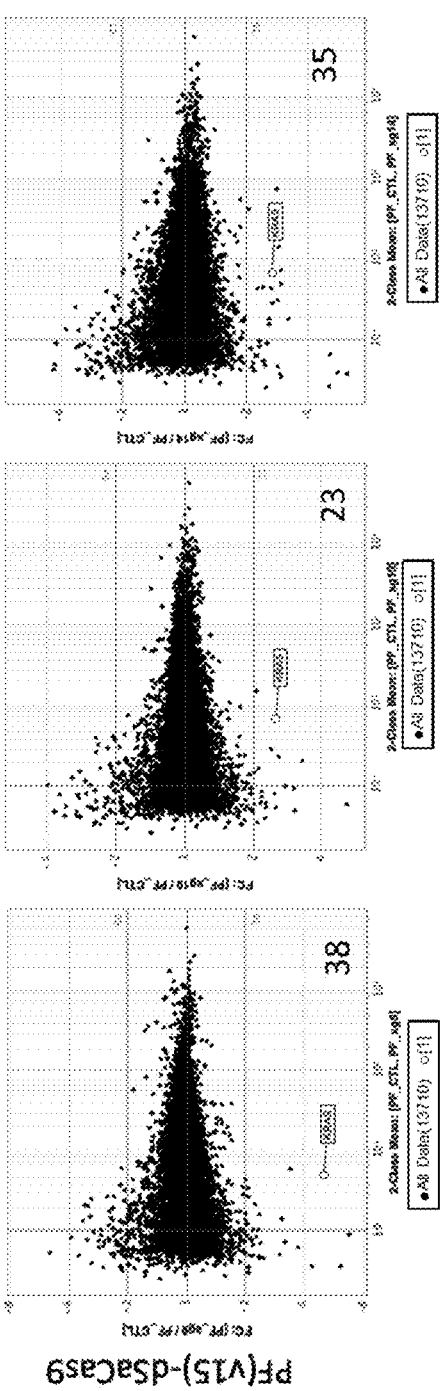

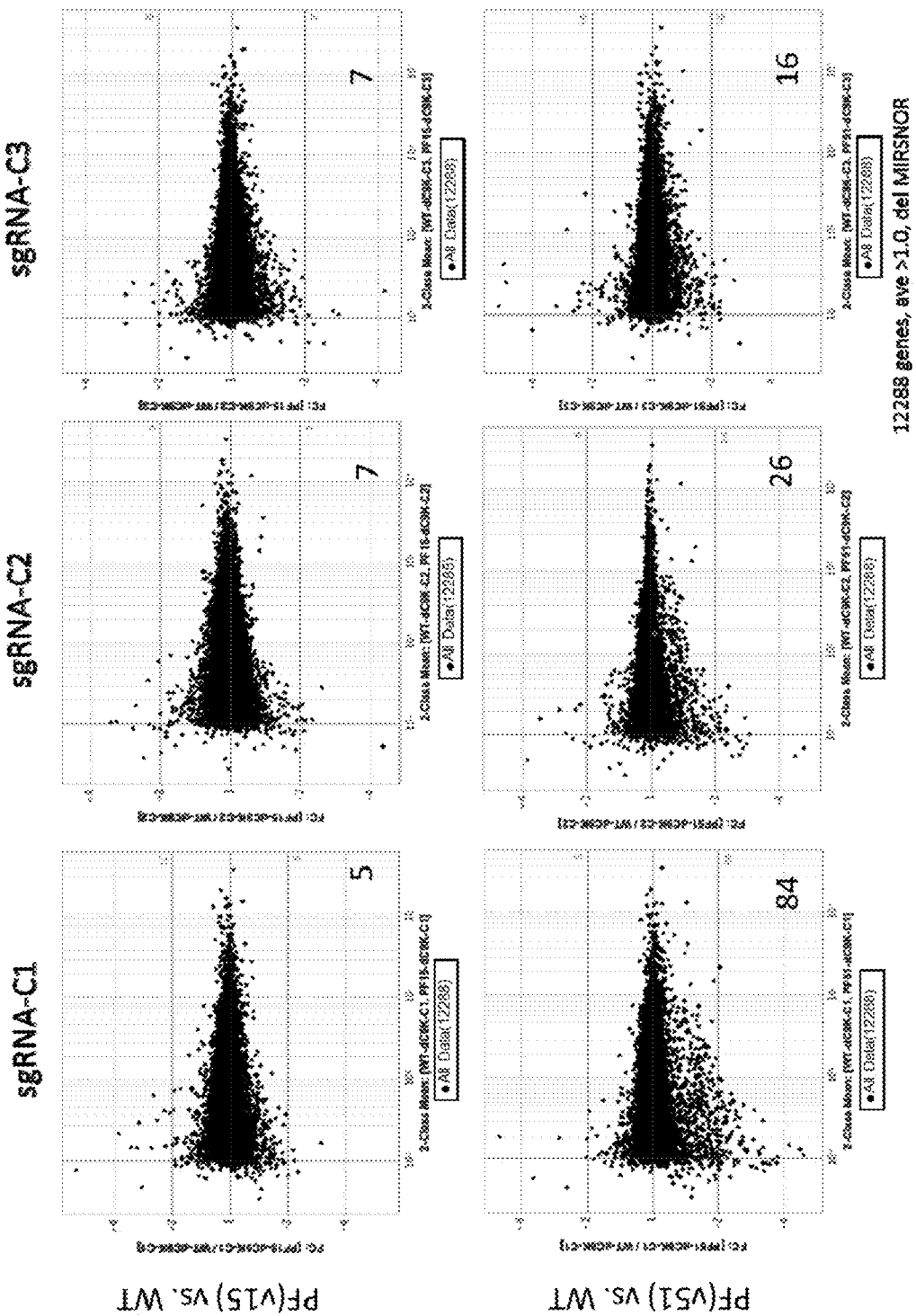

SEQUENCE LISTING

```
Sequence total quantity: 52
SEQ ID NO: 1            moltype = DNA  length = 3162
FEATURE                 Location/Qualifiers
source                  1..3162
                        mol_type = other DNA
                        organism = Staphylococcus aureus
CDS                     1..3162
SEQUENCE: 1
atgaaaagga actacattct ggggctggac atcgggatta caagcgtggg gtatgggatt    60
attgactatg aaacaaggga cgtgatcgac gcaggcgtca gactgttcaa ggaggccaac   120
gtggaaaaca atgagggacg gagaagcaag aggggagcca ggcgcctgaa acgacggaga   180
aggcacagaa tccagagggt gaagaaactg ctgttcgatt acaacctgct gaccgaccat   240
tctgagctga gtggaattaa tccttatgaa gccagggtga aaggcctgag tcagaagctg   300
tcagaggaag agttttccgc agctctgctg cacctggcta agcgccgagg agtgcataac   360
gtcaatgagg tggaagagga caccggcaac gagctgtcta caaaggaaca gatctcacgc   420
aatagcaaag ctctggaaga gaagtatgtc gcagagctgc agctggaacg gctgaagaaa   480
gatggcgagg tgagagggtc aattaatagg ttcaagacaa gcgactacgt caaagaagcc   540
aagcagctgc tgaaagtgca gaaggcttac caccagctgg atcagagctt catcgatact   600
tatatcgacc tgctggagac tcggagaacc tactatgagg gaccaggaga agggagcccc   660
ttcggatgga aagacatcaa ggaatggtac gagatgctga tgggacattg cacctatttt   720
ccagaagagc tgagaagcgt caagtacgct tataacgcag atctgtacaa cgccctgaat   780
gacctgaaca acctggtcat caccagggat gaaaacgaga aactggaata ctatgagaag   840
ttccagatca tcgaaaacgt gtttaagcag aagaaaaagc ctacactgaa acagattgct   900
aaggagatcc tggtcaacga agaggacatc aagggctacc gggtgacaag cactggaaaa   960
ccagagttca ccaatctgaa agtgtatcac gatattaagg acatcacgac acggaaagaa  1020
atcattgaga acgccgaact gctggatcag attgctaaga tcctgactat ctaccagagc  1080
tccgaggaca tccaggaaga gctgactaac ctgaacagcg agctgaccca ggaagagatc  1140
gaacagatta gtaatctgaa ggggtacacc ggaacacaca acctgtccct gaaagctatc  1200
aatctgattc tggatgagct gtggcataca aacgacaatc agattgcaat ctttaaccgg  1260
ctgaagctgg tcccaaaaaa ggtggacctg agtcagcaga aagagatccc aaccacactg  1320
gtggacgatt tcattctgtc acccgtggtc aagcggagct tcatccagag catcaaagtg  1380
atcaacgcca tcatcaagaa gtacggcctg cccaatgata tcattatcga gctggctagg  1440
gagaagaaca gcaaggacgc acagaagatg atcaatgaga tgcagaaacg aaaccggcag  1500
accaatgaac gcattgaaga gattatccga actaccggga aagagaacgc aaagtacctg  1560
attgaaaaaa tcaagctgca cgatatgcag gagggaaagt gtctgtattc tctggaggcc  1620
atcccctgg aggacctgct gaacaatcca ttcaactacg aggtcgatca tattatcccc  1680
agaagcgtgt ccttcgacaa ttccttttaac aacaaggtgc tggtcaagca ggaagagaac  1740
tctaaaaagg gcaataggac tcctttccag tacctgtcta gttcagattc caagatctct  1800
tacgaaacct ttaaaaagca cattctgaat ctggccaaag gaaagggccg catcagcaag  1860
accaaaaagg agtacctgct ggaagagcgg gacatcaaca gattctccgt ccagaaggat  1920
tttattaacc ggaatctggt ggacacaaga tacgctactc gcggcctgat gaatctgctg  1980
cgatcctatt tccgggtgaa caatctggat gtgaaagtca agtccatcaa cggcgggttc  2040
acatcttttc tgaggcgcaa atggaagttt aaaaaggagc gcaacaaagg gtacaagcac  2100
catgccgaag atgctctgat tatcgcaaat gccgacttca tctttaagga gtggaaaaag  2160
ctggacaaag ccaagaaagt gatggagaac cagatgttcg aagagaagca ggccgaatct  2220
atgcccgaaa tcgagacaga acaggagtac aaggagattt tcatcactcc tcaccagatc  2280
aagcatatca aggatttcaa ggactacaag tactctcacc gggtgataaa aaagcccaac  2340
agagagctga tcaatgacac cctgtatagt acaagaaaag acgataaggg gaataccctg  2400
attgtgaaca atctgaacgg actgtacgac aaagataatg acaagctgaa aaagctgatc  2460
aacaaaagtc ccgagaagct gctgatgtac caccatgatc ctcagacata tcagaaactg  2520
```

```
aagctgatta tggagcagta cggcgacgag aagaacccac tgtataagta ctatgaagag 2580
actgggaact accctgaccaa gtatagcaaa aaggataatg gccccgtgat caagaagatc 2640
aagtactatg ggaacaagct gaatgcccat ctggacatca cagacgatta ccctaacagt 2700
cgcaacaagg tggtcaagct gtcactgaag ccatacagat cgatgtcta tctggacaac 2760
ggcgtgtata aatttgtgac tgtcaagaat ctggatgtca tcaaaaagga gaactactat 2820
gaagtgaata gcaagtgcta cgaagaggct aaaaagctga aaaagattag caaccaggca 2880
gagttcatcg cctcctttta caacaacgac ctgattaaga tcaatggcga actgtatagg 2940
gtcatcgggg tgaacaatga tctgctgaac cgcattgaag tgaatatgat tgacatcact 3000
taccgagagt atctggaaaa catgaatgat aagcgccccc ctcgaattat caaaacaatt 3060
gcctctaaga ctcagagtat caaaaagtac tcaaccgaca ttctgggaaa cctgtatgag 3120
gtgaagagca aaaagcaccc tcagattatc aaaaagggct aa                    3162

SEQ ID NO: 2              moltype = AA  length = 1053
FEATURE                   Location/Qualifiers
source                    1..1053
                          mol_type = protein
                          organism = Staphylococcus aureus
SEQUENCE: 2
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN 120
VNEVEEDTGN ELSTKEQISR NSKALEEKYV AELQLERLKK DGEVRGSINR FKTSDYVKEA 180
KQLLKVQKAY HQLDQSFIDT YIDLLETRRT YYEGPGEGSP FGWKDIKEWY EMLMGHCTYF 240
PEELRSVKYA YNADLYNALN DLNNLVITRD ENEKLEYYEK FQIIENVFKQ KKKPTLKQIA 300
KEILVNEEDI KGYRVTSTGK PEFTNLKVYH DIKDITARKE IIENAELLDQ IAKILTIYQS 360
SEDIQEELTN LNSELTQEEI EQISNLKGYT GTHNLSLKAI NLILDELWHT NDNQIAIFNR 420
LKLVPKKVDL SQQKEIPTTL VDDFILSPVV KRSFIQSIKV INAIIKKYGL PNDIIIELAR 480
EKNSKDAQKM INEMQKRNRQ TNERIEEIIR TTGKENAKYL IEKIKLHDMQ EGKCLYSLEA 540
IPLEDLLNNP FNYEVDHIIP RSVSFDNSFN NKVLVKQEEN SKKGNRTPFQ YLSSSDSKIS 600
YETFKKHILN LAKGKGRISK TKKEYLLEER DINRFSVQKD FINRNLVDTR YATRGLMNLL 660
RSYFRVNNLD VKVKSINGGF TSFLRRKWKF KKERNKGYKH HAEDALIIAN ADFIFKEWKK 720
LDKAKKVMEN QMFEEKQAES MPEIETEQEY KEIFITPHQI KHIKDFKDYK YSHRVDKKPN 780
RELINDTLYS TRKDDKGNTL IVNNLNGLYD KDNDKLKKLI NKSPEKLLMY HHDPQTYQKL 840
KLIMEQYGDE KNPLYKYYEE TGNYLTKYSK KDNGPVIKKI KYYGNKLNAH LDITDDYPNS 900
RNKVVKLSLK PYRFDVYLDN GVYKFVTVKN LDVIKKENYY EVNSKCYEEA KKLKKISNQA 960
EFIASFYNND LIKINGELYR VIGVNNDLLN RIEVNMIDIT YREYLENMND KRPPRIIKTI 1020
ASKTQSIKKY STDILGNLYE VKSKKHPQII KKG                             1053

SEQ ID NO: 3              moltype = DNA  length = 97
FEATURE                   Location/Qualifiers
misc_feature              1..97
                          note = guide sequence
source                    1..97
                          mol_type = other DNA
                          organism = synthetic construct
SEQUENCE: 3
ggaaattagg tgcgctgggg gttttagtac tctggaaaca gaatctacta aaacaaggca  60
aaatgccgtg tttatctcgt caacttgttg gcgagat                           97

SEQ ID NO: 4              moltype = DNA  length = 3191
FEATURE                   Location/Qualifiers
misc_feature              1..3191
                          note = targent sequence
source                    1..3191
                          mol_type = other DNA
                          organism = synthetic construct
SEQUENCE: 4
agcgcccaat acgcaaaccg cctctccccg cgcgttggcc gattcattaa tgcagctggc  60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagcttg 240
catgcctgca ggtcgactct agaggatccc cgggtaccga gctcgaattc actgccgtc  300
gttttacaac gtcgtgactg ggaaaaccct ggcgttaccc aacttaatcg ccttgcagca 360
catcccccctt tcgccagctg gcgtaatagc gaagaggccc gcaccgatcg cccttcccaa 420
cagttgcgca gcctgaatgg cgaatggcgc ctgatgcggt attttctcct tacgcatctg 480
tgcggtattt cacaccgcat acgtcaaagc aaccatagta cgcgccctgt agcggcgcat 540
taagcgcggc gggtgtggtg gttacgcgca gcgtgaccgc tacacttgcc agcgccctag 600
cgcccgctcc tttcgctttc ttcccttcct ttctcgccac gttcgccggc tttccccgtc 660
aagctctaaa tcggggggctc cctttagggt tccgatttag tgctttacgg cacctcgacc 720
ccaaaaaact tgatttgggt gatggttcac gtagtgggcc atcgccctga tagacggttt 780
ttcgcccttt gacgttggag tccacgttct ttaatagtgg actcttgttc caaactggaa 840
caacactcaa ccctatctcg ggctattctt tgatttata agggattttg ccgatttcgg 900
cctattggtt aaaaaatgag ctgatttaac aaaaatttaa cgcgaatttt aacaaaatat 960
taacgtttac aattttatgg tgcactctca gtacaatctg ctctgatgcc gcatagttaa 1020
gccagccccg acacccgcca acacccgctg acgcgcccta acgggcttgt ctgctccccg 1080
catccgctta cagacaagct gtgaccgtct ccgggagctg catgtgtcag aggttttcac 1140
cgtcatcacc gaaacgcgcg agacgaaagg gcctcgtgat acgcctattt ttataggtta 1200
atgtcatgat aataatggtt tcttagacgt caggtggcac ttttcgggga atgtgcgcg 1260
gaaccccctat ttgtttattt ttctaaatac ggaaattagg tgcgcttggc ttgaattgga 1320
ttcaaatatg tatccgctca tgagacaata accctgataa atgcttcaat aatattgaaa 1380
```

```
aaggaagagt atgagtattc aacatttccg tgtcgccctt attccctttt ttgcggcatt   1440
ttgccttcct gtttttgctc acccagaaac gctggtgaaa gtaaaagatg ctgaagatca   1500
gttgggtgca cgagtgggtt acatcgaact ggatctcaac agcggtaaga tccttgagag   1560
ttttcgcccc gaagaacgtt ttccaatgat gagcactttt aaagttctgc tatgtggcgc   1620
ggtattatcc cgtattgacg ccgggcaaga gcaactcggt cgccgcatac actattctca   1680
gaatgacttg gttgagtact caccagtcac agaaaagcat cttacggatg gcatgacagt   1740
aagagaatta tgcagtgctg ccataaccat gagtgataac actgcggcca acttacttct   1800
gacaacgatc ggaggaccga aggagctaac cgcttttttg cacaacatgg ggatcatgt   1860
aactcgcctt gatcgttggg aaccggagct gaatgaagcc ataccaaacg acgagcgtga   1920
caccacgatg cctgtagcaa tggcaacaac gttgcgcaaa ctattaactg gcgaactact   1980
tactctagct tcccggcaac aattaataga ctggatggag gcggataaag ttgcaggacc   2040
acttctgcgc tcggcccttc cggctggctg gtttattgct gataaatctg gagccggtga   2100
gcgtgggtct cgcggtatca ttgcagcact ggggccagat ggtaagccct cccgtatcgt   2160
agttatctac acgacgggga gtcaggcaac tatggatgaa cgaaatagac agatcgctga   2220
gataggtgcc tcactgatta agcattggta actgtcagac caagtttact catatatact   2280
ttagattgat ttaaaacttc attttttaatt taaaaggatc taggtgaaga tcctttttga   2340
taatctcatg accaaaatcc cttaacgtga gttttcgttc cactgagcgt cagacccccg   2400
agaaaagatc aaaggatctt ttttttttctg gcgtaatctg ctgcttgca   2460
aacaaaaaaa ccaccgctac cagcggtggt ttgtttgccg gatcaagagc taccaactct   2520
ttttccgaag gtaactggct tcagcagagc gcagatacca aatactgtcc ttctagtgta   2580
gccgtagtta ggccaccact tcaagaactc tgtagcaccg cctacatacc tcgctctgct   2640
aatcctgtta ccagtggctg ctgccagtgg cgataagtcg tgtcttaccg ggttggactc   2700
aagacgatag ttaccggata aggcgcagcg gtcgggctga acggggggtt cgtgcacaca   2760
gcccagcttg gagcgaacga cctacaccga actgagatac ctacagcgtg agctatgaga   2820
aagcgccacg cttcccgaag ggagaaaggc ggacaggtat ccggtaagcg gcagggtcgg   2880
aacaggagag cgcacgaggg agcttccagg gggaaacgcc tggtatcttt atagtcctgt   2940
cgggtttcgc cacctctgac ttgagcgtcg atttttgtga tgctcgtcag ggggggcggag   3000
cctatggaaa aacgccagca acgcggcctt tttacggttc ctggccttt gctggccttt   3060
tgctcacatg ttcttcctg cgttatcccc tgattctgtg gataaccgta ttaccgcctt   3120
tgagtgagct gataccgctc gccgcagccg aacgaccgag cgcagcgagt cagtgagcga   3180
ggaagcggaa g                                                        3191

SEQ ID NO: 5            moltype = DNA   length = 21
FEATURE                 Location/Qualifiers
misc_feature            1..21
                        note = spacer sequence
source                  1..21
                        mol_type = other DNA
                        organism = synthetic construct
SEQUENCE: 5
aaaaataacc ttagtctatc a                                             21

SEQ ID NO: 6            moltype = DNA   length = 21
FEATURE                 Location/Qualifiers
misc_feature            1..21
                        note = spacer sequence
source                  1..21
                        mol_type = other DNA
                        organism = synthetic construct
SEQUENCE: 6
ttgtatcctg taatgctctc a                                             21

SEQ ID NO: 7            moltype = DNA   length = 21
FEATURE                 Location/Qualifiers
misc_feature            1..21
                        note = spacer sequence
source                  1..21
                        mol_type = other DNA
                        organism = synthetic construct
SEQUENCE: 7
acctggttca tcatcactaa t                                             21

SEQ ID NO: 8            moltype = DNA   length = 21
FEATURE                 Location/Qualifiers
misc_feature            1..21
                        note = spacer sequence
source                  1..21
                        mol_type = other DNA
                        organism = synthetic construct
SEQUENCE: 8
ctaatcatta tgctgaggat t                                             21

SEQ ID NO: 9            moltype = DNA   length = 21
FEATURE                 Location/Qualifiers
misc_feature            1..21
                        note = spacer sequence
source                  1..21
                        mol_type = other DNA
                        organism = synthetic construct
```

```
SEQUENCE: 9
gctgatgttt gaaattaaca c                                                     21

SEQ ID NO: 10           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 10
ttaacatctt aatccaatca a                                                     21

SEQ ID NO: 11           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 11
taatctgaaa aagaaatata g                                                     21

SEQ ID NO: 12           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 12
tatgctgagg atttggaaag g                                                     21

SEQ ID NO: 13           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 13
ggtaagtaag atcttaaaat g                                                     21

SEQ ID NO: 14           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 14
aagtactcag aacagctgct g                                                     21

SEQ ID NO: 15           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 15
tgcataccta atcattatgc t                                                     21

SEQ ID NO: 16           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 16
tcattatgct gaggatttgg a                                                     21

SEQ ID NO: 17           moltype = DNA  length = 21
FEATURE                 Location/Qualifiers
misc_feature            1..21
                        note = spacer sequence
source                  1..21
                        mol_type = other DNA
```

```
                            organism = synthetic construct
SEQUENCE: 17
cctgtccata attagtccat g                                              21

SEQ ID NO: 18              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 18
tgcttgtccc tctgtcaatg g                                              21

SEQ ID NO: 19              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 19
ggagtggcca gagtccagct t                                              21

SEQ ID NO: 20              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 20
ggcttctcag gaatgacacc c                                              21

SEQ ID NO: 21              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 21
ggccggggtg tcattcctga g                                              21

SEQ ID NO: 22              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 22
gagaaccacc cagggtccag g                                              21

SEQ ID NO: 23              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 23
gactcagggc cagatgcagg g                                              21

SEQ ID NO: 24              moltype = DNA   length = 21
FEATURE                    Location/Qualifiers
misc_feature               1..21
                           note = spacer sequence
source                     1..21
                           mol_type = other DNA
                           organism = synthetic construct
SEQUENCE: 24
agagtccagc ttgggcccac g                                              21

SEQ ID NO: 25              moltype = DNA   length = 21
FEATURE                    Location/Qualifiers
misc_feature               1..21
                           note = spacer sequence
source                     1..21
```

```
                        mol_type = other DNA
                        organism = synthetic construct
SEQUENCE: 25
tggccactcc ctggccaggc t                                              21

SEQ ID NO: 26           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 26
tggccccaca gggcttgaag c                                              21

SEQ ID NO: 27           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 27
acagtcatag caggctccag g                                              21

SEQ ID NO: 28           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 28
ggcctcccca aagcctggcc a                                              21

SEQ ID NO: 29           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 29
tggccaggct ttggggaggc c                                              21

SEQ ID NO: 30           moltype = DNA  length = 21
FEATURE                 Location/Qualifiers
misc_feature            1..21
                        note = spacer sequence
source                  1..21
                        mol_type = other DNA
                        organism = synthetic construct
SEQUENCE: 30
gccagcccac ttgggcttct c                                              21

SEQ ID NO: 31           moltype = DNA  length = 20
FEATURE                 Location/Qualifiers
misc_feature            1..20
                        note = HPRT PCR primer (Forward)
source                  1..20
                        mol_type = other DNA
                        organism = synthetic construct
SEQUENCE: 31
tacacgtgtg aaccaacccg                                                20

SEQ ID NO: 32           moltype = DNA  length = 22
FEATURE                 Location/Qualifiers
misc_feature            1..22
                        note = HPRT PCR primer (Reverse)
source                  1..22
                        mol_type = other DNA
                        organism = synthetic construct
SEQUENCE: 32
gtaaggcccT cctcttttat tt                                             22

SEQ ID NO: 33           moltype = DNA  length = 22
FEATURE                 Location/Qualifiers
misc_feature            1..22
                        note = EMX1 region A PCR primer (Forward)
```

```
source                    1..22
                          mol_type = other DNA
                          organism = synthetic construct
SEQUENCE: 33
agtttctcat ctgtgcccct cc                                              22

SEQ ID NO: 34             moltype = DNA  length = 22
FEATURE                   Location/Qualifiers
misc_feature              1..22
                          note = EMX1 region A PCR primer (Reverse)
source                    1..22
                          mol_type = other DNA
                          organism = synthetic construct
SEQUENCE: 34
ctgaacgcgt ttgctctacc ag                                              22

SEQ ID NO: 35             moltype = DNA  length = 20
FEATURE                   Location/Qualifiers
misc_feature              1..20
                          note = EMX1 region B PCR primer (Forward)
source                    1..20
                          mol_type = other DNA
                          organism = synthetic construct
SEQUENCE: 35
tttcacttgg gtgccctagg                                                 20

SEQ ID NO: 36             moltype = DNA  length = 19
FEATURE                   Location/Qualifiers
misc_feature              1..19
                          note = EMX1 region B PCR primer (Reverse)
source                    1..19
                          mol_type = other DNA
                          organism = synthetic construct
SEQUENCE: 36
ccctcttgcc agaacttcc                                                  19

SEQ ID NO: 37             moltype = DNA  length = 4140
FEATURE                   Location/Qualifiers
source                    1..4140
                          mol_type = other DNA
                          organism = synthetic construct
CDS                       1..4140
                          note = NLS-WT-dSaCas9(D10A,N580A)-NLS-KRAB-P2A-Puro fusion
                           protein
SEQUENCE: 37
atggccccaa agaagaagcg gaaggtcggt atccacggag tcccagcagc caagcggaac     60
tacatcctgg gcctggccat cggcatcacc agcgtgggct acggcatcat cgactacgag    120
acacgggacg tgatcgatgc cggcgtgcgc ctgttcaaag aggccaacgt ggaaaacaac    180
gagggcaggc ggagcaagag aggcgccaga aggctgaagc ggcggaggcg catagaatc     240
cagagagtga gaaagctgct gttcgactac aacctgctga ccgaccacag cgagctgagc    300
ggcatcaacc cctacgaggc cagagtgaag ggcctgagcc agaagctgag cgaggaagaa    360
ttctctgccg ccctgctgca cctggccaag agaagaggcg tgcacaacgt gaacgaggtg    420
gaagaggaca ccggcaacga gctgtccacc aaagagcaga tcagccggaa cagcaaggcc    480
ctggaagaga atacgtggc cgaactgcag ctggaacgcc tgaagaaaga cggcgaagtg     540
cgggcagtga tcaacagatt caagaccagc gactacgtga agaagccaac acagctgctg    600
aaggtgcaga aggcctacca ccagctggac cagagcttca tcgacaccta catccgcctg    660
ctggaaaccc ggcggaccta ctatgaggga cctggcgagg cagccccctt cggctggaag    720
gacatcaaaa atggtacga gatgctgatg ggccactgca cctacttccc gaggaactg      780
cggaacgtga gtacgccta caacgccgac tgtacaacg ccctgaacga cctgaacaat      840
ctcgtgatca ccagggacga gaacgagaag ctgaatatt cgagaagtt ccagatcatc      900
gagaacgtgt tcaagcagaa gaagaagccc accctgaagc agatcgccaa agaaatcctc    960
gtgaacgaag aggatattaa gctacaga gtgaccagca ccggcaagcc cgagttcacc     1020
aacctgaagg tgtaccacga catcaaggac tatccgccc ggaaagagat tattgagaac    1080
gccgacatgc tggatcagat tgccaagatc ctgaccatc accagagcga cgaggacaat    1140
caggaagaac tgaccaatct gaactccgag ctgacccagg aagagatcga gcagatctct    1200
aatctgaagg gctataccgg cacccacaac ctgagcctga aggccatcaa cctgatcctg    1260
gacgagctgt ggcacaccaa cgacaaccag atcgctatct tcaaccggct gaagctggtg    1320
cccaagaaga tggaccctgc ccagccagaa gagatcccca ccaccctggt ggacgactc    1380
atcctgagcc ccgtcgtgaa gagaagcttc atccagagca tcaaagtgat caacgccatc    1440
atcaagaagt acggcctgcc caacgacatc attatcgagc tggccccgcga agaactgcc    1500
aaggacgccc agaaaatgat caacgagatg cagaagcgga accggcagac caacgagcgg    1560
atcgaggaaa tcatccggac caccggcaaa gagaacgcca gtacctgat cgagaagatc    1620
aagctgcacg acatgcagga aggcaagtgc ctgtacagcc tggaagccat ccctctggaa    1680
gatctgctga acaaccctt caactatgag gtggaccaca tcatccccag aagcgtgtcc    1740
ttcgacaaca gcttcaacaa caaggtgctc gtgaagcagg aagaagcagg caagaagggc    1800
aaccggaccc cattccagta cctgagcagc agcgacagca gatcagcta cgaaaccttc    1860
aagaagcaca tcctgaatct ggccaagggg aaggcagaa tcagcaagac caagaaagag    1920
tatctgctga agaacggga catcaacagg ttctccgtgc agaaagactt catcaaccgg    1980
aacctggtgg ataccagata cgccaccaga ggcctgatga acctgctgcg agctacttc    2040
```

```
                       -continued agagtgaaca  acctggacgt  gaaagtgaag  tccatcaatg  gcggcttcac  cagctttctg   2100
cggcggaagt  ggaagtttaa  gaaagagcgg  aacaagggt   acaagcacca  cgccgaggac   2160
gccctgatca  ttgccaacgc  cgatttcatc  ttcaaagagt  ggaagaaact  ggacaaggcc   2220
aaaaagtga   tggaaaacca  gatgttcgag  gaaaagcagg  ccgagagcat  gcccgagatc   2280
gaaaccgagc  aggagtacaa  agagatcttc  atcccccc    accagatcaa  gcacattaag   2340
gacttcaagg  actacaagta  cagccaccgg  gtggacaaga  agcctaatag  agagctgatt   2400
aacgacaccc  tgtactccac  ccggaaggac  gacaagggca  cacccctgat  cgtgaacaat   2460
ctgaacggcc  tgtacgacaa  ggacaatgac  aagctgaaaa  agctgatcaa  caagagcccc   2520
gaaaagctgc  tgatgtacca  ccacgacccc  cagacctaca  agaaactgaa  gctgattatg   2580
gaacagtacg  gcgacgagaa  gaatcccctg  tacaagtact  acgaggaaac  cgggaactac   2640
ctgaccaagt  actccaaaaa  ggacaacggc  cccgtgatca  agaagattaa  gtattacggc   2700
aacaaactga  acgccatctg  gacatcacc   gacgactacc  ccaacagcag  aaacaaggtc   2760
gtgaagctgt  ccctgaagcc  ctacagattc  gacgtgtacc  tggacaatgg  cgtgtacaag   2820
ttcgtgaccg  tgaagaatct  ggatgtgatc  aaaaaagaaa  actactacga  agtgaatagc   2880
aagtgctatg  aggaagctaa  gaagctgaag  aagatcagca  accaggccga  gtttatcgcc   2940
tccttctaca  acaacgatct  gatcaagatc  aacggcgagc  tgtatagagt  gatcggcgtg   3000
aacaacgacc  tgctgaaccg  gatcgaagtg  aacatgatcg  acatcaccta  ccgcgagtac   3060
ctggaaaaca  tgaacgacaa  gaggcccccc  aggatcatca  agacaatcgc  ctccaagacc   3120
cagagcatta  agaagtacag  cacagacatt  ctgggcaacc  tgtatgaagt  gaaatctaag   3180
aagcaccctc  agatcatcaa  aaagggcaaa  aggccggcgg  ccacgaaaaa  ggccggccag   3240
gcaaaaaaga  aaaagggatc  catggatgct  aagtcactaa  ctgcctggtc  ccggacactg   3300
gtgaccttca  aggatgtatt  tgtggacttc  accagggagg  agtggaagct  gctggacact   3360
gctcagcaga  tcgtgtacag  aaatgtgatg  ctggagaact  ataagaacct  ggtttccttg   3420
ggttatcagc  ttactaagcc  agatgtgatc  ctccggttgg  agaagggaga  gagcccggga   3480
agcggtgcta  ctaacttcag  cctgctgaag  caggctggag  acgtggagga  gaaccctgga   3540
cctaccgagt  acaagcccac  ggtgcgcctc  gccaccgcga  acgacgtccc  caggagccgc   3600
cgcaccctcg  ccgccgcgtt  cgccgactac  cccgccacgg  ccacacctcg  cgatccggac   3660
cgccacatcg  agcgggtcac  cgagctgcaa  gaactcttcc  tcacgcgcgt  cgggctcgac   3720
atcggcaagg  tgtgggtcgc  ggacgacggc  gccgcggtgg  cggtctggac  cacgccggag   3780
agcgtgcgaag  cggggcggt   gttcgccgag  atcggcccgc  ggttgagcgt  cgatgagcgg   3840
tcccggctgg  ccgcgcagca  acagatggaa  ggcctcctgg  cgccgcaccg  gcccaaggag   3900
cccgcgtggt  tcctggccac  cgtcggagtc  tcgcccgacc  accagggcaa  gggtctgggc   3960
agcgccgtcg  tgctccccgg  agtggaggcg  gccgagcgcg  ccggggtgcc  cgccttcctg   4020
gaaacctccg  cgcccgcaa   cctcccctcc  tacgagcggc  tcggcttcac  cgtcaccgcc   4080
gacgtcgagt  gcccgaagg   accgcgcacc  tggtgcatga  cccgcaagcc  cggtgcctga   4140

SEQ ID NO: 38           moltype = AA   length = 1379
FEATURE                 Location/Qualifiers
source                  1..1379
                        mol_type = protein
                        organism = synthetic construct
SEQUENCE: 38
MAPKKKRKVG IHGVPAAKRN YILGLAIGIT SVGYGIIDYE TRDVIDAGVR LFKEANVENN       60
EGRRSKRGAR RLKRRRHRI  QRVKKLLFDY NLLTDHSELS GINPYEARVK GLSQKLSEEE      120
FSAALLHLAK RRGVHNVNEV EEDTGNELST KEQISRNSKA LEEKYVAELQ LERLKKDGEV      180
RGSINRFKTS DYVKEAQLL  KVQKAYHQLD QSFIDTYIDL LETRRTYYEG PGEGSPFGWK      240
DIKEWYEMLM GHCTYFPEEL RSVKYAYNAD LYNALNDLNN LVITRDENEK LEYYEKFQII      300
ENVFKQKKKP TLKQIAKEIL VNEEDIKGYR VTSTGKPEFT NLKVYHDIKD ITARKEIIEN      360
AELLDQIAKI LTIYQSSEDI QEELTNLNSE LTQEEIEQIS NLKGYTGTHN LSLKAINLIL      420
DELWHTNDNQ IAIFNRLKLV PKKVDLSQQK EIPTTLVDDF ILSPVVKRSF IQSIKVINAI      480
IKKYGLPNDI IIELAREKNS KDAQKMINEM QKRNRQTNER IEEIIRTTGK ENAKYLIEKI      540
KLHDMQEGKC LYSLEAIPLE DLLNNPFNYE VDHIIPRSVS FDNSFNNKVL VKQEEASKKG      600
NRTPFQYLSS SDKISYETF  KKHILNLAKG KGRISKTKKE YLLEERDINR FSVQKDFINR      660
NLVDTRYATR GLMNLLRSYF RVNNLDVKVK SINGGFTSFL RRKWKFKKER NKGYKHHAED      720
ALIIANADFI FKEWKKLDKA KKVMENQMFE EKQAESMPEI ETEQEYKEIF ITPHQIKHIK      780
DFKDYKYSHR VDKKPNRELI NDTLYSTRKD DKGNTLIVNN LNGLYDKDND KLKKLINKSP      840
EKLLMYHHDP QTYQKLKLIM EQYGDEKNPL YKYYEETGNY LTKYSKKDNG PVIKKIKYYG      900
NKLNAHLDIT DDYPNSRNKV VKLSLKPYRF DVYLDNGVYK FVTVKNLDVI KKENYYEVNS      960
KCYEEAKKLK KISNQAEFIA SFYNNDLIKI NGELYRVIGV NNDLLNRIEV NMIDITYREY     1020
LENMNDKRPP RIIKTIASKT QSIKKYSTDI LGNLYEVKSK KHPQIIKKGK RPAATKKAGQ     1080
AKKKKGSMDA KSLTAWSRTL VTFKDVFVDF TREEWKLLDT AQQIVYRNVM LENYKNLVSL     1140
GYQLTKPDVI LRLEKGEEPG SGATNFSLLK QAGDVEENPG PTEYKPTVRL ATRDDVPRAV     1200
RTLAAAFADY PATRHTVDPD RHIERVTELQ ELFLTRVGLD IGKVWVADDG AAVAVWTTPE     1260
SVEAGAVFAE IGPRMAELSG SRLAAQQQME GLLAPHRPKE PAWFLATVGV SPDHQGKGLG     1320
SAVVLPGVEA AERAGVPAFL ETSAPRNLPF YERLGFTVTA DVEVPEGPRT WCMTRKPGA     1379

SEQ ID NO: 39           moltype = DNA  length = 4140
FEATURE                 Location/Qualifiers
source                  1..4140
                        mol_type = other DNA
                        organism = synthetic construct
CDS                     1..4140
                        note = NLS-PF(v15)dSaCas9(D10A,N580A)-NLS-KRAB-P2A-Puro
                        fusion protein
SEQUENCE: 39
atggccccaa agaagaagcg gaaggtcggt atccacggag tcccagcagc caagcggaac      60
tacatcctgg gctggccat  cggcatcacc agcgtgggct acggcatcat cgactacgag     120
acacgggacg tgatcgatgc cggcgtgcgg ctgttcaaaa ggccaacgt  ggaaaacaac     180
gagggcaggc ggagcaagag aggcgccaga aggctgaagc ggcggaggcg gcatagaatc     240
```

```
cagagagtga agaagctgct gttcgactac aacctgctga ccgaccacag cgagctgagc  300
ggcatcaacc cctacgaggc cagagtgaag ggcctgagcc agaagctgag cgaggaagag  360
ttctctgccg ccctgctgca cctggccaag agaagaggcg tgcacaacgt gaacgaggtg  420
gaagaggaca ccggcaacga gctgtccacc aagagcaga tcagccggaa cagcaaggcc  480
ctggaagaga aatacgtggc cgaactgcag ctggaacagc tgaagaaaga cggcgaagtg  540
cggggcagca tcaacagatt caagaccagc gactacgtga agaagccaa acagctgctg  600
aaggtgcaga aggcctacca ccagctggac cagagcttca tcgacaccta catcgacctg  660
ctggaaaccc ggcggaccta ctatgaggga cctggcgagg gcagcccctt cggctggaag  720
gacatcaaag aatggtacga gatgctgatg ggccactgca cctacttccc cgaggaactg  780
cggagcgtga agtacgccta caacgccgac ctgtacaacg ccctgaacga cctgaacaat  840
ctcgtgatca ccagggacga gaacgagaag ctggaatatt acgagaagtt ccagatcatc  900
gagaacgtgt tcaagcagaa gaagaagccc accctgaagc agatcgccaa agaaatcctc  960
gtgaacgaag aggatattaa ggctacagaa gtgaccagca ccggcaagcc cgagttcacc 1020
aacctggaag tgtaccacga catcaaggac attaccccgg aaagagat tattgagaac 1080
gccgagctgc tggatcagat tgccaagatc ctgaccatct accagagcag cgaggacatc 1140
caggaagaac tgaccaatct gaactccgag ctgacccagg aagagatcga gcagatctct 1200
aatctgaagg gctataccgg cacccacaac ctgagcctga aggccatcaa cctgatcctg 1260
gacgagctgt ggcacaccaa cgacaaccag atcgctatct tcaaccggct gaagctggtg 1320
cccaagaagg tggacctgtc ccagcagaaa gagatcccca ccaccctggt ggacgacttc 1380
atcctgagcc ccgtcgtgaa agaagcttc atccagagca tcaaagtgat caacgccatc 1440
atcaagaagt acggcctgcc caacgacatc attatcgagc tggcccgcga agaactcc 1500
aaggacgccc agaaaatgat caacgacatg caagcgcaga ccggcagac caagagcgg 1560
atcgaggaaa tcatccggac caccggcaaa gagaacgcca agtacctgat cgagaagatc 1620
aagctgcacg acatgcagga aggcaagtgc ctgtacagcc tggaagccat ccctctggaa 1680
gatctgctga caaccccttt caactatgag gtggaccaca tcatcccag aagcgtgtcc 1740
ttcgacaaca gcttcaacaa caaggtgctc gtgaagcagga aagaagccaa caagaaggc 1800
aaccggaccc cattccagta cctgagcagc agcgacagca gatcagcta cgaaaccttc 1860
aagaagcaca tcctgaatct ggccaagggc aagggcagaa tcagcaagac caagaaagag 1920
tatctgctgg aagaacggga catcaacagg ttctccgtgc agaaagactt catcaaccgg 1980
aacctggtgg ataccagata cgccaccaga ggcctgatga acctgctgcg gagctactc 2040
agagtgaaca acctggacgt gaaagtgaag tccatcaatg gcggcttcac cagctttctg 2100
cggcggaagt ggaagtttaa gaaagagcgg aacaaggggt acaagcacca cgccgaggac 2160
gccctgatca ttgccaacgc cgatttcatc ttcaaagagt ggaagaaact ggacaaggcc 2220
aaaaaagtga tggaaaacca gatgttcgag gaaaagcagg ccgagagcat gcccgagatc 2280
gaaaccgagc aggagtacaa agagatcttc atcacccccc accagatcaa gcacattaag 2340
gacttcaagg actacaagta cagccaccgg gtggacaaga gcctaatag aaagctgatt 2400
aacgacaccc tgtactccac ccggaaggac gacaagggca caccggat cgtgaacat 2460
ctgaacggcc tgtacgacaa ggacaatgac aagctgaaaa agctgatcaa caagagcccc 2520
gaaaagctgc tgatgtacca ccacgacccc cagacctacc agaaactgaa gctgattatg 2580
gaacagtacg gcgacgagaa gaatcccctg tacaagtact acgaggaaac cgggaactac 2640
ctgaccaagt actccaaaaa ggacaacggc ccgtgatca agaagattaa gtattcggc 2700
aacaaactga acagacatct ggacatcacc gacgactacc caacagcag aaacaaggtc 2760
gtgaagctgt ccctgaagcc ctacagattc gacgtgtacc tggacaatgg cgtgtacaag 2820
ttcgtgaccg tgaagaatct ggatgtgatc aaaaaagaaa actactacga agtgaatagc 2880
aagtgctatg aggaagctaa gaagctgaag aagatcagca ccaggccgga gtttatcgcc 2940
tccttctaca gaaacgatct gatcaagatc aacgcgagc tgtatagagt gatcggcgtg 3000
gcgccgacc acctgaacgc catcgaagtg aacatgatcg acatcaccta ccgcgagtac 3060
ctggaaaaca tgaacgacaa gaggcccccc aggatcatta agacaatcag ctccaagacc 3120
cagagcatta gaagtacag cacagacatt ctgggcaacc tgtatgaagt gaaatctaag 3180
aagcaccctc agatcatcaa aaagggcaaa aggccggcgg ccacgaaaaa ggccggccag 3240
gcaaaaaaga aaaagggatc catgatgct aagtcactaa ctgcctggtc ccggacactg 3300
gtgaccttca aggatgtatt tgtggacttc accaggagg agtggaagct gctggacact 3360
gctcagcaga tcgtgtacag aaatgtgatg ctggagaact ataagaacct ggtttccttg 3420
ggttatcagc ttactaagcc agatgtgatc ctccggttgg agaagggaga gagcccggga 3480
agcggggcta ctaacttcag cctgctgaag caggctggag acgtggagga gaaccctgga 3540
cctaccgagt acaagcccac ggtgcgcctc gccaccgcg acgacgtccc cagggccgta 3600
cgcaccctcg ccgccgcgtt cgccgactac cccgccacgc ccacccgt cgatccggac 3660
cgccacatcg agcgggtcac cgagctgcaa gaactcttcc tcacgcgcgt cgggctcgac 3720
atcggcaaag tgtgggtcgc ggacgacggc gccgcgcgtg cggtctggac cacgcccgag 3780
agcgtcgaag cggggcggt gttcgccgag atcgccccgc gcatggccga gttgagcggt 3840
tcccggctgg ccgcgcagca acagatgaa ggcctcctgg cgccgcaccg gcccaaggag 3900
cccgcgtggt tcctgcccac cgtcggagtc tcgcccgacc accagggcaa gggtctgggc 3960
agcgccgtcg tgctccccgg agtggaggcg gccgagcgcg ccggggtgcc cgccttcctg 4020
gaaacctccg ccccgcgcaa cctccccttc tacgagcgg tcggcttcac cgtcaccgcc 4080
gacgtcgagg tgcccgaagg accgcgcacc tggtgcatga cccgcaagcc cggtgcctga 4140
```

```
SEQ ID NO: 40         moltype = AA  length = 1379
FEATURE               Location/Qualifiers
source                1..1379
                      mol_type = protein
                      organism = synthetic construct
SEQUENCE: 40
MAPKKKRKVG IHGVPAAKRN YILGLAIGIT SVGYGIIDYE TRDVIDAGVR LFKEANVENN   60
EGRRSKRGAR RLKRRRRHRI QRVKKLLFDY NLLTDHSELS GINPYEARVK GLSQKLSEEE  120
FSAALLHLAK RRGVHNVNEV EEDTGNELST KEQISRNSKA LEEKYVAELQ LERLKKDGEV  180
RGSINRFKTS DYVKEAKQLL KVQKAYHQLD QSFIDTYIDL LETRRTYYEG PGEGSPFGWK  240
DIKEWYEMLM GHCTYFPEEL RSVKYAYNAD LYNALNDLNN LVITRDENEK LEYYEKFQII  300
ENVFKQKKKP TLKQIAKEIL VNEEDIKGYR VTSTGKPEFT NLKVYHDIKD ITARKEIIEN  360
AELLDQIAKI LTIYQSSEDI QEELTNLNSE LTQEEIEQIS NLKGYTGTHN LSLKAINLIL  420
```

```
DELWHTNDNQ IAIFNRLKLV PKKVDLSQQK EIPTTLVDDF ILSPVVKRSF IQSIKVINAI   480
IKKYGLPNDI IIELAREKNS KDAQKMINEM QKRNRQTNER IEEIIRTTGK ENAKYLIEKI   540
KLHDMQEGKC LYSLEAIPLE DLLNNPFNYE VDHIIPRSVS FDNSFNNKVL VKQEEASKKG   600
NRTPFQYLSS SDSKISYETF KKHILNLAKG KGRISKTKKE YLLEERDINR FSVQKDFINR   660
NLVDTRYATR GLMNLLRSYF RVNNLDVKVK SINGGFTSFL RRKWKFKKER NKGYKHHAED   720
ALIIANADFI FKEWKKLDKA KKVMENQMFE EKQAESMPEI ETEQEYKEIF ITPHQIKHIK   780
DFKDYKYSHR VDKKPNRKLI NDTLYSTRKD DKGNTRIVNN LNGLYDKDND KLKKLINKSP   840
EKLLMYHHDP QTYQKLKLIM EQYGDEKNPL YKYYEETGNY LTKYSKKDNG PVIKKIKYYG   900
NKLNRHLDIT DDYPNSRNKV VKLSLKPYRF DVYLDNGVYK FVTVKNLDVI KKENYYEVNS   960
KCYEEAKKLK KISNQAEFIA SFYRNDLIKI NGELYRVIGV AADHLNAIEV NMIDITYREY  1020
LENMNDKRPP RIIKTISSKT QSIKKYSTDI LGNLYEVKSK KHPQIIKKGK RPAATKKAGQ  1080
AKKKKGSMDA KSLTAWSRTL VTFKDVFVDF TREEWKLLDT AQQIVYRNVM LENYKNLVSL  1140
GYQLTKPDVI LRLEKGEEPG SGATNFSLLK QAGDVEENPG PTEYKPTVRL ATRDDVPRAV  1200
RTLAAAFADY PATRHTVDPD RHIERVTELQ ELFLTRVGLD IGKVWVADDG AAVAVWTTPE  1260
SVEAGAVFAE IGPRMAELSG SRLAAQQQME GLLAPHRPKE PAWFLATVGV SPDHQGKGLG  1320
SAVVLPGVEA AERAGVPAFL ETSAPRNLPF YERLGFTVTA DVEVPEGPRT WCMTRKPGA   1379

SEQ ID NO: 41           moltype = DNA   length = 4140
FEATURE                 Location/Qualifiers
source                  1..4140
                        mol_type = other DNA
                        organism = synthetic construct
CDS                     1..4140
                        note = NLS-PF(v51)-dSaCas9(D10A,N580A)-NLS-KRAB-P2A-Puro
                        fusion protein
SEQUENCE: 41
atggccccaa agaagaagcg gaaggtcggt atccacggag tcccagcagc caagcggaac   60
tacatcctgg gcctggccat cggcatcacc agcgtgggct acggcatcat cgactacgag  120
acacgggacg tgatcgatgc cggcgtgcgg ctgttcaaag aggccaacgt ggaaaacaac  180
gagggcaggc ggagcaagag aggcgccaga aggtgaaagc ggcggaggcg gcatagaatc  240
cagagagtga gaagctgctg gttcgactac aacctgctga ccgaccacag cgagctgagc  300
ggcatcaacc cctacgaggc cagagtgaag ggcctgagcc agaagctgag cgaggaagag  360
ttctctgccg ccctgctgca cctggccaag agaagaggcg tgcacaacgt gaacgaggtg  420
gaagaggaca ccggcaacga gctgtccacc aaagagcaga tcagccggaa cagcaaggcc  480
ctggaagaga aatacgtggc cgaactgcag ctgaacggct tgaagaaaga cggcgaagtg  540
cggggcagca tcaacagatt caagaccagc gactacgtga agaagccaa acagctgctg  600
aaggtgcaga aggcctacca ccagctggac cagagcttca tcgacaccta catcgacctg  660
ctggaaaccc ggcggaccta ctatgaggga cctggcgagg cagcccctt cggctggaag  720
gacatcaaag aatggtacga gatgctgatg ggcactgac cctacttccc cgaggaactg  780
cggagcgtga agtacgccta caacgccgac ctgtacaacg ccctgaacga cctgaacaat  840
ctcgtgatca ccaggggcatga gaacgagaag ctggaatatt acgagaagtt ccagatcatc  900
gagaacgtgt tcaagcagaa gaagaagccc accctgaagc agatcgccaa agaaatcctc  960
gtgaactgaa aggatattaa gggctacaga gtgaccagca ccggcaagcc cgagttcacc 1020
aacctgaagg tgtaccacga catcaaggac attaccgccc ggaaagagat tattgagaac 1080
gccgagctgc tggatcagat tgccaagatc ctgaccatct accagagcag cgaggacatc 1140
caggaagaac tgaccaatct gaactccgag ctgacccagg aagagatcga gcagatctct 1200
aatctgaagg gctataccgg cacccacaac ctgagcctga aggccatcaa cctgatcctg 1260
gacgagctgt ggcacaccaa cgacaaccag atcgctatct tcaaccggct gaagctggtg 1320
cccaagaagg tggacctgtc ccagcagaaa gagatcccca ccctggt gga cgacttc    1380
atcctgagcc ccgtcgtgaa gagaagcttc atccagagca tcaaagtgat caacgccatc 1440
atcaagaagt acggcctgcc caacgacatc attatcgagc tggcccgaga gaagaactcc 1500
aaggacgccc agaaaatgat caacgagatg cagaagcgga accggcagac caacgagcgg 1560
atcgaggaaa tcatccggac caccggcaaa gagaacgcca gtacctgat cgagaagatc 1620
aagctgcacg acatgcagga aggcaagtgc ctgtacagcc tggaagccat ccctctggaa 1680
gatctgctga acaacccctt caactatgag gtggaccaca tcatcccag caagcgtgtc 1740
ttcgacaaca gcttcaacaa caaggtgctc gtgaagcagg aagaagccag caagaagggc 1800
aaccggaccc cattccagta cctgagcagc agcgacagca gatcagcta cgaaaccttc 1860
aagaagcaca tcctgaatct ggccaagggc aagggcagaa tcagcaagac caagaaagag 1920
tatctgctgg aagaacggga catcaaccgg ttctccgtgc agaaagatt catcaaccgg 1980
aacctggtgg ataccagata cgccaccaga ggcctgatga acctgctgcg gagctacttc 2040
agagtgaaca acctggacgt gaaagtgaag tccatcaatg gcggcttcac cagctttctg 2100
cggcggaagt ggaagtttaa gaaagagcgg aacaagggt acaagcacca cgccgaggac 2160
gccctgatca ttgccaacgc cgatttcatc ttcaaagagt ggaagaaact ggacaaggcc 2220
aaaaaagtga tggaaaacca gatgttcgag gaaaagcagg ccgagagcat gcccgagatc 2280
gaaaccgagc aggagtacaa agagatcttc atcaccccc accagatcaa gcacattaag 2340
gacttcaagg actacaagta cagccaccgg gtggacaaga gcctaatag aaaactgatt 2400
aacgacaccc tgtactccac ccggaaggac gacaagggca cacccggat cgtgaacaat 2460
ctgaacggcc tgtacgacaa ggacaatgac aagctgaaaa agctcatcaa caagagcccc 2520
gaaaagctgc tgatgtacca ccacgacccc cagacctacc agaaactgaa gctgattatg 2580
gaacagtacg gcgacgagaa gaatcccctg tacaagtact acgaggaaac cgggaactac 2640
ctgaccaagt actccaaaaa ggacaacggc ccgtgatca agaagattaa gtattacggc 2700
aacaaactga acgccatctc ggacatcacc gacgactacc ccaacagcag aaacaaggtc 2760
gtgaagctgt ccctgaagcc ctacagattc gacgtgtacc tggacaatgg cgtgtacaag 2820
ttcgtgaagg tgaatatct ggatgtgatc aaaaagaaa actactacga agtgaatagc 2880
aagtgctatg aggaagctaa gaagctgaag aagatcagca accaggccga gtttatcgcc 2940
tccttctaca gaaacgatct gatcaagatc aacggcgagc tgtatagagt gatcggcgtg 3000
gccaacgacc tgctgaacgc catcgaagtg aacatgatcg acatcaccta ccgcgagtac 3060
ctggaaaaca tgaacgacaa gaggcccccc aggatcttca gacaatctc ctccaagacc 3120
cagagcatta agaagtacag cacagacatt ctgggcaacc tgtatgaagt gaaatctaag 3180
```

```
aagcaccctc agatcatcaa aaagggcaaa aggccggcgg ccacgaaaaa ggccggccag    3240
gcaaaaaaga aaaagggatc catggatgct aagtcactaa ctgcctggtc cggacactg    3300
gtgaccttca aggatgtatt tgtggacttc accaggagg agtggaagct gctggacact    3360
gctcagcaga tcgtgtacag aaatgtgatg ctggagaact ataagaacct ggtttccttg    3420
ggttatcagc ttactaagcc agatgtgatc ctccggttgg agaagggaga agagcccgga    3480
agcggtgcta ctaacttcag cctgctgaag caggctggaa acgtggagga gaaccctgga    3540
cctaccgagt acaagcccac ggtgcgcctc gccaccgcg acgacgtccc cagggccgta    3600
cgcacccttcg ccgccgcgtt cgccgactac cccgccacgc gccacaccgt cgatccggac    3660
cgccacatcg agcgggtcac cgagctgcaa gaactcttcc tcacgcgcgt cgggctcgac    3720
atcggcaagg tgtgggtcgc ggacgacggc gccgcggtgg cggtctggac cacgccggag    3780
agcgtcgaag cggggggcgt gttcgccgag atcgcccgc gcatggccga gttgagcggt    3840
tcccggctgg ccgcgcagca acagatgaa ggcctcctgg cgccgcaccg gcccaaggag    3900
cccgcgtggt tcctggccac cgtcggagtc tcgcccgacc accagggcaa gggtctgggc    3960
agcgccgtcg tgctcccgg atgggaggcg gccgagcgcg gggtgcc cgccttcctg    4020
gaaacctccg cgccccgcaa cctccccttc tacgagcggg tcggcttcac cgtcaccgcc    4080
gacgtcgagg tgcccgaagg accgcgcacc tggtgcatga cccgcaagcc cggtgcctga    4140
```

```
SEQ ID NO: 42              moltype = AA   length = 1379
FEATURE                    Location/Qualifiers
source                     1..1379
                           mol_type = protein
                           organism = synthetic construct
SEQUENCE: 42
MAPKKKRKVG IHGVPAAKRN YILGLAIGIT SVGYGIIDYE TRDVIDAGVR LFKEANVENN     60
EGRRSKRGAR RLKKRRRHRI QRVKKLLFDY NLLTDHSELS GINPYEARVK GLSQKLSEEE    120
FSAALLHLAK RRGVHNVNEV EEDTGNELST KEQISRNSKA LEEKYVAELQ LERLKKDGEV    180
RGSINRFKTS DYVKEAKQLL KVQKAYHQLD QSFIDTYIDL LETRRTYYEG PGEGSPFGWK    240
DIKEWYEMLM GHCTYFPEEL RSVKYAYNAD LYNALNDLNN LVITRDENEK LEYYEKFQII    300
ENVFKQKKKP TLKQIAKEIL VNEEDIKGYR VTSTGKPEFT NLKVYHDIKD ITARKEIIEN    360
AELLDQIAKI LTIYQSSEDI QEELTNLNSE LTQEEIEQIS NLKGYTGTHN LSLKAINLIL    420
DELWHTNDNQ IAIFNRLKLV PKKVDLSQQK EIPTTLVDDF ILSPVVKRSF IQSIKVINAI    480
IKKYGLPNDI IIELAREKNS KDAQKMINEM QKRNRQTNER IEEIIRTTGK ENAKYLIEKI    540
KLHDMQEGKC LYSLEAIPLE DLLNNPFNYE VDHIIPRSVS FDNSFNNKVL VKQEEASKKG    600
NRTPFQYLSS SDSKISYETF KKHILNLAKG KGRISKTKKE YLLEERDINR FSVQKDFINR    660
NLVDTRYATR GLMNLLRSYF RVNNLDVKVK SINGGFTSFL RRKWKFKKER NKGYKHHAED    720
ALIIANADFI FKEWKKLDKA KKVMENQMFE EKQAESMPEI ETEQEYKEIF ITPHQIKHIK    780
DFKDYKYSHR VDKKPNRKLI NDTLYSTRKD DKGNTRIVNN LNGLYDKDND KLKKLINKSP    840
EKLLMYHHDP QTYQKLKLIM EQYGDEKNPL YKYYEETGNY LTKYSKKDNG PVIKKIKYYG    900
NKLNAHLDIT DDYPNSRNKV VKLSLKPYRF DVYLDNGVYK FVKVKNLDVI KKENYYEVNS    960
KCYEEAKKLK KISNQAEFIA SFYRNDLIKI NGELYRVIGV ANDLLNAIEV NMIDITYREY   1020
LENMNDKRPP RIFKTISSKT QSIKKYSTDI LGNLYEVKSK KHPQIIKKGK RPAATKKAGQ   1080
AKKKKGSMDA KSLTAWSRTL VTFKDVFVDF TREEWKLLDT AQQIVYRNVM LENYKNLVSL   1140
GYQLTKPDVI LRLEKGEEPG SGATNFSLLK QAGDVEENPG PTEYKPTVRL ATRDDVPRAV   1200
RTLAAAFADY PATRHTVDPD RHIERVTELQ ELFLTRVGLD IGKVWVADDG AAVAVWTTPE   1260
SVEAGAVFAE IGPRMAELSG SRLAAQQQME GLLAPHRPKE PAWFLATVGV SPDHQGKGLG   1320
SAVVLPGVEA AERAGVPAFL ETSAPRNLPF YERLGFTVTA DVEVPEGPRT WCMTRKPGA   1379
```

```
SEQ ID NO: 43              moltype = DNA   length = 21
FEATURE                    Location/Qualifiers
misc_feature               1..21
                           note = sgRNA sequence_sgRNA-KRAS#1(WT)
source                     1..21
                           mol_type = other DNA
                           organism = synthetic construct
SEQUENCE: 43
gggaaggctg gaccgaggca g                                                21

SEQ ID NO: 44              moltype = DNA   length = 21
FEATURE                    Location/Qualifiers
misc_feature               1..21
                           note = sgRNA sequence_sgRNA-KRAS#2(WT)
source                     1..21
                           mol_type = other DNA
                           organism = synthetic construct
SEQUENCE: 44
cagtccgaaa tggcgggggc c                                                21

SEQ ID NO: 45              moltype = DNA   length = 21
FEATURE                    Location/Qualifiers
misc_feature               1..21
                           note = sgRNA sequence_sgRNA-KRAS#3(WT)
source                     1..21
                           mol_type = other DNA
                           organism = synthetic construct
SEQUENCE: 45
aatcgagctc cgagcacacc g                                                21

SEQ ID NO: 46              moltype = DNA   length = 21
FEATURE                    Location/Qualifiers
```

```
SEQ ID NO: 46              moltype = DNA  length = 21
FEATURE                    Location/Qualifiers
misc_feature               1..21
                           note = sgRNA sequence_sgRNA-KRAS#4(PF-v15)
source                     1..21
                           mol_type = other DNA
                           organism = synthetic construct
SEQUENCE: 46
gtgcgggaga gaggtacgga g                                                    21

SEQ ID NO: 47              moltype = DNA  length = 21
FEATURE                    Location/Qualifiers
misc_feature               1..21
                           note = sgRNA sequence_sgRNA-KRAS#5(PF-v15)
source                     1..21
                           mol_type = other DNA
                           organism = synthetic construct
SEQUENCE: 47
ggagcgagcg cggcgcaggc a                                                    21

SEQ ID NO: 48              moltype = DNA  length = 21
FEATURE                    Location/Qualifiers
misc_feature               1..21
                           note = sgRNA sequence_sgRNA-KRAS#6(PF-v15)
source                     1..21
                           mol_type = other DNA
                           organism = synthetic construct
SEQUENCE: 48
cggccgcggc ggcggaggca g                                                    21

SEQ ID NO: 49              moltype = DNA  length = 20
FEATURE                    Location/Qualifiers
misc_feature               1..20
                           note = sgRNA sequence_sgRNA-C1
source                     1..20
                           mol_type = other DNA
                           organism = synthetic construct
SEQUENCE: 49
acggaggcta agcgtcgcaa                                                      20

SEQ ID NO: 50              moltype = DNA  length = 20
FEATURE                    Location/Qualifiers
misc_feature               1..20
                           note = sgRNA sequence_sgRNA-C2
source                     1..20
                           mol_type = other DNA
                           organism = synthetic construct
SEQUENCE: 50
cgcttccgcg gcccgttcaa                                                      20

SEQ ID NO: 51              moltype = DNA  length = 20
FEATURE                    Location/Qualifiers
misc_feature               1..20
                           note = sgRNA sequence_sgRNA-C3
source                     1..20
                           mol_type = other DNA
                           organism = synthetic construct
SEQUENCE: 51
gtaggcgcgc cgctctctac                                                      20

SEQ ID NO: 52              moltype = DNA  length = 28
FEATURE                    Location/Qualifiers
misc_feature               1..28
                           note = Stuffer sequence
source                     1..28
                           mol_type = other DNA
                           organism = synthetic construct
SEQUENCE: 52
gaaacaccgg agaccacggc aggtctca                                             28
```

MODIFIED CAS9 PROTEIN, AND USE THEREOF

CROSS REFERENCE TO RELATED APPLICATIONS

This application is a continuation divisional of U.S. application Ser. No. 16/644,378, filed on Mar. 4, 2020, which is a National Stage entry under 35 U.S.C. § 371 of PCT/JP2018/032948, filed on Sep. 5, 2018, the entire contents of which are incorporated herein by reference, and is based on U.S. provisional patent application No. 62/554,227 (filing date: Sep. 5, 2017), U.S. provisional patent application No. 62/668,968 (filing date: May 9, 2018), and U.S. provisional patent application No. 62/724,981 (filing date: Aug. 30, 2018), each filed in US, the contents of which are incorporated in full herein.

REFERENCE TO A SEQUENCE LISTING

In accordance with 37 CFR § 1.831, the present specification makes reference to a Sequence Listing submitted electronically as a .xml file named "545662US". The .xml file was generated on Nov. 23, 2022 and is 9,847,391 bytes in size. The entire contents of the Sequence Listing are hereby incorporated by reference.

TECHNICAL FIELD

The present invention relates to a modified Cas9 protein with an expanded targetable region, and use thereof.

BACKGROUND ART

Clustered Regularly Interspaced Short Palindromic Repeats (CRISPR) are known to compose the adaptive immune system that provides acquired resistance against invasive foreign nucleic acids in bacteria and archaea together with Cas (CRISPR-associated) genes. CRISPR frequently originate from phage or plasmid DNA and are composed of 24 bp to 48 bp short, conserved repeat sequences having unique variable DNA sequences referred to as spacers of similar size inserted there between. In addition, a group of genes encoding the Cas protein family is present in the vicinity of the repeat and spacer sequences.

In the CRISPR-Cas system, foreign DNA is cleaved into fragments of about 30 bp by the Cas protein family and inserted into CRISPR. Cas1 and Cas2 proteins, which are among the Cas protein family, recognize a base sequence referred to as proto-spacer adjacent motif (PAM) of foreign DNA, cut the upstream, and insert same into the CRISPR sequence of the host, which creates immune memory of bacteria. RNA generated by transcription of a CRISPR sequence including immune memory (referred to as pre-crRNA) is paired with a partially complementary RNA (trans-activating crRNA: tracrRNA) and incorporated into Cas9 protein which is one of the Cas protein family. The pre-crRNA and tracrRNA incorporated into Cas9 are cleaved by RNaseIII to form small RNA fragments (CRISPR-RNAs: crRNAs) containing a foreign sequence (guide sequence), and a Cas9-crRNA-tracrRNA complex is thus formed. The Cas9-crRNA-tracrRNA complex binds to a foreign invasive DNA complementary to crRNA, and the Cas9 protein, which is an enzyme that cleaves the DNA (nuclease), cleaves the foreign invasive DNA, thereby suppressing and eliminating the function of the DNA that invaded from the outside.

Cas9 protein recognizes the PAM sequence in the foreign invasive DNA, and cleaves the double-stranded DNA at the upstream thereof to give a blunt end. The length and base sequence of the PAM sequence vary depending on the bacterial species, and *Streptococcus pyogenes* (*S. pyogenes*) recognizes 3 bases of "NGG" (N=A/C/T/G). *Streptococcus thermophilus* (*S. thermophilus*) has two Cas9 and they respectively recognize 5-6 bases in the form of "NGGNG" (N=A/C/T/G) or "NNAGAA" (N=A/C/T/G) as PAM sequences. *Francisella novicida* (*F. novicida*) recognizes three bases of "NGR" (N=A/C/T/G; R=A/G). *Staphylococcus aureus* (*S. aureus*) recognizes six bases of "NNGRRT" (N=A/C/T/G; R=A/G).

In recent years, techniques for applying the CRISPR-Cas system in bacteria to genome editing have been actively developed. crRNA and tracrRNA are fused, expressed as a tracrRNA-crRNA chimera (hereinafter to be referred to as guide RNA: gRNA), and utilized. Using this, nuclease (RNA-guided nuclease: RGN) is then recruited to cleave genomic DNA at the target site.

A method using the CRISPR-Cas system only needs to synthesize a short gRNA homologous to the target DNA sequence, and can perform genome editing using the Cas9 protein which is a single protein. Therefore, it is not necessary to synthesize large proteins that differ for each DNA sequence in the manner of conventionally used zinc finger nuclease (ZFN) or transcription activator-like effector nuclease (TALEN), and genome editing can be performed easily and quickly.

Patent Document 1 discloses a genome editing technique that uses a CRISPR-Cas system derived from *S. pyogenes*.

Patent Document 2 discloses a genome editing technique that uses a CRISPR-Cas system derived from *S. thermophilus*. Moreover, Patent document 2 discloses that a Cas9 protein mutant D31A or N891A functions as a DNA cleavage enzyme, nickase, that places a nick only in one of the DNA strands. Moreover, these mutants are also indicated as having homologous recombination efficiency comparable to that of wild-type Cas9 protein while retaining a low incidence of non-homologous end-joining susceptible to the occurrence of mutations such as insertions, deletions and the like in the repair mechanism following DNA cleavage.

Non-Patent Document 1 discloses a CRISPR-Cas system that uses *S. pyogenes*-derived Cas9, wherein the CRISPR-Cas system is a double nickase system that uses two Cas9 protein D10A mutants and a pair of target-specific guide RNA that form a complex with these D10A mutants. Each complex of Cas9 protein D10A mutant and target-specific guide RNA creates only one nick in DNA strand homologous to the guide DNA. The pair of guide RNA has about 20 bases of mismatch and only recognizes a target sequence located in the opposite strand of the target DNA. The two nicks created by each complex of Cas9 protein D10A mutant and target-specific guide RNA mimic a DNA double-strand break (DSB), and the use of the pair of guide RNA is indicated as being able to improve the specificity of Cas 9 protein-mediated genome editing while maintaining a high level of efficiency.

Patent document 3 discloses various mutants of Cas9 protein derived from *S. pyogenes* and Patent Document 4 discloses various mutants of Cas9 protein derived from *F. novicida*.

At present, SpCas9 is widely utilized as a genome editing tool. However, problems remain such as high molecular weight and low efficiency of introduction into viral vectors and the like. To solve the problems, compact Cas9 (SaCas9) derived from *Staphylococcus aureus* has been developed (non-patent document 2), and structure analysis has been performed (non-patent document 3, patent document 5). SaCas9 (1053 residues) has a smaller molecular weight compared to SpCas9 (1368 residues), and has low sequence identity (17%). SpCas9 recognizes 5'-NGG-3' as PAM, and SaCas9 recognizes 5'-NNGRRT-3' (R is a purine base, A or G).

DOCUMENT LIST

Patent Documents patent document 1: WO 2014/093661
patent document 2: National Publication of International Patent Application No. 2015-510778
patent document 3: WO 2016/141224
patent document 4: WO 2017/010543
patent document 5: WO 2016/205759

Non-Patent Document non-patent document 1: Ran, F. A., et al., Double Nicking by RNA-Guided CRISPR Cas9 for Enhanced Genome Editing Specificity. Cell, vol. 154, p 1380-1389, 2013.
non-patent document 2: Ran, F. A., et al., In vivo genome editing using Staphylococcus aureus Cas9. Nature vol. 520, p 186-191, 2015
non-patent document 3: Nishimasu H, et al., Crystal Structure of Staphylococcus aureus Cas9. Cell. Vol. 162, No. 5, p 1113-1126, 2015

SUMMARY OF THE INVENTION

Problems to be Solved by the Invention

The PAM sequence able to be recognized by the *S. aureus*-derived Cas9 (to be also referred to as SaCas9 in the present specification) protein consists of 6 bases of "NNGRRT (N is any base and R is a purine residue (A or G))".

While SaCas9 is advantageous in that it is small as compared with conventional Cas9 proteins, since there are limitations on the PAM sequences that SaCas9 can recognize, there is also a problem of limitation on the editable target sequences.

The present invention aims to provide a modified SaCas9 protein with relaxed restriction on target sequence while maintaining binding ability to guide RNA, and use thereof.

Means of Solving the Problems

The present inventors have taken note of SaCas9 protein as Cas9 protein, and conducted intensive studies in an attempt to solve the above-mentioned problems. As a result, they have succeeded in converting a PAM sequence conventionally consisting of NNGRRT to a sequence of NNGNNN while maintaining the binding ability to guide RNA, by substituting an amino acid at a predetermined position of the SaCas9 protein with a specific amino acid (introducing a mutation), which resulted in the completion of the present invention.

In the present specification, Cas9 protein before introduction of mutation is sometimes to be referred to as wild-type Cas9 protein, and Cas9 protein after introduction of mutation is sometimes to be referred to as modified Cas9 protein or mutant Cas9 protein.

That is, the present invention provides the following.

[1] A protein consisting of an amino acid sequence resulting from mutations of the 985-position and the 991-position, and optionally the 986-position, and at least one site selected from the group consisting of the 782-position, the 800-position, the 888-position, the 968-position, the 988-position, the 1017-position and the 1021-position of the amino acid sequence shown in SEQ ID NO: 2, and having a binding ability to guide RNA.

[2] The protein of the above-mentioned [1], wherein the protein comprises mutation at at least 2 sites selected from the group consisting of the 782-position, the 800-position, the 888-position, the 968-position, the 988-position, the 1017-position and the 1021-position.

[3] The protein of the above-mentioned [1], wherein the protein comprises mutation at at least 3 sites selected from the group consisting of the 782-position, the 800-position, the 888-position, the 968-position, the 988-position, the 1017-position and the 1021-position.

[4] The protein of the above-mentioned [1], wherein the protein comprises mutation at at least 4 sites selected from the group consisting of the 782-position, the 800-position, the 888-position, the 968-position, the 988-position, the 1017-position and the 1021-position.

[5] The protein of the above-mentioned [1], wherein the protein comprises mutation at at least 5 sites selected from the group consisting of the 782-position, the 800-position, the 888-position, the 968-position, the 988-position, the 1017-position and the 1021-position.

[6] The protein of the above-mentioned [1], wherein the protein comprises mutation at at least 6 sites selected from the group consisting of the 782-position, the 800-position, the 888-position, the 968-position, the 988-position, the 1017-position and the 1021-position.

[7] The protein of any of the above-mentioned [1] to [6], wherein the mutation at the 782-position is substitution with lysine or arginine;
the mutation at the 800-position is substitution with arginine or lysine;
the mutation at the 888-position is substitution with an amino acid selected from the group consisting of lysine, arginine, asparagine, glutamine, histidine and serine;
the mutation at the 968-position is substitution with arginine or lysine;
the mutation at the 985-position is substitution with an amino acid selected from the group consisting of alanine, serine, threonine, cysteine, valine and isoleucine;
the mutation at the 986-position is substitution with an amino acid selected from the group consisting of alanine, serine, threonine, cysteine, valine and isoleucine;
the mutation at the 988-position is substitution with histidine;
the mutation at the 991-position is substitution with a non-aromatic amino acid;
the mutation at the 1017-position is substitution with an amino acid selected from the group consisting of phenylalanine, methionine, tyrosine, tryptophan and proline; and
the mutation at the 1021-position is substitution with an amino acid selected from the group consisting of serine, threonine and asparagine.

[8] The protein of any of the above-mentioned [1] to [7], wherein the mutation at the 782-position is substitution with lysine;
the mutation at the 800-position is substitution with arginine;
the mutation at the 888-position is substitution with lysine;
the mutation at the 968-position is substitution with arginine;
the mutation at the 985-position is substitution with alanine;
the mutation at the 986-position is substitution with alanine;
the mutation at the 991-position is substitution with alanine;
the mutation at the 988-position is substitution with histidine;
the mutation at the 1017-position is substitution with phenylalanine; and
the mutation at the 1021-position is substitution with serine.

[9] The protein of any of the above-mentioned [1] to [8], further comprising
(i) mutation at the 927-position and the 929-position,
(ii) mutation at the 929-position,
(iii) mutation at the 927-position,
(iv) mutation at the 889-position, or
(v) mutation at the 927-position, the 929-position and the 889-position.

[10] The protein of the above-mentioned [9], wherein the mutation of (i) is substitution of the 927-position with lysine or arginine, and substitution of the 929-position with asparagine, aspartic acid or alanine;
the mutation of (ii) is substitution of the 929-position with arginine;
the mutation of (iii) is substitution of the 927-position with lysine or arginine;
the mutation of (iv) is substitution of the 889-position with asparagine, serine, lysine, arginine or histidine; and
the mutation of (v) is substitution of the 927-position with lysine or arginine, substitution of the 929-position with asparagine, aspartic acid or alanine, and substitution of the 889-position with asparagine.

[11] The protein of the above-mentioned [9], wherein
the mutation of (i) is substitution of the 927-position with lysine, and substitution of the 929-position with asparagine;
the mutation of (ii) is substitution of the 929-position with arginine;
the mutation of (iii) is substitution of the 927-position with lysine;
the mutation of (iv) is substitution of the 889-position with asparagine; and
the mutation of (v) is substitution of the 927-position with lysine, substitution of the 929-position with asparagine, and substitution of the 889-position with asparagine.

[12] The protein of the above-mentioned [9] consisting of a sequence comprising an amino acid sequence resulting from substitutions of
glutamic acid at the 782-position with lysine,
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
threonine at the 927-position with lysine;
lysine at the 929-position with asparagine; in the amino acid sequence shown in SEQ ID NO: 2;
and having a binding ability to guide RNA.

[13] The protein of the above-mentioned [9] consisting of a sequence comprising an amino acid sequence resulting from substitutions of
glutamic acid at the 782-position with lysine;
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
alanine at the 889-position with asparagine;
threonine at the 927-position with lysine;
lysine at the 929-position with asparagine; in the amino acid sequence shown in SEQ ID NO: 2;
and having a binding ability to guide RNA.

[14] The protein of the above-mentioned [1] consisting of a sequence comprising an amino acid sequence resulting from substitutions of
glutamic acid at the 782-position with lysine,
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine; in the amino acid sequence shown in SEQ ID NO: 2;
and having a binding ability to guide RNA.

[15] The protein of the above-mentioned [1] consisting of a sequence comprising an amino acid sequence resulting from substitutions of
glutamic acid at the 782-position with lysine,
leucine at the 800-position with arginine;
asparagine at the 968-position with arginine;
asparagine at the 985-position with alanine;
arginine at the 991-position with alanine;
alanine at the 1021-position with serine;
threonine at the 927-position with lysine;
lysine at the 929-position with asparagine;
isoleucine at the 1017-position with phenylalanine; in the amino acid sequence shown in SEQ ID NO: 2;
and having a binding ability to guide RNA.

[16] The protein of any of the above-mentioned [1] to [15], having identity of 80% or more at a site other than the mutated positions in the SEQ ID NO: 2.

[17] The protein of any of the above-mentioned [1] to [15], wherein one to several amino acids are substituted, deleted, inserted and/or added at a site other than the mutated positions in the SEQ ID NO: 2.

[18] The protein of any of the above-mentioned [1] to [17], which has RNA-guided DNA endonuclease activity.

[19] The protein of any of the above-mentioned [1] to [17], further having a mutation that deletes nuclease activity in the amino acid sequence shown in SEQ ID NO: 2.

[20] The protein of any of the above-mentioned [1] to [17], having mutation in the protein of the above-mentioned [19] at sites corresponding to the 10-position, the 556-position, the 557-position and/or the 580-position in the amino acid sequence shown in SEQ ID NO: 2.
[21] The protein of the above-mentioned [20], wherein the mutation at the 10-position is substitution of aspartic acid with alanine; the mutation at the 556-position is substitution of aspartic acid with alanine; the mutation at the 557-position is substitution of histidine with alanine; and the mutation at the 580-position is substitution of asparagine with alanine.
[22] The protein of any of the above-mentioned [19] to [21], wherein a transcriptional regulator protein or domain is linked.
[23] The protein of the above-mentioned [22], wherein the transcriptional regulator is a transcription activator.
[24] The protein of the above-mentioned [23], wherein the transcriptional regulator is a transcription silencer or a transcription inhibitor.
[25] A nucleic acid encoding the protein of any of the above-mentioned [1] to [24].
[26] A protein-RNA complex provided with the protein of any of the above-mentioned [1] to [24] and a guide RNA comprising a polynucleotide composed of a base sequence complementary to a base sequence located 1 to 20 to 24 bases upstream from a proto-spacer adjacent motif (PAM) sequence in a target double-stranded polynucleotide.
[27] A method for site-specifically modifying a target double-stranded polynucleotide, including
  a step of mixing and incubating a target double-stranded polynucleotide, a protein and a guide RNA, and
  a step of having the aforementioned protein modify the aforementioned target double-stranded polynucleotide at a binding site located upstream of a PAM sequence; wherein,
  the aforementioned target double-stranded polynucleotide has a PAM sequence composed of NNGNNN (wherein, N is any base and G is guanine),
  the aforementioned protein is the protein of any of the above-mentioned [1] to [24], and the aforementioned guide RNA contains a polynucleotide composed of a base sequence complementary to a base sequence located 1 to 20 to 24 bases upstream from the aforementioned PAM sequence in the aforementioned target double-stranded polynucleotide.
[28] The method of the above-mentioned [27], wherein the modification is site specific cleavage in the target double-stranded polynucleotide.
[29] The method of the above-mentioned [27], wherein the modification is site specific substitution, deletion and/or addition of one or more nucleotides in the target double-stranded polynucleotide.
[30] A method for increasing expression of a target gene in a cell, comprising expressing the protein of the above-mentioned [23] and one or plural guide RNAs for the aforementioned target gene in the aforementioned cell.
[31] A method for decreasing expression of a target gene in a cell, comprising expressing the protein of the above-mentioned [24] and one or plural guide RNAs for the aforementioned target gene in the aforementioned cell.
[32] The method of the above-mentioned [30] or [31], wherein the cell is a eukaryotic cell.
[33] The method of the above-mentioned [30] or [31], wherein the cell is a yeast cell, a plant cell or an animal cell.

EFFECT OF THE INVENTION

According to the present invention, a Cas9 protein can be obtained that recognizes a wide range of PAM sequences while retaining binding strength with a guide RNA. In addition, a simple and rapid site-specific genome editing technology for a target sequence can be provided that uses the aforementioned Cas9 protein.

BRIEF DESCRIPTION OF THE DRAWINGS

FIGS. 5A to 5F show the results verifying alteration of PAM sequence of variants in Example 3 using cleavage activity in an animal cell (HEK293 cell) as an index.
FIG. 6A shows the amino acid sequence of NLS-WT-dSaCas(D10A,N580A)-NLS-KRAB-P2A-Puro fusion protein (sometimes to be abbreviated as WT-dSaCas9-KRAB).
FIG. 6B shows a base sequence encoding the amino acid sequence of FIG. 6A.
FIG. 7A shows the amino acid sequence of NLS-PF(v15)-dSaCas(D10A,N580A)-NLS-KRAB-P2A-Puro fusion protein (sometimes to be abbreviated as PF(v15)-dSaCas9 (D10A, N580A)-KRAB).
FIG. 7B shows a base sequence encoding the amino acid sequence of FIG. 7A.
FIG. 8A shows the amino acid sequence of NLS-PF(v51)-dSaCas(D10A,N580A)-NLS-KRAB-P2A-Puro fusion protein (sometimes is to be abbreviated as PF(v51)-dSaCas9 (D10A, N580A)-KRAB).
FIG. 8B shows a base sequence encoding the amino acid sequence of FIG. 8A.
FIG. 9 shows that PF(v15)-dSaCas9 suppresses expression of KRAS gene more strongly than WT-dSaCas9.
FIG. 10 shows an off-target suppressive effect on WT-dSaCas9 of PF(v15) and PF(v51).

DESCRIPTION OF EMBODIMENTS

Figure 1:
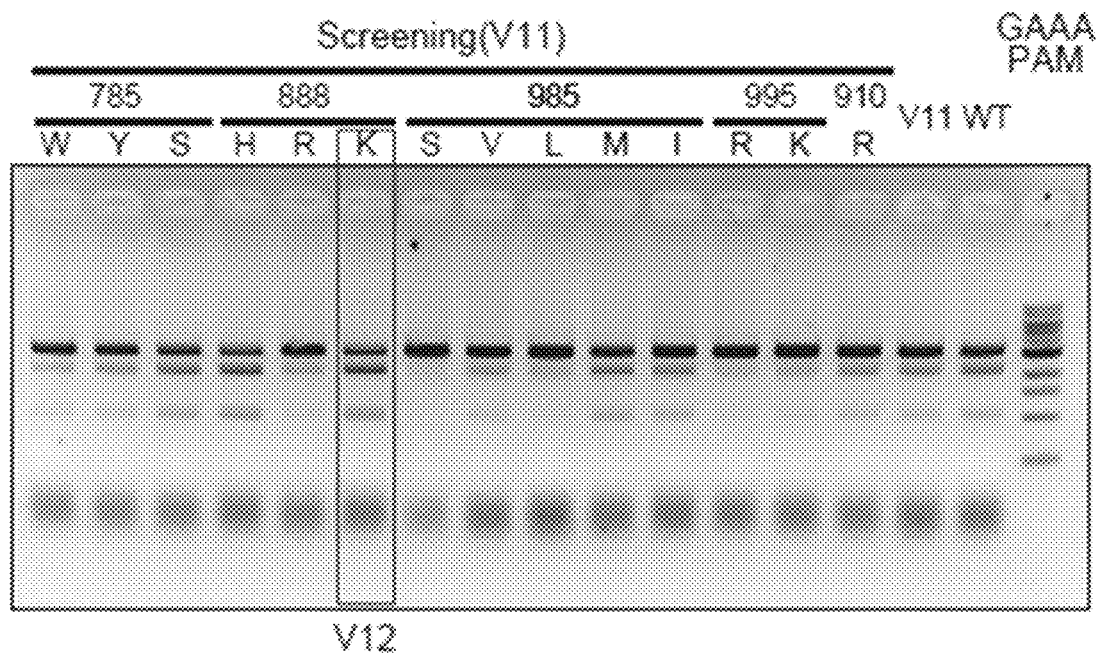
FIG. 1 shows an image representing the results of agarose gel electrophoresis in a DNA cleavage activity measurement test in Example 1. "(NN)GAAA" was used as the PAM sequence.

The present invention is described below. Unless particularly indicated, the terms used in the present specification have meanings generally used in the pertinent field.

<Cas9 Protein Recognizing Wide Range of PAM Sequences>

The protein of the present embodiment is a Cas9 protein that recognizes a wide range of PAM sequences while retaining binding strength with a guide RNA. According to the protein of the present embodiment, a simple and rapid technique can be provided for site-specific editing of the genome of a target sequence.

In the present description, "guide RNA" refers to that which mimics the hairpin structure of tracrRNA-crRNA, and contains in the 5'-terminal region thereof a polynucleotide composed of a base sequence complementary to a base sequence located from 1 to preferably 20 to 24 bases, and more preferably from 1 to preferably 22 to 24 bases, upstream from the PAM sequence in a target double-stranded polynucleotide. Moreover, guide RNA may contain one or more polynucleotides composed of a base sequence allowing the obtaining of a hairpin structure composed of base sequences non-complementary to a target double-stranded polynucleotide symmetrically arranged so as to form a complementary sequence having a single point as the axis thereof.

The guide RNA has a function of binding to the mutant Cas9 protein of the present invention and leading the protein to a target DNA. The guide RNA has a sequence at the 5'-terminal which is complementary to the target DNA, and binds to the target DNA via the complementary sequence, thereby leading the mutant Cas9 protein of the present invention to the target DNA. When the mutant Cas9 protein functions as a DNA endonuclease, the DNA can be cleaved at the site where the target DNA exists and, for example, the function of the target DNA can be specifically lost.

The guide RNA is designed and prepared based on the sequence information of the target DNA to be cleaved or modified. Specific examples include sequences such as those used in the Examples.

In the present description, an "endonuclease" refers to an enzyme that cleaves a nucleotide strand at an intermediate location. Therefore, the Cas9 protein of the present embodiment that recognizes a wide range of PAM sequences and has endonuclease activity has enzyme activity guided by guide RNA that cleaves at an intermediate location of a DNA strand.

In the present description, the terms "polypeptide", "peptide" and "protein" refer to polymers of amino acid residues and are used interchangeably. In addition, these terms also refer to amino acid polymers in which one or a plurality of amino acid residues are in the form of a chemical analog or modified derivative of the corresponding amino acids present in nature.

In the present specification, the "non-aromatic amino acid" means an amino acid not having a benzene ring, such as glutamic acid, alanine, proline, valine, leucine, isoleucine and the like.

In the present description, a "DNA sequence" refers to a nucleotide sequence of an arbitrary length, is a deoxyribonucleotide or ribonucleotide, and may be linear or branched and single-stranded or double-stranded.

In the present description, a "PAM sequence" refers to a sequence present in a target double-stranded polynucleotide that can be recognized by Cas9 protein, and the length and base sequence of the PAM sequence differs according to the bacterial species. A sequence capable of being recognized by the Cas9 protein of the present embodiment capable of recognizing a wide range of PAM sequences can be represented by "5'-NNGNNN-3'.

Furthermore, in the present description, "N" refers to any one base selected from the group consisting of adenine, cytosine, thymine and guanine, "A" refers to adenine, "G" to guanine, "C" to cytosine, "T" to thymine, "R" to a base having a purine skeleton (adenine or guanine), and "Y" to a base having a pyrimidine skeleton (cytosine or thymine).

In the present description, a "polynucleotide" refers to a deoxyribonucleotide or ribonucleotide polymer having linear or cyclic coordination and may be single-stranded or double-stranded, and should not be interpreted as being restricted with respect to polymer length. In addition, polynucleotides include known analogs of naturally-occurring nucleotides as well as nucleotides in which at least one of the base moieties, sugar moieties and phosphate moieties thereof has been modified (such as a phosphorothioate backbone). In general, an analog of a specific nucleotide has the same base-pairing specificity, and for example, A analogs form base pairs with T.

In one embodiment, the present invention provides a protein consisting of an amino acid sequence resulting from mutations of the 985-position and the 991-position, and optionally the 986-position, and at least one, two, three, four, five, six or seven sites selected from the group consisting of the 782-position, the 800-position, the 888-position, the 968-position, the 988-position, the 1017-position and the 1021-position in the amino acid sequence shown in SEQ ID NO: 2, and having a binding ability to guide RNA (embodiment 1). The protein of embodiment 1 has RNA-guided DNA endonuclease activity.

SEQ ID NO: 2 is a full-length amino acid sequence of SaCas9 protein.

The mutation at the 782-position of SEQ ID NO: 2 is specifically substitution of glutamic acid at the 782-position with lysine or arginine, preferably substitution with lysine.

The mutation at the 800-position of SEQ ID NO: 2 is specifically substitution of leucine at the 800-position with arginine or lysine, preferably substitution with arginine.

The mutation at the 888-position of SEQ ID NO: 2 is specifically substitution of asparagine at the 888-position with an amino acid selected from the group consisting of lysine, arginine, asparagine, glutamine, histidine and serine, preferably substitution with lysine.

The mutation at the 968-position of SEQ ID NO: 2 is specifically substitution of asparagine at the 968-position with arginine or lysine, preferably substitution with arginine.

The mutation at the 985-position of SEQ ID NO: 2 is specifically substitution of asparagine at the 985-position with an amino acid selected from the group consisting of alanine, serine, threonine, cysteine, valine and isoleucine, preferably substitution with alanine.

The mutation at the 986-position of SEQ ID NO: 2 is specifically substitution of asparagine at the 986-position with an amino acid selected from the group consisting of alanine, serine, threonine, cysteine, valine and isoleucine, preferably substitution with alanine.

The mutation at the 988-position of SEQ ID NO: 2 is specifically substitution of leucine at the 988-position with histidine.

The mutation at the 991-position of SEQ ID NO: 2 is specifically substitution of arginine at the 991-position with a non-aromatic amino acid, preferably substitution with alanine.

The mutation at the 1017-position of SEQ ID NO: 2 is specifically substitution of isoleucine at the 1017-position with a bulkier amino acid. By substitution with a bulky amino acid, stabilization by interaction with the side chain of arginine at the 1015-position is expected. Examples of the bulky amino acid include phenylalanine, methionine, tyrosine, tryptophan and proline. Preferred is substitution with phenylalanine.

The mutation at the 1021-position of SEQ ID NO: 2 is specifically substitution of alanine at the 1021-position with an amino acid selected from the group consisting of serine, threonine and asparagine, preferably substitution with serine.

In another embodiment of the present invention, the present invention provides a protein further having mutations at the 927-position and the 929-position and having binding ability to guide RNA (embodiment 2) in addition to the mutation of the aforementioned embodiment 1. In addition, the protein of embodiment 2 has RNA-guided DNA endonuclease activity.

The mutation at the 927-position is specifically substitution of threonine at the 927-position with lysine or arginine, preferably substitution with lysine.

The mutation at the 929-position is specifically substitution of lysine at the 929-position with asparagine, aspartic acid or alanine, preferably substitution with asparagine.

In another embodiment of the present invention, the present invention provides a protein further having a mutation at the 929-position and having binding ability to guide RNA (embodiment 3) in addition to the mutation of the aforementioned embodiment 1. The protein of embodiment 3 has RNA-guided DNA endonuclease activity.

The mutation at the 929-position is specifically substitution of lysine at the 929-position with arginine.

In another embodiment of the present invention, the present invention provides a protein having a mutation at the 927-position in addition to the mutation of the aforementioned embodiment 1. The protein of embodiment 4 has RNA-guided DNA endonuclease activity.

The mutation at the 927-position is specifically substitution of threonine at the 927-position with lysine.

In another embodiment of the present invention, the present invention provides a protein having a further mutation at the 889-position in addition to the mutation of the aforementioned embodiment 1, and having a binding ability to guide RNA (embodiment 5). The protein of embodiment 5 has RNA-guided DNA endonuclease activity.

The mutation at the 889-position is specifically substitution of alanine at the 889-position with asparagine, serine, lysine, arginine or histidine, preferably substitution with asparagine.

In another embodiment of the present invention, the present invention provides a protein having further mutations at the 927-position, 929-position and 889-position in addition to the mutation of the aforementioned embodiment 1, and having a binding ability to guide RNA (embodiment 6). The protein of embodiment 6 additionally has RNA-guided DNA endonuclease activity.

The mutation at the 927-position is specifically substitution of threonine at the 927-position with lysine or arginine, preferably lysine.

The mutation at the 929-position is specifically substitution of lysine at the 929-position with asparagine, aspartic acid or alanine, preferably asparagine.

The mutation at the 889-position is specifically substitution with asparagine.

In another embodiment of the present invention, the present invention provides a protein (embodiment 7) that is functionally equivalent to the proteins of the aforementioned embodiments 1-6. To be functionally equivalent to the proteins of the aforementioned embodiments 1-6, the amino acid sequence having identity of 80% or more at a site other than the positions where the mutations have been applied in the SEQ ID NO: 2 in the aforementioned embodiments 1-6 and has a binding ability to guide RNA. When amino acids are increased or decreased due to mutation, the "site other than the positions where the mutations have been applied" can be interpreted to mean a "site other than the positions corresponding to the positions where the mutations have been applied". This identity is preferably 80% or more, more preferably 85% or more, even more preferably 90% or more, particularly preferably 95% or more, and most preferably 99% or more. The amino acid sequence identity can be determined by a method known per se. For example, amino acid sequence identity (%) can be determined using a program conventionally used in the pertinent field (e.g., BLAST, FASTA, etc.) by default. In another aspect, identity (%) is determined by any algorithm known in the pertinent field, such as algorithms of Needleman et al. (1970) (J. Mol. Biol. 48: 444-453), Myers and Miller (CABIOS, 1988, 4: 11-17) and the like. The algorithm of Needleman et al. is incorporated into the GAP program in the GCG software package (available at www.gcg.com) and the identity (%) can be determined using, for example, any of BLOSUM 62 matrix and PAM250 matrix, as well as gap weight: 16, 14, 12, 10, 8, 6 or 4, and length weight: 1, 2, 3, 4, 5 or 6. The algorithm of Myers and Miller is incorporated into the ALIGN program that is a part of the GCG sequence alignment software package. When the ALIGN program is used to compare amino acid sequences, for example, PAM120 weight residue table, gap length penalty 12, and gap penalty 4 can be used.

As a protein functionally equivalent to the proteins of the aforementioned embodiments 1-6, a protein which comprises one to several amino acids substituted, deleted, inserted and/or added at site(s) other than the positions where the mutations have been applied in the SEQ ID NO: 2 in the aforementioned embodiment 1-6 and having the binding ability to guide RNA (embodiment 7) is provided. When amino acids are increased or decreased due to mutation, the "site other than the positions where the mutations have been applied" can be interpreted to mean a "site other than the positions corresponding to the positions where the mutations have been applied".

As a technique for artificially performing "substitution, deletion, insertion and/or addition of amino acid", for example, a method including applying conventional site specific mutation introduction to DNA encoding a predetermined amino acid sequence, and thereafter expressing the DNA by a conventional method can be mentioned. Examples of the site specific mutation introduction method include a method using amber mutation (gapped duplex method, Nucleic Acids Res., 12, 9441-9456 (1984)), a PCR method using a mutation introduction primer and the like.

The number of the amino acids modified above is at least one residue, specifically one or several, or more than that. Among the aforementioned substitution, deletion, insertion and addition, substitution of amino acid is particularly preferred. The substitution is more preferably substitution with an amino acid having similar properties such as hydrophobicity, charge, pK, and characteristic of steric structure and the like. Examples of the substitution include substitution within the groups of i) glycine, alanine; ii) valine, isoleucine, leucine; iii) aspartic acid, glutamic acid, asparagine, glutamine; iv) serine, threonine; v) lysine, arginine; vi) phenylalanine, tyrosine.

In another embodiment of the present invention, the present invention provides a protein having further mutations at the 10-position, the 556-position, the 557-position and/or the 580-position in SEQ ID NO: 2, in addition to the mutations of the aforementioned embodiments 1 to 7, and having a binding ability to guide RNA (embodiment 8). In the present specification, the amino acid residue at the "corresponding position" is identified by comparing the target amino acid sequence with a reference sequence (the amino acid sequence shown in SEQ ID NO: 2) by the use of a known algorithm, and aligning the sequence so as to confer maximum homology to the conserved amino acid residues present in the amino acid sequence of each protein having mutation. By aligning the amino acid sequence of each protein by this method, it is possible to determine the position of the amino acid residue to be mutated in the sequence regardless of the insertion or deletion contained in the amino acid sequence.

The mutation at the 10-position is specifically substitution of the 10-position aspartic acid with alanine or asparagine.

The mutation at the 10-position is specifically substitution of aspartic acid at the 10-position with alanine.

The mutation at the 556-position is specifically substitution of aspartic acid at the 556-position with alanine.

The mutation at the 557-position is specifically substitution of histidine at the 557-position with alanine.

The mutation at the 580-position is specifically substitution of asparagine at the 580-position with alanine.

Preferred as embodiment 8 are a protein in which aspartic acid at the 10-position is substitution with alanine; a protein in which asparagine at the 580-position is substituted with alanine; and a protein in which aspartic acid at the 10-position is substitution with alanine and asparagine at the 580-position is substituted with alanine. The first two proteins have nickase activity, and the third protein binds to guide RNA and led to the target DNA but the endonuclease activity is inactivated.

A preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S), threonine at the 927-position to lysine (T927K), and lysine at the 929-position to asparagine (K929N) in the SEQ ID NO: 2.

In this specification, the alphabet displayed on the left side of the number indicating the number of amino acid residues up to the substitution site indicates a single letter code of the amino acid before substitution of the amino acid sequence of SEQ ID NO: 2, and the alphabet displayed on the right side indicates a single letter code of the amino acid after substitution.

Another preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S), alanine at the 889-position to asparagine (A889N), threonine at the 927-position to lysine (T927K), and lysine at the 929-position to asparagine (K929N) in the SEQ ID NO: 2.

Another preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S) in the SEQ ID NO: 2.

Another preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), arginine at the 991-position to alanine (R991A), alanine at the 1021-position to serine (A1021S), threonine at the 927-position to lysine (T927K), lysine at the 929-position to asparagine (K929N), and isoleucine at the 1017-position to phenylalanine (I1017F) in the SEQ ID NO: 2.

A preferable example of the Cas9 protein recognizing a wide range of the PAM sequence of the present invention is, for example, a protein having an amino acid sequence resulting from mutations of glutamic acid at the 782-position to lysine (E782K), leucine at the 800-position to arginine (L800R), asparagine at the 968-position to arginine (N968R), asparagine at the 985-position to alanine (N985A), asparagine at the 986-position to alanine (N986A), arginine at the 991-position to alanine (R991A), leucine at the 988-position to histidine (L988H), alanine at the 1021-position to serine (A1021S), threonine at the 927-position to lysine (T927K), lysine at the 929-position to asparagine (K929N), aspartic acid at the 10-position to alanine (D10A), and asparagine at the 580-position to alanine (N580A) in the SEQ ID NO: 2.

Another preferable example of the Cas9 protein recognizing a wide range of the PAM sequence of the present invention is, for example, a protein having an amino acid sequence resulting from mutation of glutamic acid at the 782-position to lysine (E782K), leucine at the 800-position to arginine (L800R), asparagine at the 968-position to arginine (N968R), asparagine at the 985-position to alanine (N985A), arginine at the 991-position to alanine (R991A), alanine at the 1021-position to serine (A1021S), threonine at the 927-position to lysine (T927K), lysine at the 929-position to asparagine (K929N), isoleucine at the 1017-position to phenylalanine (I1017F)), aspartic acid at the 10-position to alanine (D10A), and asparagine at the 580-position to alanine (N580A) in the SEQ ID NO: 2.

The Cas9 protein recognizing a wide range of PAM sequences in the present embodiment can be produced according to, for example, the method indicated below. First, a host is transformed using a vector containing a nucleic acid that encodes the aforementioned Cas9 protein of the present invention recognizing a wide range of PAM sequences. Then, the host is cultured to express the aforementioned protein. Conditions such as medium composition, culture temperature, duration of culturing or addition of inducing agents can be determined by a person with ordinary skill in the art in accordance with known methods so that the transformant grows and the aforementioned protein is efficiently produced. In addition, in the case of having incorporated a selection marker in the form of an antibiotic resistance gene in an expression vector, the transformant can be selected by adding antibiotic to the medium. Then, Cas9 protein recognizing a wide range of PAM sequences is obtained by purifying the aforementioned protein expressed by the host according to a method known per se.

There are no particular limitations on the host, and examples thereof include animal cells, plant cells, insect cells and microorganisms such as *Escherichia coli*, *Bacillus subtilis* or yeast.

<Complex of Cas9 Protein Recognizing Wide Range of PMA Sequences and Guide RNA>

In one embodiment thereof, the present invention provides a protein-RNA complex provided with the protein indicated in the previous section on<Cas9 Protein Recognizing Wide Range of PMA Sequences> and guide RNA containing a polynucleotide composed of a base sequence complementary to a base sequence located 1 to 20 to 24 bases upstream from a proto-spacer adjacent motif (PAM) sequence in a target double-stranded polynucleotide.

According to the protein-RNA complex of the present embodiment, a wide range of PMA sequences can be recognized and a target double-stranded polynucleotide can be easily and rapidly edited site-specifically for a target sequence.

The aforementioned protein and the aforementioned guide RNA are able to form a protein-RNA complex by mixing in vitro and in vivo under mild conditions. Mild conditions refer to a temperature and pH of a degree that does not cause proteolysis or denaturation, and the temperature is preferably 4° C. to 40° C., while the pH is preferably 4 to 10.

In addition, the duration of mixing and incubating the aforementioned protein and the aforementioned guide RNA is preferably 0.5 hours to 1 hour. The complex formed by the aforementioned protein and the aforementioned guide RNA is stable and is able to maintain stability even if allowed to stand for several hours at room temperature.

<CRISPR-Cas Vector System>

In one embodiment thereof, the present invention provides a CRISPR-Cas vector system provided with a first vector containing a gene encoding a protein indicated in the previous section on <Cas9 Protein Recognizing Wide Range of PAM Sequences>, and a second vector containing a guide RNA containing a polynucleotide composed of a base sequence complementary to a base sequence located 1 to 20 to 24 bases upstream from PAM sequence in a target double-stranded polynucleotide.

According to the CRISPR-Cas vector system of the present embodiment, a target double-stranded polynucleotide can be easily and rapidly edited site-specifically for a target sequence.

The guide RNA is suitably designed to contain in the 5'-terminal region thereof a polynucleotide composed of a base sequence complementary to a base sequence located from 1 to 20 to 24 bases, and preferably to 22 to 24 bases, upstream from a PAM sequence in a target double-stranded polynucleotide. Moreover, the guide RNA may also contain one or more polynucleotides composed of a base sequence allowing the obtaining of a hairpin structure composed of base sequences is non-complementary to a target double-stranded polynucleotide symmetrically arranged so as to form a complementary sequence having a single point as the axis thereof.

The vector of the present embodiment is preferably an expression vector. There are no particular limitations on the expression vector, and examples thereof that can be used include *E. coli*-derived plasmids such as pBR322, pBR325, puCl2 or puC13; *B. subtilis*-derived plasmids such as pUB110, pTPS or pC194; yeast-derived plasmids such as pSH19 or pSH15; bacteriophages such as yphages; viruses such as adenovirus, adeno-associated virus, lentivirus, vaccinia virus or baculovirus; and modified vectors thereof.

In the aforementioned expression vector, there are no particular limitations on the promoters for expression of the aforementioned Cas9 protein or the aforementioned guide RNA, and examples thereof that can be used include promoters for expression in animal cells such as EFla promoter, SRa promoter, SV40 promoter, LTR promoter, cytomegalovirus (CMV) promoter or HSV-tk promoter, promoters for expression in plant cells such as the 35S promoter of cauliflower mosaic virus (CaMV) or rubber elongation factor (REF) promoter, and promoters for expression in insect cells such as polyhedrin promoter or p10 promoter. These promoters can be suitably selected according to the aforementioned Cas9 protein and the aforementioned guide RNA, or the type of cells expressing the aforementioned Cas9 protein and the aforementioned guide RNA.

The aforementioned expression vector may also further have a multi-cloning site, enhancer, splicing signal, polyadenylation signal, selection marker or replication origin and the like.

<Method for Site-Specifically Modifying Target Double-Stranded Polynucleotide>

First Embodiment

In one embodiment thereof, the present invention provides a method for site-specifically modifying a target double-stranded polynucleotide, provided with:

a step for mixing and incubating a target double-stranded polynucleotide, a protein and a guide RNA, and a step for having the aforementioned protein modify the aforementioned target double-stranded polynucleotide at a binding site located upstream of a PAM sequence; wherein, the aforementioned target double-stranded polynucleotide has a PAM sequence composed of NNGNNN (wherein, N represents any base and G represents guanine), the aforementioned protein is the protein indicated in the above-mentioned <Cas9 Protein Recognizing Wide Range of PMA Sequences>, and the aforementioned guide RNA contains a polynucleotide composed of a base sequence complementary to a base sequence located 1 to 20 to 24 bases upstream from the aforementioned PAM sequence in the aforementioned target double-stranded polynucleotide.

According to the method of the present embodiment, a target double-stranded polynucleotide can be modified easily, rapidly and site-specifically for a target sequence by using mutant Cas9 protein recognizing a wide range of PAM sequences.

In the present embodiment, there are no particular limitations on the target double-stranded polynucleotide provided it has a PAM sequence composed of NNGNNN (wherein, N represents any base and G represents guanine).

In the present embodiment, the protein and guide RNA are as indicated in the previous section on<Cas9 Protein Recognizing Wide Range of PMA Sequences>.

The following provides a detailed explanation of the method for site-specifically modifying a target double-stranded polynucleotide.

First, the aforementioned protein and the aforementioned guide RNA are mixed and incubated under mild conditions. Mild conditions are as previously described. The incubation time is preferably 0.5 hours to 1 hour. A complex formed by the aforementioned protein and the aforementioned guide RNA is stable and is able to maintain stability even if allowed to stand for several hours at room temperature.

Next, the aforementioned protein and the aforementioned guide RNA form a complex on the aforementioned target double-stranded polynucleotide. The aforementioned protein recognizes PAM sequences, and binds to the aforementioned target double-stranded polynucleotide at a binding site located upstream of the PAM sequence. When the aforementioned protein has an endonuclease activity, the polynucleotide is cleaved at this site. As a result of the Cas9 protein recognizing the PAM sequence, and the double helix structure of the target double-stranded polynucleotide being pulled apart starting at the PAM sequence and annealing with a base sequence complementary to the target double-stranded polynucleotide in the guide RNA, the double helix structure of the target double-stranded polynucleotide is partially unraveled. At this time, the aforementioned Cas9 protein cleaves phosphate diester bonds of the target double-stranded polynucleotide at a cleavage site located upstream of the PAM sequence and a cleavage site located upstream of a sequence complementary to the PAM sequence.

Second Embodiment

In the present embodiment, an expression step may be further provided prior to the incubation step in which the protein indicated in the previous section on<Cas9 Protein Recognizing Wide Range of PAM Sequences> and guide RNA are expressed using the previously described CRISPR-Cas vector system.

In the expression step of the present embodiment, Cas9 protein and guide RNA are first expressed using the aforementioned CRISPR-Cas vector system. A specific expression method consists of transforming a host using an expression vector containing a gene that encodes Cas9 protein and an expression vector containing guide RNA, respectively. Then, the host is cultured to express the Cas9 protein and guide RNA. Conditions such as medium composition, culture temperature, duration of culturing or addition of inducing agents can be determined by a person with ordinary skill in the art in accordance with known methods so that the transformant grows and the aforementioned protein is efficiently produced. In addition, in the case of having incorporated a selection marker in the form of an antibiotic resistance gene in the expression vector, the transformant can be selected by adding antibiotic to the medium. Then, the Cas9 protein and guide RNA are obtained by purifying the Cas9 protein and guide RNA expressed by the host according to a suitable method.

<Method for Site-Specifically Modifying Target Double-Stranded Polynucleotide>

First Embodiment

In one embodiment thereof, the present invention provides a method for site-specifically modifying a target double-stranded polynucleotide, provided with:
a step for mixing and incubating a target double-stranded polynucleotide, a protein and a guide RNA, a step for having the protein bind with the target double-stranded polynucleotide at a binding site located upstream of a PAM sequence, and a step for obtaining a modified target double-stranded polynucleotide in a region determined by complementary binding between the guide RNA and the target double-stranded polynucleotide; wherein,
the aforementioned protein is the protein indicated in the previous section on the aforementioned <Cas9 Protein Recognizing Wide Range of PAM Sequences>, and
the aforementioned guide RNA contains a polynucleotide composed of a base sequence complementary to a base sequence located 1 to 20 to 24 bases upstream from the aforementioned PAM sequence in the aforementioned target double-stranded polynucleotide.

According to the method of the present embodiment, a target double-stranded polynucleotide can be modified easily, rapidly and site-specifically for a target sequence by using an RNA-guided DNA endonuclease improved in binding ability to guide RNA and cleavage activity.

In the present embodiment, the target double-stranded polynucleotide, protein and guide RNA are as indicated in the previous sections on<Cas9 Protein Recognizing Wide Range of PMA Sequences> and <Method for Site-Specifically Modifying Target Double-Stranded Polynucleotide>.

The following provides a detailed explanation of the method for site-specifically modifying a target double-stranded polynucleotide. The steps through site-specifically bind to a target double-stranded polynucleotide are the same as in the previous section on<Method for Site-Specifically Cleaving Target Double-Stranded Polynucleotide>. Then, a target double-stranded polynucleotide that has been modified as necessary in a region determined by complementary binding between the guide RNA and the target double-stranded polynucleotide is obtained.

In the present description, "modification" refers to a change in the base sequence of a target double-stranded polynucleotide. Examples thereof include cleavage of a target double-stranded polynucleotide, modification of the base sequence of a target double-stranded polynucleotide by inserting an exogenous sequence following cleavage (by physical insertion or insertion by replicating through homology-directed repair), and modification of the base sequence of a target double-stranded polynucleotide by non-homologous end-joining (NHEJ: rejoining the ends of DNA resulting from cleavage) following cleavage, as well as addition of functional protein or base sequence and the like.

Modification of a target double-stranded polynucleotide in the present embodiment makes it possible to introduce a mutation into the target double-stranded polynucleotide or disrupt or modify the function of the target double-stranded polynucleotide.

Second Embodiment

In the present embodiment, an expression step may be further provided prior to the incubation step in which the protein indicated in the previous section on<Cas9 Protein Recognizing Wide Range of PAM Sequences> and guide RNA are expressed using the previously described CRISPR-Cas vector system.

In the expression step of the present embodiment, Cas9 protein and guide RNA are first expressed using the aforementioned CRISPR-Cas vector system. The specific expression method is similar to the method exemplified in the second embodiment in the previous section on<Method for Site-Specifically Modifying Target Double-Stranded Polynucleotide>.

<Method for Site-Specifically Modifying Target Double-Stranded Polynucleotide in Cells>

In one embodiment thereof, the present invention provides a method for site-specifically modifying a target double-stranded polynucleotide in cells, provided with:
a step for introducing the previously described CRISPR-Cas9 vector system into a cell and expressing protein indicated in the previous section on<Cas9 Protein Recognizing Wide Range of PAM Sequences> and guide RNA, a step for having the aforementioned protein bind with the aforementioned target double-stranded polynucleotide at a binding site located upstream of a PAM sequence, and a step for obtaining a modified target double-stranded polynucleotide in a region determined by complementary binding between the aforementioned guide RNA and the aforementioned target double-stranded polynucleotide; wherein, the aforementioned guide RNA contains a polynucleotide composed of a base sequence complementary to a base sequence located 1 to 20 to 24 bases upstream from the aforementioned PAM sequence in the aforementioned target double-stranded polynucleotide.

In the expression step of the present embodiment, first, Cas9 protein and guide RNA are expressed in a cell using the aforementioned CRISPR-Cas vector system.

Examples of organisms serving as the origin of the cells targeted for application of the method of the present embodiment include prokaryote, yeast, animal, plant, insect and the like. There are no particular limitations on the aforementioned animals, and examples thereof include, but are not limited to, human, monkey, dog, cat, rabbit, swine, bovine, mouse, rat and the like. In addition, the type of organism serving as the source of the cells can be arbitrarily selected according to the desired type or objective of the target double-stranded polynucleotide.

Examples of animal-derived cells targeted for application of the method of the present embodiment include, but are not limited to, germ cells (such as sperm or ova), somatic cells composing the body, stem cells, progenitor cells, cancer cells isolated from the body, cells isolated from the body that are stably maintained outside the body as a result of having become immortalized (cell line), and cells isolated from the body for which the nuclei have been artificially replaced.

Examples of somatic cells composing the body include, but are not limited to, cells harvested from arbitrary tissue such as the skin, kidneys, spleen, adrenals, liver, lungs, ovaries, pancreas, uterus, stomach, small intestine, large intestine, urinary bladder, prostate gland, testes, thymus, muscle, connective tissue, bone, cartilage, vascular tissue, blood, heart, eyes, brain or neural tissue. Specific examples of somatic cells include, but are not limited to, fibroblasts, bone marrow cells, immunocytes (e.g., B lymphocytes, T lymphocytes, neutrophils, macrophages or monocytes etc.), erythrocytes, platelets, osteocytes, bone marrow cells, pericytes, dendritic cells, keratinocytes, adipocytes, mesenchymal cells, epithelial cells, epidermal cells, endothelial cells, intravascular endothelial cells, lymphatic endothelial cells, hepatocytes, pancreatic islet cells (e.g., a cells, β cells, δ cells, ε cells or PP cells etc.), chondrocytes, cumulus cells, glia cells, nerve cells (neurons), oligodendrocytes, microglia cells, astrocytes, cardiomyocytes, esophageal cells, muscle cells (e.g., smooth muscle cells or skeletal muscle cells etc.), melanocytes and mononuclear cells, and the like.

Stem cells refer to cells having both the ability to self-replicate as well as the ability to differentiate into a plurality of other cell lines. Examples of stem cells include, but are not limited to, embryonic stem cells (ES cells), embryonic tumor cells, embryonic germ stem cells, induced pluripotent stem cells (iPS cells), neural stem cells, hematopoietic stem cells, mesenchymal stem cells, hepatic stem cells, pancreatic stem cells, muscle stem cells, germ stem cells, intestinal stem cells, cancer stem cells and hair follicle stem cells, and the like.

Cancer cells are cells derived from somatic cells that have acquired reproductive integrity. Examples of the origins of cancer cells include, but are not limited to, breast cancer (e.g., invasive ductal carcinoma, ductal carcinoma in situ, inflammatory breast cancer etc.), prostate cancer (e.g., hormone-dependent prostate cancer or non-hormone dependent prostate cancer etc.), pancreatic cancer (e.g., pancreatic ductal carcinoma etc.), stomach cancer (e.g., papillary adenocarcinoma, mucinous carcinoma, adenosquamous carcinoma etc.), lung cancer (e.g., non-small cell lung cancer, small cell lung cancer, malignant mesothelioma etc.), colorectal cancer (e.g., gastrointestinal stromal tumor etc.), rectal cancer (e.g., gastrointestinal stromal tumor etc.), colorectal cancer (e.g., familial colorectal cancer, hereditary non-polyposis colorectal cancer, gastrointestinal stromal tumor etc.), small intestinal cancer (e.g., non-Hodgkin's lymphoma, gastrointestinal stromal tumor etc.), esophageal cancer, duodenal cancer, cancer of the tongue, pharyngeal cancer (e.g., nasopharyngeal carcinoma, oropharyngeal carcinoma, hypopharyngeal carcinoma etc.), head and neck cancer, salivary gland cancer, brain tumor (e.g., pineal astrocytoma, pilocytic astrocytoma, diffuse astrocytoma, anaplastic astrocytoma etc.), schwannoma, liver cancer (e.g., primary liver cancer, extrahepatic bile duct cancer etc.), kidney cancer (e.g., renal cell carcinoma, transitional cell carcinoma of the renal pelvis and ureter etc.), gall bladder cancer, bile duct cancer, pancreatic cancer, endometrial carcinoma, cervical cancer, ovarian cancer (e.g., epithelial ovarian cancer, extragonadal germ cell tumor, ovarian germ cell tumor, ovarian low malignant potential tumor etc.), bladder cancer, urethral cancer, skin cancer (e.g., intraocular (ocular) melanoma, Merkel cell carcinoma etc.), Hemangioma, malignant lymphoma (e.g., reticulum cell sarcoma, lymphosarcoma, Hodgkin's etc.), melanoma (malignant melanoma), thyroid cancer (e.g., medullary thyroid cancer etc.), parathyroid cancer, nasal cancer, paranasal cancer, bone tumor (e.g., osteosarcoma, Ewing's tumor, uterine sarcoma, soft tissue sarcoma etc.), metastatic medulloblastoma, vascular fibroma, protuberant dermatofibrosarcoma, retinal sarcoma, penile cancer, testicular cancer, pediatric solid tumor (e.g., Wilms tumor or pediatric kidney tumor etc.), Kaposi's sarcoma, AIDS-induced Kaposi's sarcoma, maxillary sinus tumor, fibrous histiocytoma, leiomyosarcoma, rhabdomyosarcoma, chronic myeloproliferative disease and leukemia (e.g., acute myeloid leukemia, acute lymphoblastic leukemia etc.).

Cell lines refer to cells that have acquired reproductive integrity through artificial manipulation ex vivo. Examples of cell lines include, but are not limited to, HCT116, Huh7, HEK293 (human embryonic kidney cells), HeLa (human cervical cancer cell line), HepG2 (human liver cancer cell line), UT7/TPO (human leukemia cell line), CHO (Chinese hamster ovary cell line), MDCK, MDBK, BHK, C-33A, HT-29, AE-1, 3D9, NsO/1, Jurkat, NIH3T3, PC12, S2, Sf9, Sf21, High Five and Vero.

Introduction of the CRISPR-Cas vector system into cells can be carried out using a method suitable for the viable cells used, and examples thereof include electroporation method, heat shock method, calcium phosphate method, lipofection method, DEAE dextran method, microinjection method, particle gun method, methods using viruses, and methods using commercially available transfection reagents such as FuGENE (registered trade mark) 6 Transfection Reagent (manufactured by Roche), Lipofectamine 2000 Reagent (manufactured by Invitrogen Corp.), Lipofectamine LTX Reagent (manufactured by Invitrogen Corp.) or Lipofectamine 3000 Reagent (manufactured by Invitrogen Corp.).

Then, the modification step is the same as the methods indicated in the first embodiment in the previous section on <Method for Site-Specifically Modifying Target Double-Stranded Polynucleotide>.

Modification of a target double-stranded polynucleotide in the present embodiment makes it possible to obtain cells in which a mutation has been introduced into the target double-stranded polynucleotide or the function of the target double-stranded polynucleotide has been disrupted and modified.

When an embodiment having no endonuclease activity is used as the mutant Cas9 protein of the present invention, the protein can bind to the aforementioned target double-stranded polynucleotide at a binding site located upstream of the PAM sequence but cannot remain there to cleave the double-stranded polynucleotide. Therefore, for example, when a labeled protein such as a fluorescent protein (e.g., GFP) is fused to the protein, the labeled protein can be bound to the target double-stranded polynucleotide via the guide RNA-mutant Cas9 protein. By appropriately selecting a substance to be bound to the mutant Cas9 protein, various functions can be imparted to the target double-stranded polynucleotide.

Furthermore, a transcriptional regulatory protein or domain can be linked to the N-terminal or C-terminal of the mutant Cas9 protein. Examples of the transcriptional regulator or domain thereof include transcriptional activator or domain thereof (e.g., VP64, NF-κB p65) and transcription silencer or domain thereof (e.g., heterochromatin protein 1 (HP1)) and transcription inhibitory factor or domain thereof (e.g., Kruppel associated box (KRAB), ERF repressor domain (ERD), mSin3A interacting domain (SID)).

Enzymes that modify the methylation state of DNA (e.g., DNA methyltransferase (DNMT), TET) and enzymes that modify histone subunits (e.g., histone acetyltransferase (HAT), histone deacetylase (HDAC), histone methyltransferase, histone demethylase) can also be linked.

<Gene Therapy>

In one embodiment thereof, the present invention provides a method and composition for gene therapy by carrying out genome editing. In contrast to previously known methods for targeted gene recombination, the method of the present embodiment can be carried out efficiently and inexpensively and can be applied to any cell or living organism. An arbitrary segment of a double-stranded nucleic acid of a cell or living organism can be modified by the gene therapy method of the present embodiment. The gene therapy method of the present embodiment utilizes both homologous and non-homologous recombination processes present in all cells.

In the present description, the term "genome editing" refers to a novel gene modification technology for carrying out a specific gene disruption or knock-in of a reporter gene by carrying out targeted recombination or targeted mutation using a technology such as the CRISPR/Cas9 system or transcription activator-like effector nucleases (TALEN).

In addition, in one embodiment thereof, the present invention provides a gene therapy method for carrying out targeted DNA insertion or targeted DNA deletion. This gene therapy method includes a step for transforming a cell using a nucleic acid construct containing donor DNA. The scheme relating to DNA insertion or DNA deletion after cleaving a target gene can be determined by a person with ordinary skill in the art in accordance with a known method.

In addition, in one embodiment thereof, the present invention provides a gene therapy method for carrying out gene manipulation at a specific genetic locus using both somatic cells and germ cells.

In addition, in one embodiment thereof, the present invention provides a gene therapy method for disrupting a gene in a somatic cell. Here, the gene expresses a product harmful to cells or living organisms by over-expressing a substance harmful to cells or living organisms. This type of gene is over-expressed in one or more cell types generated in a disease. Disruption of the aforementioned over-expressed gene by the gene therapy method of the present embodiment is able to bring about a more favorable state of health in an individual suffering from a disease attributable to the aforementioned over-expressed gene. Namely, therapeutic effects are manifested as a result of the gene being disrupted in only a very small proportion of cells, thereby leading to a reduction in the expression level thereof.

In addition, in one embodiment thereof, the present invention provides a gene therapy method for disrupting a gene in a germ cell. Cells in which a specific gene has been disrupted can be used to create living organisms that do not have the function of a specific gene. A gene can be completely knocked out in cells in which the aforementioned gene has been disrupted. This functional deficit in a specific cell can have a therapeutic effect.

In addition, in one embodiment thereof, the present invention provides a gene therapy method for inserting a donor DNA encoding a gene product. This gene product has a therapeutic effect in the case of having been constitutively expressed. An example of such a method consists of inserting donor DNA encoding an active promoter and insulin gene into an individual suffering from diabetes in order to induce insertion of the donor DNA in an individual group of pancreas cells. Next, the aforementioned individual group of pancreas cells containing the aforementioned donor DNA produces insulin making it possible to treat the diabetes patient. Moreover, a drug-related gene product can be made to be produced by inserting the aforementioned donor DNA into a plant. A gene of a protein product (such as insulin, lipase or hemoglobin) is inserted into the plant along with a control element (constitutively activated promoter or inducible promoter) to enable a large amount of a pharmaceutical to be produced in the plant. Next, this protein product is isolated from the plant.

Transgenic plants or transgenic animals can be produced by methods using nucleic acid transfer technology (McCreath, K. J. et al. (2000), Nature 405: 1066-1069; Polejaeva, I. A. et al. (2000), Nature 407: 86-90). A tissue type-specific vector or cell type-specific vector can be used to provide gene expression only in selected cells.

In addition, in the case of using the aforementioned method in germ cells, cells can be produced having a designed genetic modification by inserting donor DNA into a target gene and allowing all of the subsequent cells to undergo cell division.

Examples of application targets of the gene therapy method of the present embodiment include, but are not limited to, any living organisms, cultured cells, cultured tissue, cultured nuclei (including cells, tissue or nuclei able to be used to regenerate a living organism in cultured cells, cultured tissue or intact cultured nuclei) and gametes (e.g., ova or sperm in various stages of development).

Examples of the origins of cells targeted for application of the gene therapy method of the present embodiment include, but are not limited to, any living organisms (such as insect, fungi, rodent, bovine, sheep, goat, chicken and other agriculturally important animal along with other mammals (e.g., dog, cat or human, although not limited thereto)).

Moreover, the gene therapy method of the present embodiment can be used in plants. There are no particular limitations on those plants targeted for application of the gene therapy method of the present embodiment, and the gene therapy method of the present embodiment can be applied to various arbitrary plant species (e.g., monocotyledons or dicotyledons etc.).

While the present invention is explained in more detail in the following by referring to Examples, they do not limit the scope of the present invention.

EXAMPLE

Example 1: Evaluation of DNA Cleavage Activity of Mutant SaCas9

1. Preparation of Wild-Type and Mutant SaCas9
(1) Construct Design

Wild-type or mutant SaCas9 gene with codon optimized by gene synthesis was incorporated in pESUMO vector (Novagen). Moreover, a TEV recognition sequence was added between His tag and the SaCas9 gene. The design of the construct was such that six consecutive histidine residues (His tag) were linked followed by the addition of the TEV protease recognition site to the N-terminal of the Cas9 expressed by the completed construct.

The base sequences of the SaCas9 genes used are as follows.

base sequence of wild-type SaCas9: SEQ ID NO: 1
base sequence of mutant SaCas9(V11_E782K_L800R_A889R_N968R_N985A_N986A_L988H_R991A_A1021S): a base sequence resulting from conversion of gag at the 2344-2346-position to aaa, ctg at the 2398-2400-position to cgt, gcc at the 2665-2667-position to cgt, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.
base sequence of mutant SaCas9(V11a(+N785W)__E782K_N785W_L800R_A889R_N968R_N985A_N986A_L988H_R991A_A1021S): a base sequence resulting from further conversion of aat at the 2353-2355-position to tgg in the base sequence of V11.
base sequence of mutant SaCas9(V11b(+N785Y)_E782K_N785Y_L800R_A889R_N968R_N985A_N986A_L988H_R991A_A1021S): a base sequence resulting from further conversion of aat at the 2353-2353-position to tat in the base sequence of V11.
base sequence of mutant SaCas9(V11c(+N785S)_E782K_N785S_L800R_A889R_N968R_N985A_N986A_L988H_R991A_A1021S): a base sequence resulting from further conversion of aat at the 2353-2353-position to agc in the base sequence of V11.
base sequence of mutant SaCas9(V11d(+N888H)_E782K_L800R_N888H_A889R_N968R_N985A_N986A_L988H_R991A_A1021S): a base sequence resulting from further conversion of aat at the 2362-2364-position to cat in the base sequence of V11.
base sequence of mutant SaCas9(V11e(+N888R)_E782K_L800R_N888R_A889R_N968R_N985A_N986A_L988H_R991A_A1021S): a base sequence resulting from further conversion of aat at the 2362-2364-position to cgt in the base sequence of V11.
base sequence of mutant SaCas9(V11f(N985S)_E782K_L800R_A889R_N968R_N985S_N986A_L988H_R991A_A1021S): a base sequence resulting from conversion of gcg at the 2953-2955-position to tct in the base sequence of V11.
base sequence of mutant SaCas9(V11g(N985V)_E782K_L800R_A889R_N968R_N985V_N986A_L988H_R991A_A1021S): a base sequence resulting from conversion of gcg at the 2953-2955-position to gtg in the base sequence of V11.
base sequence of mutant SaCas9(V11h(N985L)_E782K_L800R_A889R_N968R_N985L_N986A_L988H_R991A_A1021S): a base sequence resulting from conversion of gcg at the 2953-2955-position to ctg in the base sequence of V11.
base sequence of mutant SaCas9(V11i(N985M)_E782K_L800R_A889R_N968R_N985M_N986A_L988H_R991A_A1021S): a base sequence resulting from conversion of gcg at the 2953-2955-position to atg in the base sequence of V11.
base sequence of mutant SaCas9(V11j(N985I)_E782K_L800R_A889R_N968R_N985I_N986A_L988H_R991A_A1021S): a base sequence resulting from conversion of gcg at the 2953-2955-position to att in the base sequence of V11.
base sequence of mutant SaCas9(V11k(+N995R)_E782K_L800R_A889R_N968R_N985A_N986A_L988H_R991A_N995R_A1021S): a base sequence resulting from further conversion of aat at the 2983-2985-position to cgt in the base sequence of V11.
base sequence of mutant SaCas9(V11l(+N995K)_E782K_L800R_A889R_N968R_N985A_N986A_L988H_R991AN995KA1021S): a base sequence resulting from further conversion of aat at the 2983-2985-position to aaa in the base sequence of V11.
base sequence of mutant SaCas9(V11m(+K910R)_E782K_L800R_A889R_K910R_N968R_N985A_N986A_L988H_R991A_A1021S): a base sequence resulting from further conversion of aag at 2728-2730 to cgt in the base sequence of V11.
base sequence of mutant SaCas9(V11n(A889A)_E782K_L800R_N968R_N985A_N986A_L988H_R991A_A021S): a base sequence resulting from conversion of cgt at the 2665-2667-position to gcg (returned to wild-type) in the base sequence of V11.
base sequence of mutant SaCas9(V11o(A889A_+T927K)_E782K_L800R_T927K_N968R_N985A_N986A_L988H_R991A_A1021S): a base sequence resulting from conversion of cgt at the 2665-2667-position to gcg (returned to wild-type), and further conversion of act at the 2779-2781-position to aaa in the base sequence of V11.
base sequence of mutant SaCas9(V11p(A889A_+T927K+K929A)_E782K_L800R_T927K_K929A_N968R_N985A_N986A_L988H_R991A_A1021S): a base sequence resulting from conversion of cgt at the 2665-2667-position to gcg (returned to wild-type), and further conversion of act at the 2779-2781-position to aaa, and aag at the 2785-2787-position to gcg in the base sequence of V11.

base sequence of mutant SaCas9(V11q(A889A_+K929R)_E782K_L800R_K929R_N968R_N985A_N986A_L988H_R991A_A1021S): a base sequence resulting from conversion of cgt at the 2665-2667-position to gcg (returned to wild-type), and aag at the 2785-2787-position to cgt in the base sequence of V11.

base sequence of mutant SaCas9(V11r(+T927K)_E782K_L800R_A889R_T927K_N968R_N985A_N986A_L988H_R991A_A1021S): a base sequence resulting from further conversion of act at the 2779-2781-position to aaa in the base sequence of V11.

base sequence of mutant SaCas9(V11s(+1(929R))_E782K_L800R_A889R_K929R_N968R_N985A_N986A_L988H_R991A_A1021S): a base sequence resulting from further conversion of aag at the 2785-2787-position to cgt in the base sequence of V11.

base sequence of mutant SaCas9(V11t(K929A)_E782K_L800R_A889R_T927A_N968R_N985A_N986A_L988H_R991A_A1021S): a base sequence resulting from further conversion of aag at the 2785-2787-position to gcg in the base sequence of V11.

base sequence of mutant SaCas9(V12_E782K_L800R_N888K_A889R_N968R_N985A_N986A_L988H_R991A_A1021S): a base sequence resulting from conversion of gag at the 2344-2346-position to aaa, ctg at the 2398-2400-position to cgt, aat at the 2662-2664-position to aaa, gcc at the 2665-2667-position to cgt, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V15_E782K_L800R_T927K_K929N_N968R_N985A_N986A_L988H_R991A_A1021S): a base sequence resulting from conversion of gag at the 2344-2346-position to aaa, ctg at the 2398-2400-position to cgt, act at the 2779-2781-position to aaa, aag at the 2785-2787-position to aac, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base SEQ ID NO: 1.

base sequence of mutant SaCas9(V15a(+N785S)_E782K_N785S_L800R_T927K_K929N_N968R_N985A_N986A_L988H_R991A_A1021S): a base sequence resulting from further conversion of aat at the 2353-2355-position to agc in the base sequence of V15.

base sequence of mutant SaCas9(V15b(+N888H)_E782K_L800R_N888H_T927K_K929N_N968R_N985A_N986A_L988H_R991A_A1021S): a base sequence resulting from further conversion of aat at the 2662-2664-position to cat in the base sequence of V15.

base sequence of mutant SaCas9(V15c(+N888K)_E782K_L800R_N888K_T927K_K929N_N968R_N985A_N986A_L988H_R991A_A1021S): a base sequence resulting from further conversion of aat at the 2662-2664-position to aaa in the base sequence of V15.

base sequence of mutant SaCas9(V15d(+A889S)_E782K_L800R_A889S_T927K_K929N_N968R_N985A_N986A_L988H_R991A_A1021S): a base sequence resulting from further conversion of gcg at the 2665-2667-position to tct in the base sequence of V15.

base sequence of mutant SaCas9(V15e(K929L)_E782K_L800R_T927K_K929L_N968R_N985A_986A_L988H_R991A_A1021S): a base sequence resulting from conversion of aac at the 2785-2787-position to ctg in the base sequence of V15.

base sequence of mutant SaCas9(V15f(N929I)_E782K_L800R_T927K_N929I_N968R_N985A_N986A_L988H_R991A_A1021S): a base sequence resulting from conversion of aac at the 2785-2787-position to atc in the base sequence of V15.

base sequence of mutant SaCas9(V16_E782K_L800R_A889N_T927K_K929N_N968R_N985A_N986A_L988H_R991A_A1021S): a base sequence resulting from conversion of gag at the 2344-2346-position to aaa, ctg at the 2398-2400-position to cgt, gcc at the 2665-2667-position to aac, act at the 2779-2781-position to aaa, aag at the 2785-2787-position to aac, aac at the 2902-290 the 4-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V17_E782K_L800R_T927K_K929D_N968R_N985A_N986A_L988H_R991A_A1021S): a base sequence resulting from conversion of gag at the 2344-2346-position to aaa, ctg at the 2398-2400-position to cgt, act at the 2779-2781-position to aaa, aag at the 2785-2787-position to gat, aac at the 2902-2904-position to cgt, aac at the 2953-2955-position to gcg, aat at the 2956-2958-position to gcg, ctg at the 2962-2964-position to cac, cgc at the 2971-2973-position to gcg, and gcc at the 3061-3063-position to tct in the base sequence of SEQ ID NO: 1.

base sequence of mutant SaCas9(V43_E782K_L800R_T927K_K929N_N968R_N985A_R991A_A1021S): a base sequence resulting from conversion of gag at the 2344-2346-position to aaa, ctg at the 2398-2400-position to cgt, act at the 2779-2781-position to aaa, aag at the 2785-2787-position to aac, aac at the 2902-2904-position to cgt, aac at the 2953-2955-position to gcg, cgc at the 2971-2973-position to gcg, and gcc at the 3061-3063-position to tct in the base sequence of SEQ ID NO: 1.

base sequence of mutant SaCas9(V51_E782K_L800R_T927K_K929N_N968R_N985A_R991A_1021S_I1017F): a base sequence resulting from conversion of atc at the 3049-3051-position to ttc in the base sequence of V43.

(2) The resulting vectors were used to transform *Escherichia coli* strain rosetta 2 (DE3). Subsequently, the *E. coli* were cultured in LB medium containing 20 μg/ml of kanamycin. After having cultured to OD=0.8, isopropyl-β-D-1-thiogalactopyranoside (IPTG) (final concentration: 0.5 mM) as an expression inducing agent was added followed by culturing for 20 hours at 20° C. Following culturing, the *E. coli* were recovered by centrifugation (8,000 g, 10 min).

(3) Purification of Wild-Type and Mutant SaCas9

The bacterial cells recovered in (2) were suspended in a Buffer A and subjected to ultrasonication. Supernatant was recovered by centrifugation (25,000 g, 30 min) followed by mixing with Mg-His beads equilibrated with Buffer A and gently admixing for 1 hour. After recovering the unadsorbed fraction, the column was washed once with Buffer A. It was washed once with buffer B with high salt concentration, after which washed once with high concentration buffer A. Finally, the target protein was eluted with a Buffer C with high imidazole concentration.

The compositions of Buffers A to C are shown below.

Buffer A: 20 mM Tris-HCl, pH 8.0, 300 mM NaCl, 20 mM imidazole

Buffer B: 20 mM Tris-HCl, pH 8.0, 1000 mM NaCl, 20 mM imidazole

Buffer C: 20 mM Tris-HCl, pH 8.0, 300 mM NaCl, 300 mM imidazole

2. Preparation of Guide RNA

A vector inserted with the target guide RNA sequence was prepared. A T7 promoter sequence was added upstream from the guide RNA sequence followed by incorporating a linearized pUC119 vector (Takara Corp.). Template DNA for an in vitro transcription reaction was produced using PCR based on the resulting vector. An in vitro transcription reaction was carried out by T7 RNA polymerase for 4 hours at 37° C. using this DNA template. The transcription product was purified by RNeasy. The base sequence consisting of a guide sequence and a scaffold is shown in SEQ ID NO: 3.

3. Plasmid DNA Cleavage Activity Measurement Test

Vectors inserted with the target DNA sequence and PAM sequence (5'-NNGAAA-3') were prepared for use in a DNA cleavage activity measurement test. PAM sequences were each added to the target DNA sequence and incorporated in a linearized pUC119 vector (SEQ ID NO: 4).

*Escherichia coli* strain Mach1 (Life Technologies) was transformed using the prepared vectors followed by culturing at 37° C. in LB medium containing 20 µg/mL of ampicillin.

Following culturing, the bacterial cells were recovered by centrifugation (8,000 g, 1 min) and the plasmid DNA was purified using the QIAprep Spin Miniprep Kit (QIAGEN).

A cleavage experiment was carried out using the purified target plasmid DNA containing PAM sequence. The plasmid DNA was linearized into a single strand with restriction enzyme. When the wild-type or mutant SaCas9 was cleaved from the target DNA sequence in this linearized DNA, approximately 1000 bp and 2000 bp cleavage products were obtained. As the buffer for cleavage, cleavage buffer B with the following composition was used.

Composition of Cleavage Buffer B (×10)

200 mM HEPES 7.5
1000 mM KCl
50% glycerol
10 mM DTT
5 mM EDTA
20 mM $MgCl_2$

Figure 2:
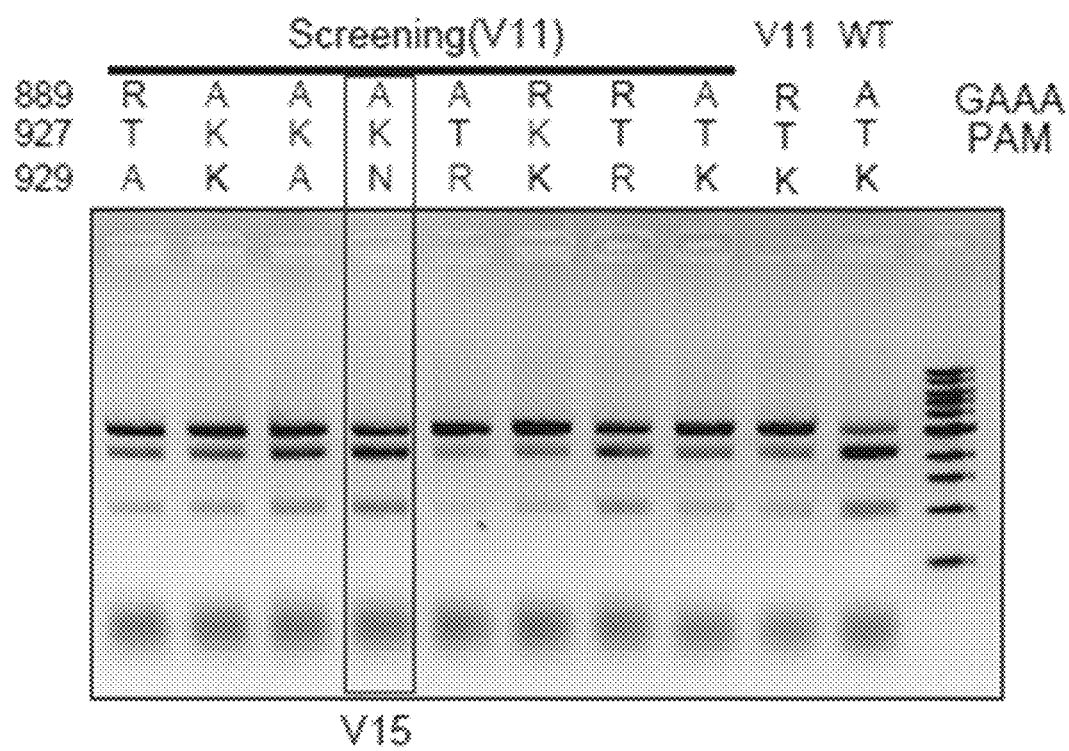
FIG. 2 shows an image representing the results of agarose gel electrophoresis in a DNA cleavage activity measurement test in Example 1. "(NN)GAAA" was used as the PAM sequence.
Figure 3:
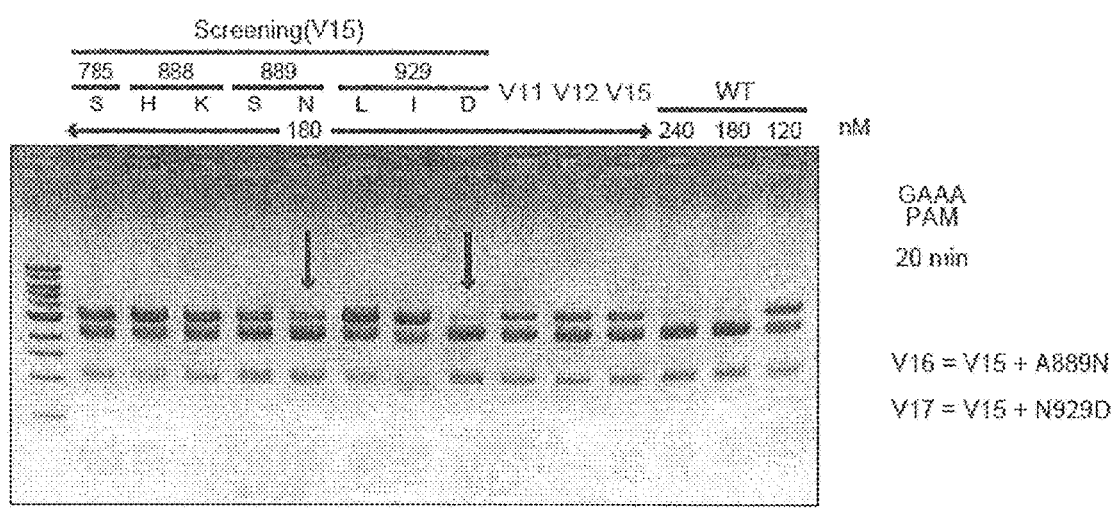
FIG. 3 shows an image representing the results of agarose gel electrophoresis in a DNA cleavage activity measurement test in Example 1. "(NN)GAAA" was used as the PAM sequence.

The samples after reaction were electrophoresed using 1% concentration of agarose gel, and bands corresponding to the cleavage products were confirmed. The results are shown in FIGS. 1 to 3.

Example 2: Confirmation of Preference of Mutant SaCas9 for PAM Sequence

Using each mutant and wild-type SaCas9 prepared in Example 1 as mutant SaCas9, cleavage activity was examined in the same manner as in Example 1, and preference for various PAM sequences was confirmed. The PAM sequences 1-4 are shown in Table 1.

TABLE 1

|  | base sequence |
| --- | --- |
| PAM sequence 1 | 5'-NNGAAA-3' |
| PAM sequence 2 | 5'-NNGTTT-3' |
| PAM sequence 3 | 5'-NNGGGG-3' |
| PAM sequence 4 | 5'-NNGCCC-3' |

Figure 4A:
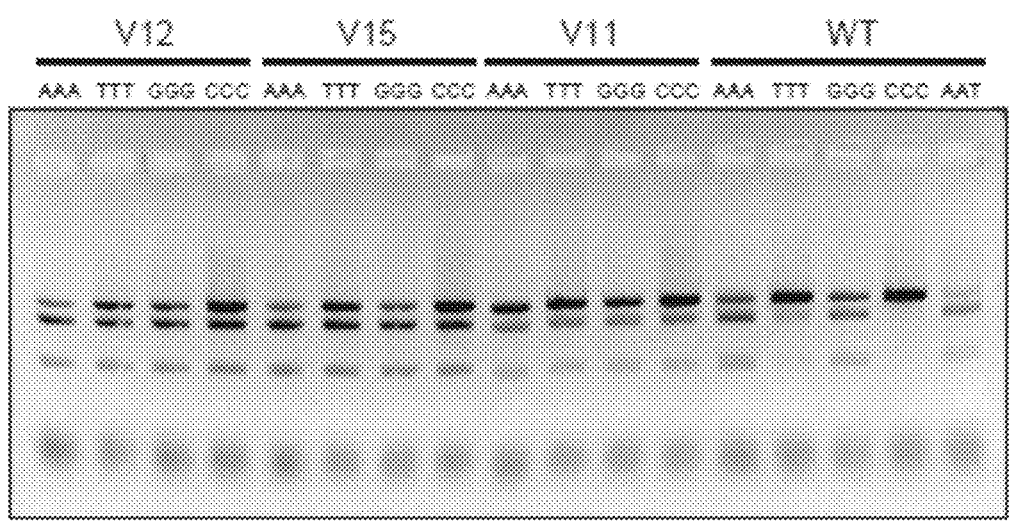
FIGS. 4A to 4D show images representing the results of agarose gel electrophoresis in a DNA cleavage activity measurement test in Example 2. PAM sequences of various mutant Cas9 proteins were examined.
Figure 4B:
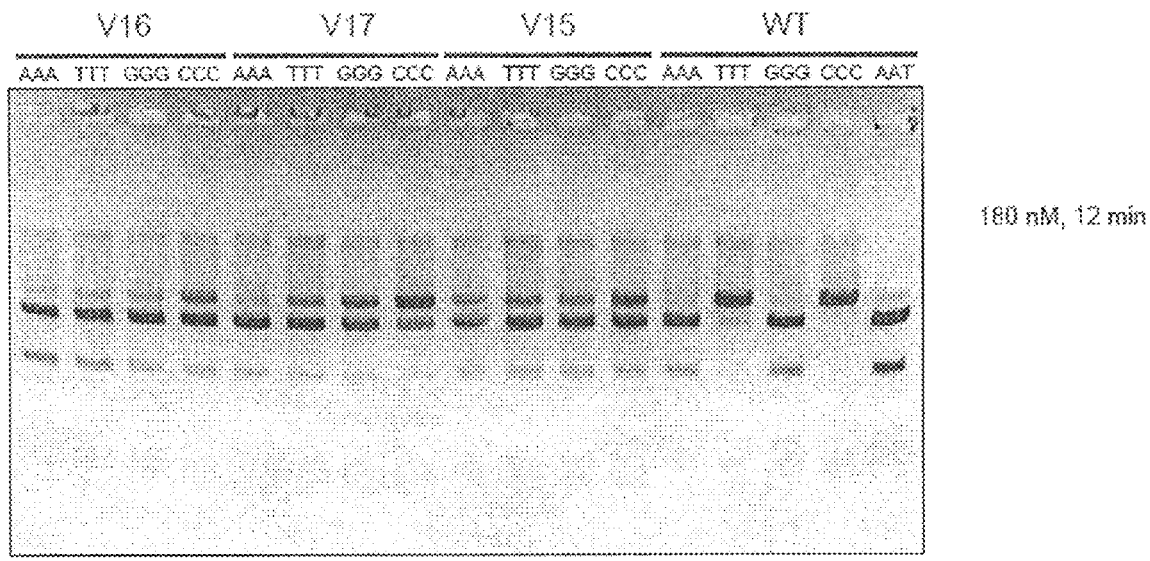

It has been confirmed that wild-type SaCas9 has a restricted cleavage activity on the target plasmid DNA, whereas restriction on the cleavage activity on the target plasmid DNA is improved in mutant SaCas9 (FIG. 4A, FIG. 4B).

Figure 4C:
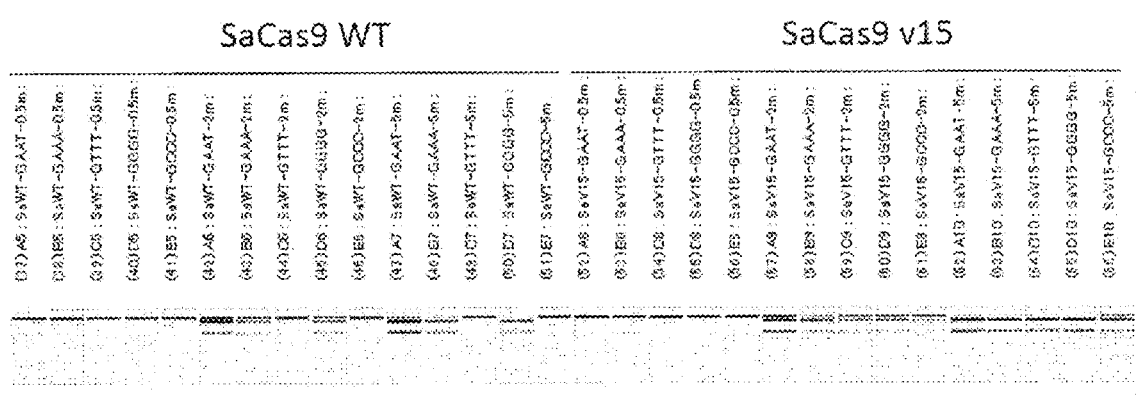
Figure 4D:
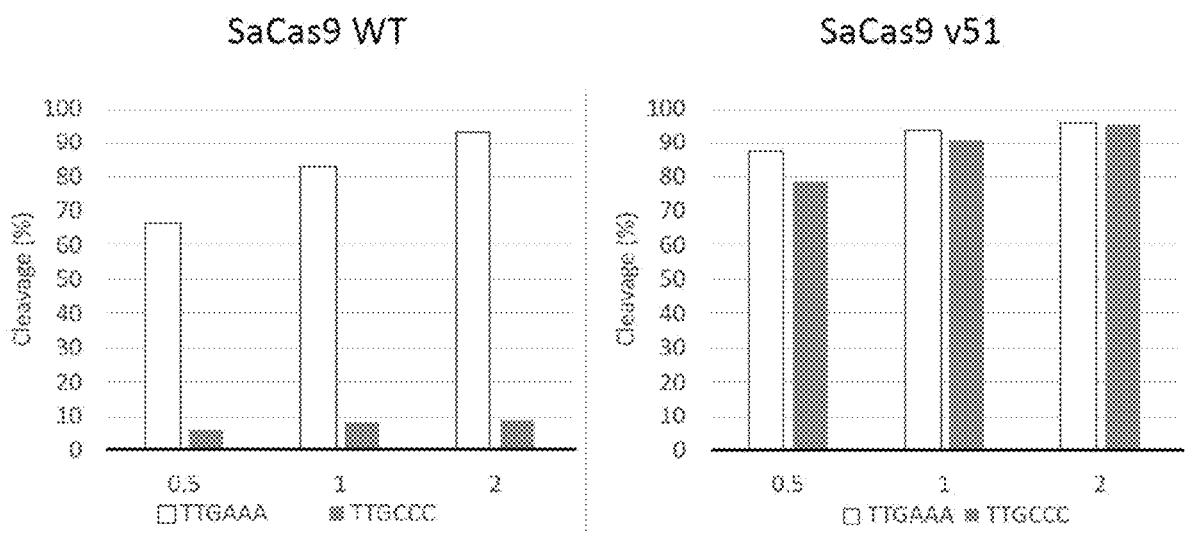
Figure 5A:
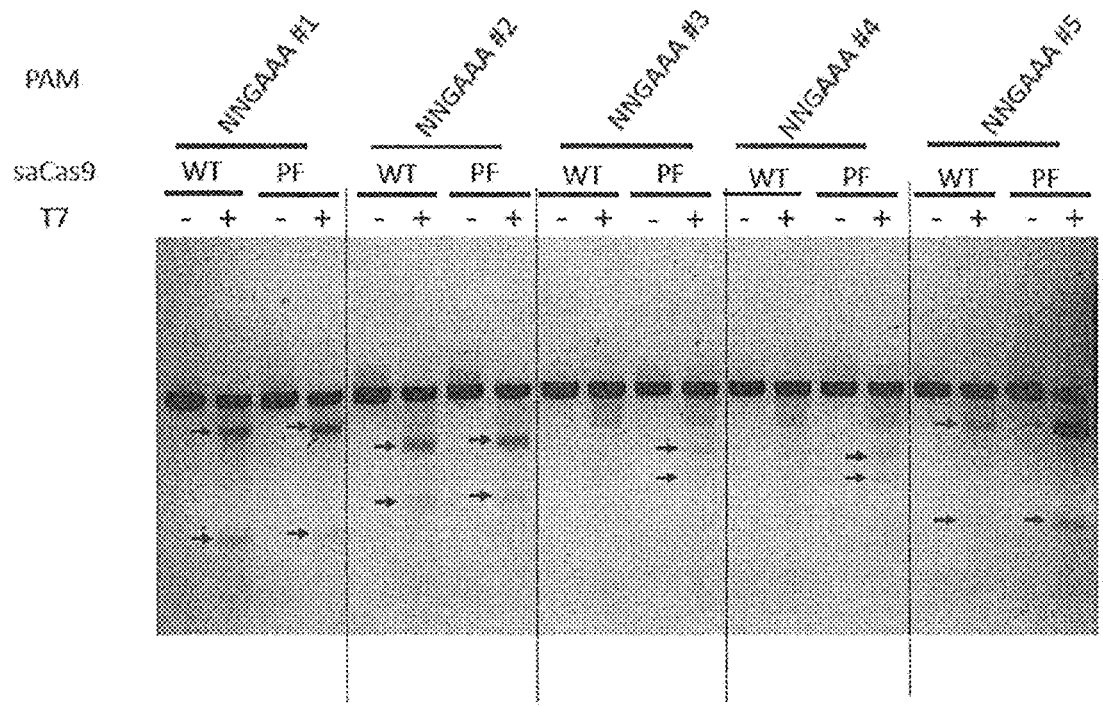
Figure 5C:
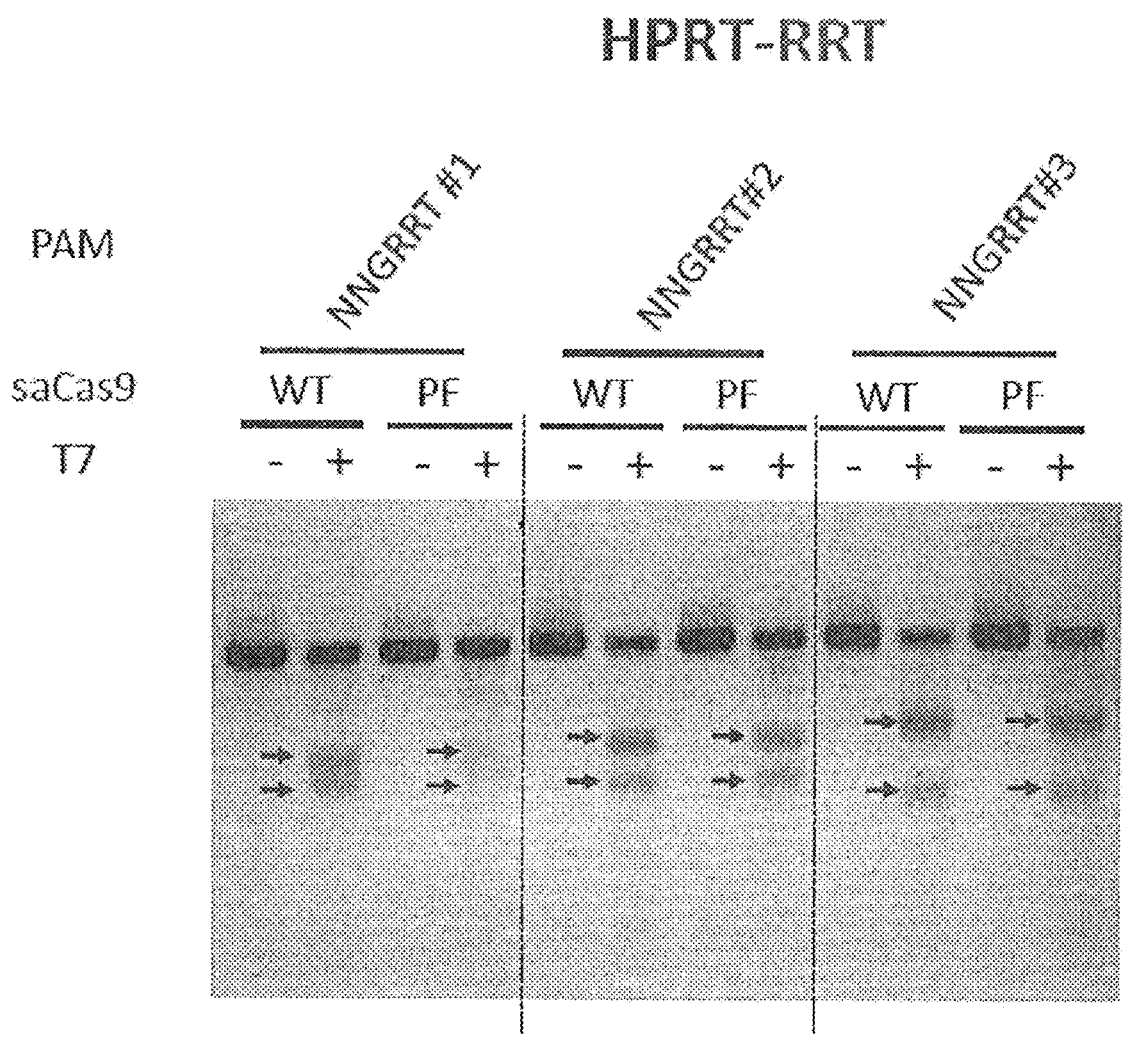
Figure 5D:
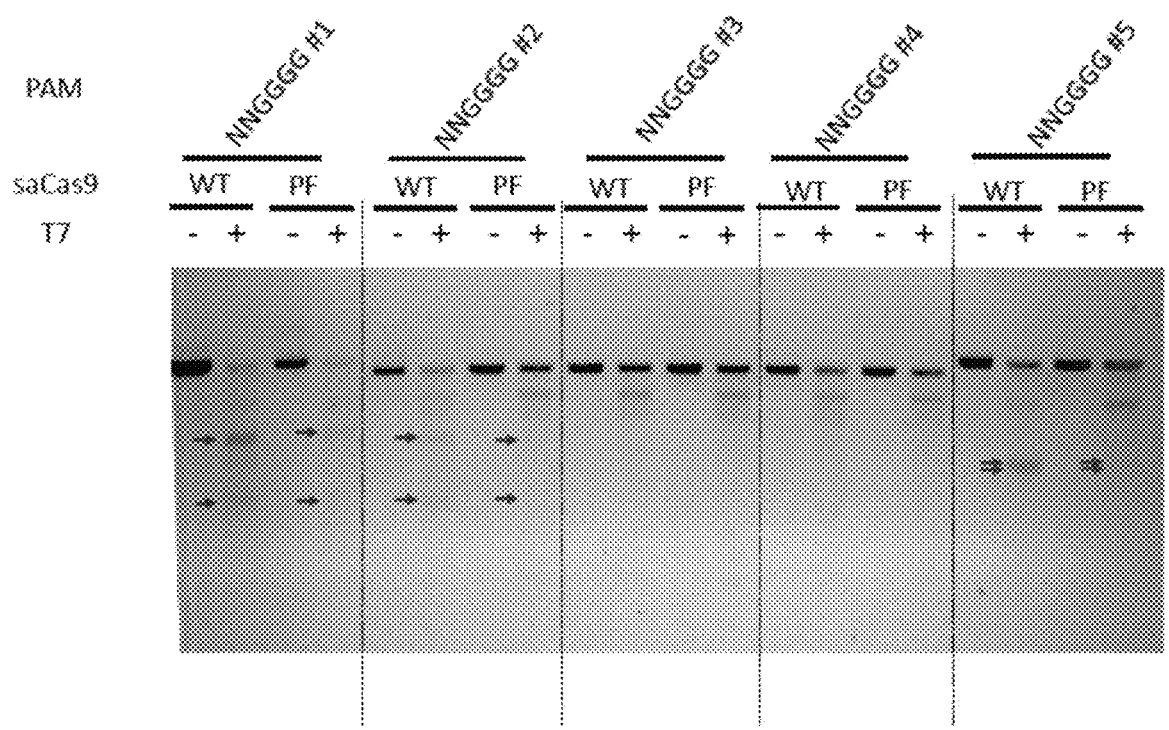
Figure 5F:
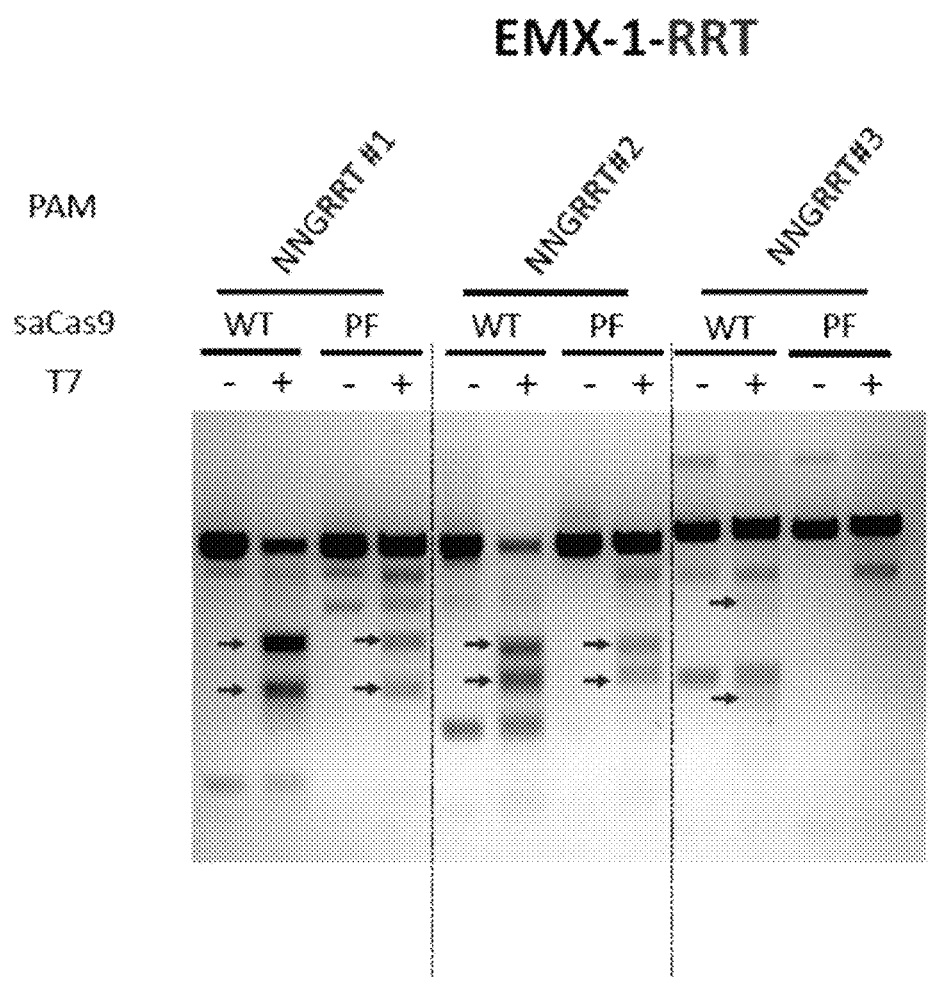

Using wild-type SaCas9 (SaCas9 WT) and mutant SaCas9 (SaCas9 v15) and in the same manner as in Example 1, the cleavage activity on the target plasmid DNA was examined by changing the treatment time, and preference for various PAM sequences was confirmed. As the PAM sequence, 5'-NNGAAT-3' (PAM sequence 5) was also examined in addition to the PAM sequences 1-4 described in Table 1. The results are shown in FIG. 4C. SaCas9 WT showed almost no cleavage activity on PAM sequence 4 at any treatment time, but SaCa9 v15 showed cleavage activity also on PAM sequence 4 after treatment for a given time or longer. In addition, SaCas9 v51, which is another mutant SaCas9, showed cleavage activity on PAM sequence 4 (5'-TTGCCC-3') even with a shorter treatment time (FIG. 4D).

Example 3

1. Verification of Target Gene Cleavage Activity in Eukaryotic Cells (1) Construct Design Wild-type or mutant SaCas9 gene with codon optimized by gene synthesis was incorporated in the BglII/XhoI site of CP-LvC9NU-09 vector (Genocopia). In addition, to target a plurality of sequences in HPRT and EMX1 genes, various guide RNA expression plasmids were produced by incorporating guide RNAs into the BsmB1 site of the pCRISPR-LvSG03 (Genocopia) vector. The constitution of each guide RNA expression plasmid is shown in Table 2.

TABLE 2

|  | Position | Strand | Spacer Sequence | PAM |
| --- | --- | --- | --- | --- |
|  | HPRT | | NNGAAA- | PAM |
| HPRT A-1 | 134473270 | -1 | AAAAATAACCTTAGTCTATCA (SEQ ID NO: 5) | GAGAAA |
| HPRT A-2 | 134473330 | 1 | TTGTATCCTGTAATGCTCTCA (SEQ ID NO: 6) | TTGAAA |
| HPRT A-3 | 134473362 | -1 | ACCTGGTTCATCATCACTAAT (SEQ ID NO: 7) | CTGAAA |
| HPRT A-4 | 134473423 | 1 | CTAATCATTATGCTGAGGATT (SEQ ID NO: 8) | TGGAAA |

TABLE 2-continued

| | Position | Strand | Spacer Sequence | PAM |
|---|---|---|---|---|
| HPRT A-5 | 134473508 | -1 | GCTGATGTTTGAAATTAACAC (SEQ ID NO: 9) | AAGAAA |
| HPRT NNGTTT-PAM | | | | |
| HPRT T-1 | 134473305 | 1 | TTAACATCTTAATCCAATCAA (SEQ ID NO: 10) | ATGTTT |
| HPRT T-2 | 134473345 | -1 | TAATCTGAAAAGAAATATAG (SEQ ID NO: 11) | CTGTTT |
| HPRT T-3 | 134473431 | 1 | TATGCTGAGGATTTGGAAAGG (SEQ ID NO: 12) | GTGTTT |
| HPRT T-4 | 134473483 | 1 | GGTAAGTAAGATCTTAAAATG (SEQ ID NO: 13) | AGGTTT |
| HPRT T-5 | 134473525 | -1 | AAGTACTCAGAACAGCTGCTG (SEQ ID NO: 14) | ATGTTT |
| HPRT NNGRRT-PAM | | | | |
| HPRT R-1 | 134473416 | 1 | TGCATACCTAATCATTATGCT (SEQ ID NO: 15) | GAGGAT |
| HPRT R-2 | 134473427 | 1 | TCATTATGCTGAGGATTTGGA (SEQ ID NO: 16) | AAGGGT |
| HPRT R-3 | 134473449 | -1 | CCTGTCCATAATTAGTCCATG (SEQ ID NO: 17) | AGGAAT |
| EMX1 NNGCCC-PAM | | | | |
| EMX1 C-1 | 72934106 | -1 | TGCTTGTCCCTCTGTCAATGG (SEQ ID NO: 18) | CGGCCC |
| EMX1 C-2 | 72934025 | -1 | GGAGTGGCCAGAGTCCAGCTT (SEQ ID NO: 19) | GGGCCC |
| EMX1 C-3 | 72931452 | 1 | GGCTTCTCAGGAATGACACCC (SEQ ID NO: 20) | CGGCCC |
| EMX1 C-4 | 72931442 | -1 | GGCCGGGGTGTCATTCCTGAG (SEQ ID NO: 21) | AAGCCC |
| EMX1 C-5 | 72931600 | 1 | GAGAACCACCCAGGGTCCAGG (SEQ ID NO: 22) | TGGCCC |
| EMX1 NNGGGG-PAM | | | | |
| EMX1 G-1 | 72931461 | -1 | GACTCAGGGCCAGATGCAGGG (SEQ ID NO: 23) | CCGGGG |
| EMX1 G-2 | 72934016 | -1 | AGAGTCCAGCTTGGGCCCACG (SEQ ID NO: 24) | CAGGGG |
| EMX1 G-3 | 72934051 | 1 | TGGCCACTCCCTGGCCAGGCT (SEQ ID NO: 25) | TTGGGG |
| EMX1 G-4 | 72934091 | 1 | TGGCCCCACAGGGCTTGAAGC (SEQ ID NO: 26) | CCGGGG |
| EMX1 G-5 | 72931539 | 1 | ACAGTCATAGCAGGCTCCAGG (SEQ ID NO: 27) | GTGGGG |
| EMX1 NNGRRT-PAM | | | | |
| EMX1 R-1 | 72934047 | -1 | GGCCTCCCCAAAGCCTGGCCA (SEQ ID NO: 28) | GGGAGT |
| EMX1 R-2 | 72934062 | 1 | TGGCCAGGCTTTGGGGAGGCC (SEQ ID NO: 29) | TGGAGT |
| EMX1 R-3 | 72931439 | 1 | GCCAGCCCACTTGGGCTTCTC (SEQ ID NO: 30) | AGGAAT |

(2) Expression in HEK Cells

HEK strain was transformed with the produced two kinds of SaCas9 expression vectors LvNUC9-09SaCas9 (wildtype (WT), PAM-flexible variant (PF)) (250 ng) and guide RNA expression plasmid (LvSG03 sgRNA) in a 24 well plate by the use of lipofectamine (Lipofectamine 2000). After culturing for one day, 1 μg/ml puromycin was added to the medium and the cells were recovered on day 4.

(3) PCR

From the recovered cells, samples were prepared using Extraction Buffers 1 and 2 of Guide-it™ Mutation Detection Kit (631448) (Clontech). Then, PCR was performed using Q5 (registered trade mark) Hot Start High-Fidelity 2× Master Mix (M0494) (NEB). The detailed PCR conditions were as follows.

```
HPRT PCR primer (Amplicon size: 468 bps)
Forward:
                                            (SEQ ID NO: 31)
TACACGTGTGAACCAACCCG Reverse:
                                            (SEQ ID NO: 32)
GTAAGGCCCTCCTCTTTTATTT EMX1 region A PCR primer
(Amplicon size: 643 bps)
Forward:
                                            (SEQ ID NO: 33)
AGTTTCTCATCTGTGCCCCTCC Reverse:
                                            (SEQ ID NO: 34)
CTGAACGCGTTTGCTCTACCAG EMX1 region B PCR primer
(Amplicon size: 732 bps)
Forward:
                                            (SEQ ID NO: 35)
TTTCACTTGGGTGCCCTAGG Reverse:
                                            (SEQ ID NO: 36)
CCCTCTTGCCAGAACTTCC
Cycling Conditions
Initial Denaturation: 98° C., 30 sec
35 cycles: 98° C. (5 sec), 63° C.
(20 sec), 72° C. (20 sec)
Final Extension: 72° C., 2 min
Hold: 4-10° C.
```

(4) T7 Endonuclease I Treatment

The obtained PCR product was heat denatured and annealed again. The obtained reaction product was treated with T7 Endonuclease I (T7 Enconuclease I (M0302)) and the obtained sample was electrophoresed using 1% concentration of agarose gel, and bands corresponding to the cleavage products were confirmed. The results are shown in FIGS. 5A to 5F.

Example 4: Off-Target Analysis of Cas9 Variant (Method)

1. Cloning

Using dSaCas9 (protein in which, in the sequence shown in SEQ ID NO: 2, aspartic acid at the 10-position is substituted with alanine and asparagine at the 580-position is substituted with alanine: also referred to as dSaCas9 (D10A, N580A)) and mutant dSaCas9 obtained by introducing a mutation therein, off-target analysis was performed. dSaCas9 is one introduced a null mutation into a wild-type SaCas9.

A gene construct of mutant dSaCas9 in which KRAB-P2A-Puro is linked to the C-terminal of a dSaCas9 (D10A, N580A) protein having a nuclear localization signal (NLS) linked to both ends was incorporated into pX601 vector (F. Ann Ran et al., Nature 2015; 520(7546); pp. 186-191).

Mutant dSaCas9 was produced by introducing null mutation (D10A, N580A) by the use of mutant SaCas9 (v15) or mutant SaCas9 (v51) produced in Example 1 instead of wild-type SaCas9. WT-dSaCas9-KRAB (SEQ ID NO: 37 and SEQ ID NO: 38; FIG. 6A and FIG. 6B)

PF(v15)-dSaCas9 (D10A, N580A)-KRAB (SEQ ID NO: 39 and SEQ ID NO: 40; FIG. 7A and FIG. 7B)

PF(v51)-dSaCas9 (D10A, N580A)-KRAB (SEQ ID NO: 41 and SEQ ID NO: 42; FIG. 8A and FIG. 8B)

2. Selection and Cloning of sgRNA (Single-Molecule Guide RNA) Sequence

Guide sequence targeting the KRAS gene was selected based on the predicted on-target and off-target scores obtained by Benchling software (www.benchling.com). The sequence is in the chr12:25,249,500-25,253,000 region published by the UCSC genome browser (Human GRCh38/hg38 assembly). A guide RNA compatible with WT-dSaCas9 (#1, 2, 3) is different from a guide RNA compatible with PF(v15)-dSaCas9 (#4, 5, 6) since PAM sequence has been changed.

The three control RNA guides (C1, C2, C3) were selected from Human CRISPR Knockout Pooled Library (Sanjana N. et al, Nat Methods. 2014 Aug.; 11(8):783-784). The stuffer sequence is a nucleotide sequence present in advance in the effector plasmid before cloning the guide RNA and acts as another control guide RNA sequence.

All guide RNAs were fused to tracer RNA sequences to produce sgRNAs, which were cloned into effector vectors as follows:

px601-AIO-CMV-WT-dSaCas9-Puro; #1, 2, 3, C1, C2, C3, stuffer px601-AIO-CMV-PF(v15)dSaCas9-Puro; #4, 5, 6, C1, C2, C3, stuffer px601-AIO-CMV-PF(v51)dSaCas9-Puro; C1, C2, C3

SgRNA expression is driven by the U6 promoter and the vector is constructed to express puromycin gene under P2A promoter to facilitate tracking and selection of sgRNA expressing cells.

The sequence information of each sgRNA and stuffer sequence is as follows.

```
sgRNA-KRAS#1 (WT);
                                    (SEQ ID NO: 43)
GGGAAGGCTGGACCGAGGCAG sgRNA-KRAS#2 (WT) ;
                                    (SEQ ID NO: 44)
CAGTCCGAAATGGCGGGGCC sgRNA-KRAS#3 (WT) ;
                                    (SEQ ID NO: 45)
AATCGAGCTCCGAGCACACCG sgRNA-KRAS#4 (PF-v15);
                                    (SEQ ID NO: 46)
GTGCGGGAGAGAGGTACGGAG sgRNA-KRAS#5 (PF-v15);
                                    (SEQ ID NO: 47)
GGAGCGAGCGCGGCGCAGGCA sgRNA-KRAS#6 (PF-v15);
                                    (SEQ ID NO: 48)
CGGCCGCGGCGGCGGAGGCAG
```

```
-continued
sgRNA-C1;
                                    (SEQ ID NO: 49)
ACGGAGGCTAAGCGTCGCAA sgRNA-C2;
                                    (SEQ ID NO: 50)
CGCTTCCGCGGCCCGTTCAA sgRNA-C3;
                                    (SEQ ID NO: 51)
GTAGGCGCGCCGCTCTCTAC Stuffer sequence;
                                    (SEQ ID NO: 52)
GAAACACCGGAGACCACGGCAGGTCTCA
```

3. Cell Culture and Transfection

HEK293FT cells were seeded in a 24-well plate at a density of 75,000 cells per well 24 hr before transfection and cultured in DMEM medium supplemented with 10% FBS, 2 mM fresh L-glutamine, 1 mM sodium pyruvate and non-essential amino acid. The cells were transfected according to the manual and using 500 ng of px601-CMV-WT-dSaCas9-Puro, px601-CMV-PF(v15)dSaCas9-Puro or px601-CMV-PF(v51)dSaCas9-Puro, each containing one of sgRNAs, and 1.5 µl Lipofectamine 2000 (Life technologies). At 72 hr after transfection (48 hr after selection of 1 µg/ml puromycin), the cells were recovered and dissolved in RLT buffer (Qiagen), and the total RNA was extracted using RNeasy kit (Qiagen).

4. Submission of Samples for RNAseq Analysis

Samples were prepared in duplicate for each experiment and 2.5 µg of total RNA per sample was analyzed with GENEWIZ. The RNA library was prepared by poly-A selection followed by sequencing (Illumina HiSeq, 2×150 b.p., single index per lane sequencing configuration) as shown in GENEWIZ (www.genewiz.com). All RNAs met GENEWIZ QC criteria. The target untreated paired-end read was 25M per sample.

5. A raw fastq file obtained by standard paired-endo illumina sequencing was aligned to *H. sapiens* genome build, GRCh38.p12 (https://useast.ensembl.org/Homo_sapiens/Info/Index) using Spliced Transcripts Alignment to a Reference (STAR) (http://labshare.cshl.edu/shares/gingeraslab/www-data/dobin/STAR/STAR.posix/doc/STARmanual.pdf). Biological replicates were grouped, and differential analysis between samples was performed in advance using DESeq2 (https://bioconductor.org/packages/release/bioc/html/DESeq2.html) using processed alignment data.

FKPM data files were processed; a gene group having no read in any of the samples, genes with average expression of less than 1.0 read, and a gene group having small transcripts (microRNAs and SNORs) were excluded from the analysis.

All replicate samples showed a correlation coefficient>98%. The average expression from the two replicates was used to calculate a representative expression value for each gene of each class. MvA plots were produced using MultiplotStudio software. The X-axis shows mean 2-class expression and the Y-axis shows log 2 fold-change between the two classes.

(Results)

It was found that PF(v15)-dSaCas9 more strongly suppresses the expression of KRAS gene and shows lower off-target suppression than WT-dSaCas9 (FIG. 9).

MvA plots of the classes having KRAS-sgRNA and control-stuffer sgRNA are respectively shown for WT-dSaCas9 and PF(v15)-dSaCas9. The X-axis shows mean of 2-class expression and the Y-axis shows log 2 fold-change between two classes. The KRAS gene was suppressed by WTdSaCas9 having three different sgRNAs (sgRNA #1, #2 and #3), and PF(v15)-Cas9 having three different sgRNAs (sgRNA #4, #5, #6). The log 2 fold-change suppression for control-stuffer sgRNA was as follows; −2.261 (sgRNA #1), −1.888 (sgRNA #2) and −2.934 (sgRNA #3), −5.041 (sgRNA #4), −2.538 (sgRNA #5) and −2.642 (sgRNA #6).

PF(v15)-dSaCas9 showed less off-target suppression. The number of genes suppressed not less than twice compared to control-stuffer sgRNA was 71 (sgRNA #1), 93 (sgRNA #2) or 57 (sgRNA #3) for WT-dSaCas9, whereas it was 38 (#4), 23 (#5) or 35 (#6) for PF(v15)-dSaCas9.

The off-target suppressive effect of PF(v15) and PF(v51) on WT-dSaCas9 was examined (FIG. 10).

The MvA plot shows the number of genes that showed suppression of not less than twice on WT-dSaCas9 by PF(v15) and PF(v51). The comparison was performed using three control sgRNAs; C1, C2 and C3 and by PF(v15) vs. WT and PF(v51) vs. WT. PF(v15) showed extremely low numbers of off-target suppression (more than 2-fold suppression) of 5, 7 and 7 genes respectively for C1, C2 and C3. PF(v51) showed greater numbers of off-target suppression (more than 2-fold suppression) of 84, 26 and 16 genes respectively for C1, C2 and C3. The X-axis shows mean of 2-class expression and the Y-axis shows log 2 fold-change between two classes.

INDUSTRIAL APPLICABILITY

According to the present invention, a Cas9 protein can be obtained that recognizes a wide range of PAM sequences while retaining binding strength with a guide RNA. This Cas9 protein has a strong target DNA binding ability as compared to that of WT Cas9 protein, and also shows low off-target binding ability. In addition, a simple and rapid site-specific genome editing technology for a target sequence can be provided that uses the aforementioned Cas9 protein.

This application is based on U.S. provisional patent application No. 62/554,227 (filing date: Sep. 5, 2017) U.S. provisional patent application No. 62/668,968 (filing date: May 9, 2018), and U.S. provisional patent application No. 62/724,981 (filing date: Aug. 30, 2018), each filed in US, the contents of which are incorporated in full herein.

The invention claimed is:

1. A polynucleotide encoding a protein having at least 80% sequence identity to SEQ ID NO:2 with mutations at the 985-position and the 991-position, and optionally the 986-position, wherein said protein further comprises:

[I] mutations as at least five sites selected from the group consisting of the 782-position, the 800-position, the 888-position, the 968-position, the 988-position, the 1017-position and the 1021-position; and (i) mutations at the 927-position and the 929-position, (ii) a mutation at the 889-position, or (iii) mutations at the 927-position, the 929-position and the 889-position, and has a binding ability to guide RNA.

2. The polynucleotide according to claim 1, wherein the protein comprises mutation at at least 6 sites selected from the group consisting of the 782-position, the 800-position, the 888-position, the 968-position, the 988-position, the 1017-position and the 1021-position.

3. The polynucleotide according to claim 1, wherein:
the mutation at the 782-position is substitution with lysine;
the mutation at the 800-position is substitution with arginine;
the mutation at the 888-position is substitution with lysine;
the mutation at the 968-position is substitution with arginine;
the mutation at the 985-position is substitution with alanine;
the mutation at the 986-position is substitution with alanine;
the mutation at the 991-position is substitution with alanine;
the mutation at the 988-position is substitution with histidine;
the mutation at the 1017-position is substitution with phenylalanine; and
the mutation at the 1021-position is substitution with serine;
the mutation of (i) is substitution of the 927-position with lysine, and substitution of the 929-position with asparagine or aspartic acid;
the mutation of (ii) is substitution of the 889-position with arginine; and
the mutation of (iii) is substitution of the 927-position with lysine, substitution of the 929-position with asparagine, and substitution of the 889-position with asparagine.

4. The polynucleotide according to claim 1, wherein the protein consists of a sequence comprising an amino acid sequence resulting from substitutions of:
glutamic acid at the 782-position with lysine,
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
threonine at the 927-position with lysine; and
lysine at the 929-position with asparagine; in the amino acid sequence shown in SEQ ID NO: 2;
and having a binding ability to guide RNA.

5. The polynucleotide according to claim 1, wherein the protein consists of a sequence comprising an amino acid sequence resulting from substitutions of:
glutamic acid at the 782-position with lysine;
leucine at the 800-position with arginine;
asparagine at the 968-position with arginine;
asparagine at the 985-position with alanine;
asparagine at the 986-position with alanine;
arginine at the 991-position with alanine;
leucine at the 988-position with histidine;
alanine at the 1021-position with serine;
alanine at the 889-position with asparagine;
threonine at the 927-position with lysine; and
lysine at the 929-position with asparagine; in the amino acid sequence shown in SEQ ID NO: 2;
and having a binding ability to guide RNA.

6. The polynucleotide according to claim 1, wherein the protein consists of a sequence comprising an amino acid sequence resulting from substitutions of:
glutamic acid at the 782-position with lysine,
leucine at the 800-position with arginine;
asparagine at the 968-position with arginine;
asparagine at the 985-position with alanine;
arginine at the 991-position with alanine;
alanine at the 1021-position with serine;
threonine at the 927-position with lysine;
lysine at the 929-position with asparagine; and
isoleucine at the 1017-position with phenylalanine; in the amino acid sequence shown in SEQ ID NO: 2;
and having a binding ability to guide RNA.

7. The polynucleotide according to claim 1, wherein
the protein has identity of 90% or more at a site other than the mutated positions in the SEQ ID NO: 2.

8. The polynucleotide according to claim 1, wherein the protein has one to several amino acids are substituted, deleted, inserted and/or added at a site other than the mutated positions in the SEQ ID NO: 2, while having at least 80% sequence identity to SEQ ID NO:2.

9. The polynucleotide according to claim 1, wherein the protein has RNA-guided DNA endonuclease activity.

10. The polynucleotide according to claim 1, wherein the protein further has a mutation that deletes nuclease activity in the amino acid sequence as set forth in SEQ ID NO: 2.

11. The polynucleotide according to claim 1, wherein the protein further has a mutation that deletes nuclease activity in the amino acid sequence shown in SEQ ID NO: 2 and has mutation at sites corresponding to the 10-position, the 556-position, the 557-position and/or the 580-position in the amino acid sequence as set forth in SEQ ID NO: 2.

12. The polynucleotide according to claim 11, wherein:
the mutation at the 10-position is substitution of aspartic acid with alanine;
the mutation at the 556-position is substitution of aspartic acid with alanine;
the mutation at the 557-position is substitution of histidine with alanine; and
the mutation at the 580-position is substitution of asparagine with alanine.

13. The polynucleotide according to claim 10, wherein a transcriptional regulator protein or domain is linked to the N-terminal or C-terminal of the mutant Cas9 protein.

14. The polynucleotide according to claim 13, wherein the transcriptional regulator protein is a transcription activator.

15. The polynucleotide according to claim 14, wherein the transcriptional regulator protein is a transcription silencer or a transcription inhibitor.

* * * * *